US012808774B2

(12) United States Patent
Park et al.

(10) Patent No.: US 12,808,774 B2
(45) **Date of Patent: *Nov. 24, 2026**

(54) METHODS AND APPARATUS FOR A TWENTY-FIVE-COLOR FLUORESCENCE-BASED ASSAY AND FLOW CYTOMETRY PANEL

(71) Applicant: Cytek Biosciences, Inc., Fremont, CA (US)

(72) Inventors: Lily M. Park, Fremont, CA (US); Maria C. Jaimes, Fremont, CA (US)

(73) Assignee: Cytek Biosciences, Inc., Fremont, CA (US)

( * ) Notice: Subject to any disclaimer, the term of this patent is extended or adjusted under 35 U.S.C. 154(b) by 140 days.

This patent is subject to a terminal disclaimer.

(21) Appl. No.: 18/331,165

(22) Filed: Jun. 7, 2023

(65) Prior Publication Data

US 2024/0337581 A1 Oct. 10, 2024

(51) Int. Cl.
*G01N 15/1434* (2024.01)
*G01N 33/52* (2006.01)

(52) U.S. Cl.
CPC ......... *G01N 15/1436* (2013.01); *G01N 33/52* (2013.01)

(58) Field of Classification Search
CPC ........... G01N 15/0205; G01N 15/1434; G01N 2015/0065; G01N 2015/0084; G01N 2015/1006; G01N 2015/1438; G01N 2015/144; G01N 2015/1493
See application file for complete search history.

(56) References Cited

U.S. PATENT DOCUMENTS

| | | | | |
|---|---|---|---|---|
| 12,209,948 | B2 * | 1/2025 | Jaimes | G01N 15/0205 |
| 2010/0248390 | A1 * | 9/2010 | Matsunami | G01N 33/566 702/19 |
| 2019/0228527 | A1 * | 7/2019 | Ramirez | G16H 30/40 |
| 2022/0323503 | A1 * | 10/2022 | Biffi | A61K 31/255 |
| 2022/0335609 | A1 * | 10/2022 | Ramirez | G16H 30/40 |
| 2024/0027457 | A1 * | 1/2024 | Chang | G01N 33/57426 |

OTHER PUBLICATIONS

Ferrer-Font, L., Pellefigues, C. Mayer J. U., Small. S.J. Jaimes, M.C., & Price, K.M. (2020). Panel design and optimization for high-dimensional immunophenotyping assays using spectral flow cytometry. Current Protocols in Cytometry, 92, e70., doi:10.1002/cpcy.70.

* cited by examiner

*Primary Examiner* — Michael A Lyons
(74) *Attorney, Agent, or Firm* — Alford Law Group, Inc.; Vy H. Vu

(57) ABSTRACT

In one embodiment, a method of building an optimized color flow cytometry panel is disclosed using a full spectrum flow cytometer with four excitation lasers and forty-eight color detectors. In another embodiment, a graphical user interface is disclosed generated by a server computer from a fluorochrome database and displayed by a client computer to assist in the selection of a set of fluorochromes for use in an assay to analyze biological samples. The GUI can display spectra graphs to visually show how fluorochromes may overlap and can generate similarity indexes for the paired fluorochrome interference and a complexity index for overall many to many interferences generated by a selected group or set of fluorochromes.

13 Claims, 73 Drawing Sheets
(65 of 73 Drawing Sheet(s) Filed in Color)

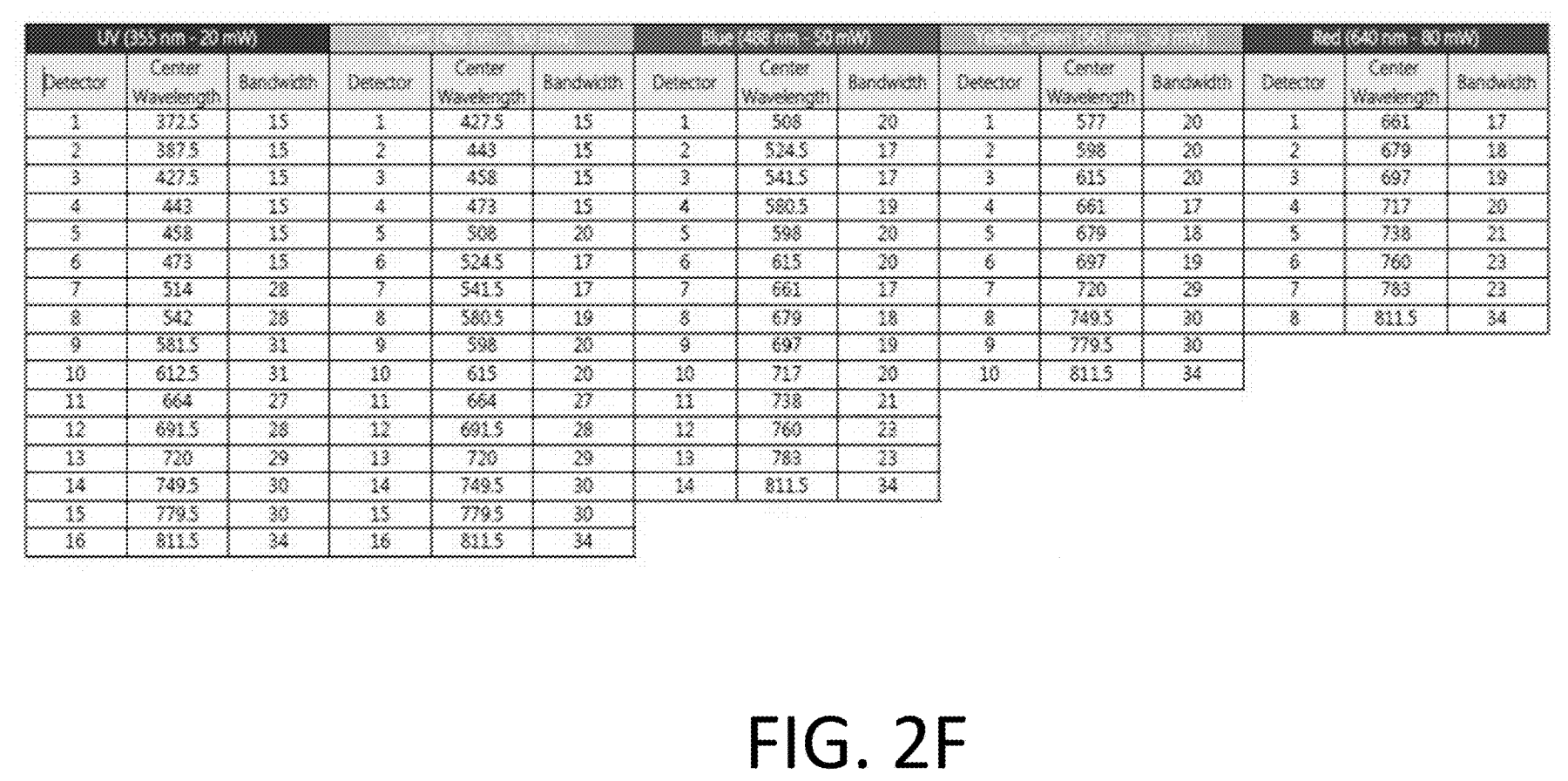

| UV (355 nm - 20 mW) | | | | | | Blue (488 nm - 50 mW) | | | | | | Red (640 nm - 80 mW) | | |
|---|---|---|---|---|---|---|---|---|---|---|---|---|---|---|
| Detector | Center Wavelength | Bandwidth | Detector | Center Wavelength | Bandwidth | Detector | Center Wavelength | Bandwidth | Detector | Center Wavelength | Bandwidth | Detector | Center Wavelength | Bandwidth |
| 1 | 372.5 | 15 | 1 | 427.5 | 15 | 1 | 508 | 20 | 1 | 577 | 20 | 1 | 661 | 17 |
| 2 | 387.5 | 15 | 2 | 443 | 15 | 2 | 524.5 | 17 | 2 | 598 | 20 | 2 | 679 | 18 |
| 3 | 427.5 | 15 | 3 | 458 | 15 | 3 | 541.5 | 17 | 3 | 615 | 20 | 3 | 697 | 19 |
| 4 | 443 | 15 | 4 | 473 | 15 | 4 | 580.5 | 19 | 4 | 661 | 17 | 4 | 717 | 20 |
| 5 | 458 | 15 | 5 | 508 | 20 | 5 | 598 | 20 | 5 | 679 | 18 | 5 | 738 | 21 |
| 6 | 473 | 15 | 6 | 524.5 | 17 | 6 | 615 | 20 | 6 | 697 | 19 | 6 | 760 | 23 |
| 7 | 514 | 28 | 7 | 541.5 | 17 | 7 | 661 | 17 | 7 | 720 | 29 | 7 | 783 | 23 |
| 8 | 542 | 28 | 8 | 580.5 | 19 | 8 | 679 | 18 | 8 | 749.5 | 30 | 8 | 811.5 | 34 |
| 9 | 581.5 | 31 | 9 | 598 | 20 | 9 | 697 | 19 | 9 | 779.5 | 30 | | | |
| 10 | 612.5 | 31 | 10 | 615 | 20 | 10 | 717 | 20 | 10 | 811.5 | 34 | | | |
| 11 | 664 | 27 | 11 | 664 | 27 | 11 | 738 | 21 | | | | | | |
| 12 | 691.5 | 28 | 12 | 691.5 | 28 | 12 | 760 | 23 | | | | | | |
| 13 | 720 | 29 | 13 | 720 | 29 | 13 | 783 | 23 | | | | | | |
| 14 | 749.5 | 30 | 14 | 749.5 | 30 | 14 | 811.5 | 34 | | | | | | |
| 15 | 779.5 | 30 | 15 | 779.5 | 30 | | | | | | | | | |
| 16 | 811.5 | 34 | 16 | 811.5 | 34 | | | | | | | | | |

FIG. 2F

| UV | | VIOLET | | BLUE | | YELLOW GREEN | | RED | |
|---|---|---|---|---|---|---|---|---|---|
| SPECIFICITY | FLUOROCHROME | SPECIFICITY | FLUOROCHROME | SPECIFICITY | FLUOROCHROME | SPECIFICITY | FLUOROCHROME | SPECIFICITY | FLUOROCHROME |
| CD40 | BD Horizon™ BUV395 | CX3CR1 | BV421 | CD26 | FITC | CD197 | PE | CD272 | APC |
| CD16 | BD Horizon™ BUV496 | CD38 | eFluor 450 | CD32 | BD Horizon™ BB700 | CD163 | PE/Dazzle 594 | CD1c | AF647 |
| CD56 | BD Horizon™ BUV563 | CD85k | BV480 | | | CD80 | PE-Cy5 | CD11c | AF700 |
| CD3 | BD Horizon™ BUV661 | CD8 | BV510 | | | CD19 | PE-Cy5.5 | HLA-DR | APC-H7 |
| CD86 | BD Horizon™ BUV737 | CD45RA | BV570 | | | CD4 | PE-Cy7 | | |
| CD45 | BD Horizon™ BUV805 | CD141 | BV605 | | | | | | |
| Dead Cells | Live/Dead Blue | CD172a | BV650 | | | | | | |
| | | CD14 | BV711 | | | | | | |
| | | CD11b | BV750 | | | | | | |
| | | CD123 | BV786 | | | | | | |

28 Color panel

FIG. 3

2067.P016P1

| Violet | | | Blue | | | Yellow-Green | | | Red | | |
|---|---|---|---|---|---|---|---|---|---|---|---|
| Specificity | Clone | Fluorochrome | Specificity | Clone | Fluorochrome | Specificity | Clone | Fluorochrome | Specificity | Clone | Fluorochrome |
| CCR7 | G043H7 | BV421* | CD141 | M80 | cFluor B515 | CD25 | BC96 | cFluor BYG575 | CD127 | A019D5 | cFluor R659 |
| CD45RA | HI100 | cFluor V450 | CD8 | SK1 | cFluor B520 | CD4 | SK3 | cFluor YG584 | CD1c | L161 | cFluor R668 |
| IgM | MHM-88 | BV510* | CD14 | 63D3 | cFluor B548 | CD16 | 3G8 | cFluor BYG610 | CD19 | HIB19 | cFluor R685 |
| CD20 | 2H7 | cFluor V547 | HLADR | L243 | cFluor B690 | IgD | IA6-2 | cFluor BYG667 | CD123 | 6H6 | cFluor R720 |
| CD3 | UCHT1 | BV570* | | | | TCRgd | B1 | cFluor BYG710 | CD45 | 2D1 | cFluor R780 |
| CD28 | CD28.2 | BV650* | | | | CD11c | 3.9 | cFluor BYG781 | CD27 | QA17A18 | cFluor R840 |
| CD38 | HIT2 | BV711* | | | | | | | | | |
| CD56 | 5.1H11 | BV750* | | | | | | | | | |
| PD-1 | EH12.2H7 | BV785* | | | | | | | | | |

25 Color Panel

Markers and Fluorochromes in a 25 color panel are summarized in the table above.

Human peripheral blood mononuclear cells were stained washed and acquired on a four laser flow cytometer

FIG. 5A

Clustering and Dimensionality Reduction Analysis

Clustering and Dimensionality Reduction Analysis - FLOSUM CLUSTERS

FIG. 5D
CD123 cFluor R720-A
CD1c cFluor R668-A
CD141 cFluor B515-A
PD-1 BV785-A
CD38 BV711-A
IgD cFluor BYG667-A
CD27 cFluor R840-A
IgM BV510-A
CD28 BV650-A
CCR7 BV421-A
CD45RA cFluor V450-A
CD11c cFluor BYG781-A
CD16 cFluor BYG610-A
HLA-DR cFluor B690-A
CD14 cFluor B548-A
CD56 BV750-A
CD20 cFluor V547-A
CD19 cFluor R685-A
TCRgd cFluor BYG710-A
CD8 cFluor B532-A
CD127 cFluor R659-A
CD25 cFluor BYG575-A
CD4 cFluor YG584-A
CD3 BV570-A
Cluster 02
Cluster 03
Cluster 11
Cluster 06
Cluster 25
Cluster 26
Cluster 30
Cluster 28
Cluster 29
Cluster 27
Cluster 23
Cluster 19
Cluster 08
Cluster 14
Cluster 24
Cluster 15
Cluster 10
Cluster 05
Cluster 13
Cluster 12
Cluster 07
Cluster 01
Cluster 16
Cluster 18
Cluster 17
Cluster 09
16.85

Marker Expression of FlowSOM Clusters

Spectrum Signature

| SPECIFICITY | FLUOROCHROME | CLONE | PURPOSE |
|---|---|---|---|
| Viability | Live Dead UV Blue | - | Viability |
| CD45 | PerCP | HI30 | Leukocytes |
| CD3 | BV510 | OKT3 | T cell lineage |
| CD4 | CF568 | SK3 | CD4 T cells |
| CD8 | BUV805 | SK1 | CD8 T cells |
| CD25 | PE-Alexa Fluor700 | CD25-3G10 | Regulatory T cells |
| TCRγδ | PerCP-eF710 | B1.1 | γδ T cells |
| CD14 | Spark Blue 550 | 63D3 | Monocytes |
| CD16 | BUV496 | 3G8 | |
| CD11c | eF450 | 3.9 | Monocytes/ Dendritic Cells |
| CD19 | Spark NIR 685 | HIB19 | B cells |
| CD20 | PO | HI47 | |
| CD24 | PE-Alexa Flour 610 | SN3 | B cell differentiation |
| CD39 | BUV661 | TU66 | |
| IgD | BV480 | IA6-2 | |
| IgG | BV605 | G18-145 | |
| IgM | BV570 | MHM-88 | |
| CD141 | BB515 | 1A4 | Dendritic cells |
| CD1c | AF647 | L161 | Dendritic cells/NKT cells |
| CD123 | SB436 | 6H6 | Plasmacytoid dendritic cells |
| CD2 | PerCP-Cy5.5 | TS1/8 | NK cells |
| CD56 | BUV737 | NCAM16.2 | |
| CCR7 | BV421 | G043H7 | T cell differentiation |
| CD27 | APC-H7 | M-T271 | |
| CD28 | BV650 | CD28.2 | |
| CD45RA | BUV395 | 5H9 | |
| CD95 | PE-Cy5 | DX2 | |
| CD127 | APC-R700 | HIL-7R-M21 | Cytokine receptor |
| CD337 | PE-Dazzle594 | P30-15 | |
| CCR6 | BV711 | G034E3 | Chemokine receptor |
| CCR5 | BUV563 | 2D7/CCR5 | |
| CXCR5 | BV750 | RF8B2 | |
| CXCR3 | PE-Cy7 | G025H7 | |
| HLA-DR | PE-Fire810 | L243 | Activation |
| CD38 | APC-Fire810 | HIT2 | |
| CD57 | FITC | HNK-1 | Immune senescence |
| PD-1 | BV785 | EH12.2H7 | Inhibitory receptor |
| CD159a | APC | REA110 | NK Cell Receptors |
| CD159c | PE | REA205 | |
| CD314 | BUV615 | 1D11 | |

FIG. 6A

40
Color
panel

Merged FlowSOM Plot for 40 Color panel

40 Color Panel

Remember Linear Unmixing Description Using Vectors Approach?
Assay:
- Reference Single Color Blue
- Reference Single Color Yellow
- Multicolor Sample (Green)
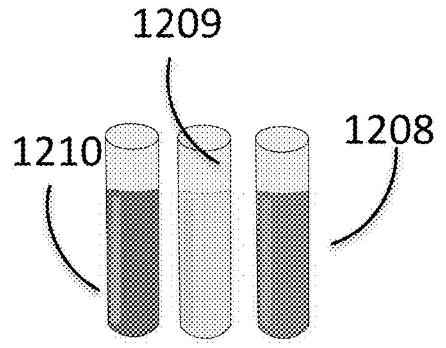
System: 3 Detector Spectral System
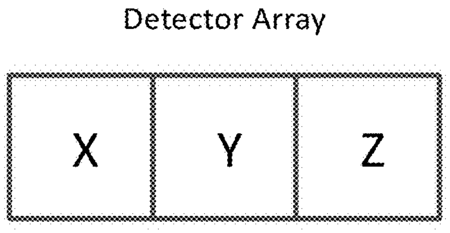
FIG. 9

Step 1: Establish Reference Control Vectors
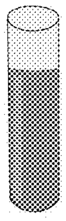
| Event # | X | Y | Z |
| --- | --- | --- | --- |
| 1 | 10 | 1000 | 20 |
| 2 | 12 | 998 | 22 |
| 3 | 8 | 1002 | 18 |
| ..... | ..... | ..... | ..... |
| 5000 | 10 | 1000 | 20 |
$(\tilde{X}_B \quad \tilde{Y}_B \quad \tilde{Z}_B)$
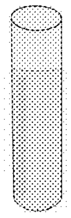
| Event # | X | Y | Z |
| --- | --- | --- | --- |
| 1 | 400 | 10 | 1000 |
| 2 | 410 | 12 | 998 |
| 3 | 390 | 8 | 1002 |
| ..... | ..... | ..... | ..... |
| 5000 | 400 | 10 | 1000 |
$(\tilde{X}_Y \quad \tilde{Y}_Y \quad \tilde{Z}_Y)$
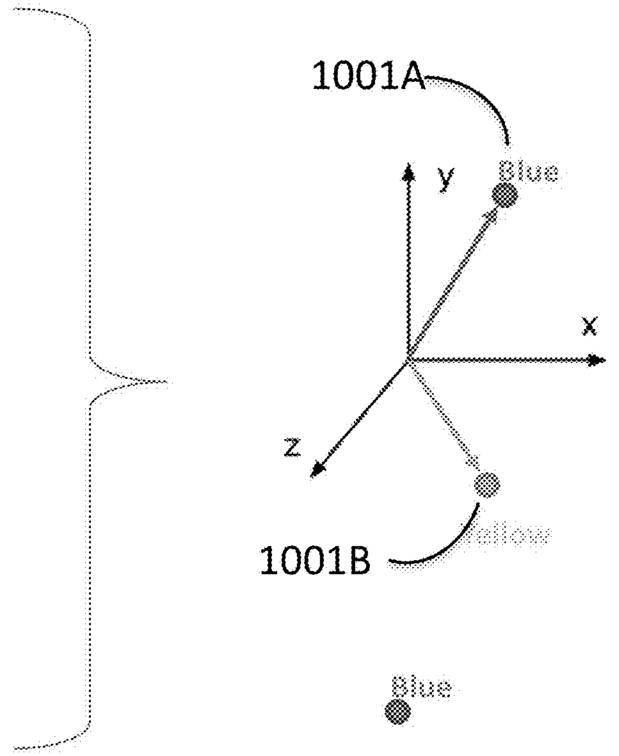
FIG. 10

Step 2: Project Sample Vectors
1210
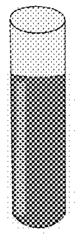
| Event # | $X_s$ | $Y_s$ | $Z_s$ | |
|---|---|---|---|---|
| 1 | 5 | 595 | 200 | $S_1$ |
| 2 | 1000 | 998 | 22 | $S_2$ |
| 3 | 8 | 1002 | 1000 | $S_3$ |
| ...... | ..... | ..... | ..... | |
| 50,000 | 998 | 22 | 1003 | $S_{50,000}$ |
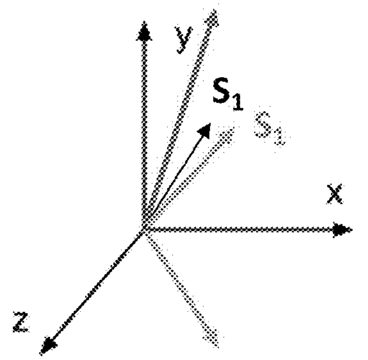
$S_1$ = (a * Blue) + (b * Yellow)
For Unmixing in a 3L Aurora, the mathematical algorithm looks at 38 different dimensions
For Unmixing in a 3L Aurora, the mathematical algorithm looks at 64 different dimensions
FIG. 12

What a Signature Looks Like to the Software

A 64 dimensional vector...

| UV1 | UV2 | UV3 ... | | ... R5 | R6 | R7 | R8 |
|---|---|---|---|---|---|---|---|
| 120 | 136 | 191 | ................................. | 16118 | 8842 | 5761 | 3080 |

...that can be compared spatially to other signatures to see how similar or different they are...

Mathematical Approach around Complexity Index (1)

Based on linear algebra Singular Value Decomposition, any matrix (M) can be decomposed into three matrix transformations: a rotation, a scaling, and another rotation $$M = U \cdot \Sigma \cdot V^*$$

https://en.wikipedia.org/wiki/Singular_value_decomposition

Dye pairs with Similarity Index > 0.88

0.89 CF568 vs PE
0.91 APC vs AF647
0.92 PerCP-Cy55 vs PerCP-eF710
0.94 SB436 vs eF450
0.96 BV421 vs SB436
0.97 FITC vs BB515

For these 35 fluorochromes, the maximum similarity Index we have is 0.97.

The Complexity Index is 46.43

Remove CF568, AF647, PerCP-eF710, SB436, & BB515:
Complexity Index reduces to 35.33

FIG. 18-1

| | BUV395 | BUV496 | BUV563 | BUV661 | BUV737 | BUV805 | BV421 | Super Bright 436 | eFluor 450 | LIVE DEAD Blue | BV480 | BV510 | Pacific Orange | BV570 | BV605 | BV650 | BV711 |
|---|---|---|---|---|---|---|---|---|---|---|---|---|---|---|---|---|---|
| BUV395 | 1 | 0.23 | 0.06 | 0.06 | 0.04 | 0.07 | 0.07 | 0.07 | 0.03 | 0.53 | 0.04 | 0.05 | 0.01 | 0.01 | 0.01 | 0.02 | 0.01 |
| BUV496 | 0.23 | 1 | 0.32 | 0.1 | 0.02 | 0.04 | 0.11 | 0.14 | 0.12 | 0.51 | 0.39 | 0.5 | 0.22 | 0.1 | 0.06 | 0.06 | 0.03 |
| BUV563 | 0.06 | 0.32 | 1 | 0.1 | 0.02 | 0.02 | 0.03 | 0.03 | 0.02 | 0.07 | 0.08 | 0.24 | 0.15 | 0.37 | 0.21 | 0.06 | 0.01 |
| BUV661 | 0.06 | 0.1 | 0.1 | 1 | 0.37 | 0.1 | 0.03 | 0.03 | 0.03 | 0.09 | 0.06 | 0.1 | 0.08 | 0.09 | 0.2 | 0.42 | 0.27 |
| BUV737 | 0.04 | 0.02 | 0.02 | 0.37 | 1 | 0.39 | 0.01 | 0.01 | 0.01 | 0.03 | 0.01 | 0.03 | 0.02 | 0.02 | 0.06 | 0.15 | 0.43 |
| BUV805 | 0.07 | 0.04 | 0.02 | 0.1 | 0.39 | 1 | 0.01 | 0.01 | 0.01 | 0.06 | 0.01 | 0.02 | 0.01 | 0.01 | 0.02 | 0.04 | 0.11 |
| BV421 | 0.07 | 0.11 | 0.03 | 0.03 | 0.01 | 0.01 | 1 | 0.96 | 0.96 | 0.29 | 0.31 | 0.21 | 0.1 | 0.18 | 0.08 | 0.12 | 0.11 |
| Super Bright 436 | 0.07 | 0.14 | 0.03 | 0.03 | 0.01 | 0.01 | 0.96 | 1 | 0.94 | 0.31 | 0.37 | 0.25 | 0.11 | 0.17 | 0.07 | 0.11 | 0.09 |
| eFluor 450 | 0.03 | 0.12 | 0.02 | 0.03 | 0.01 | 0.01 | 0.96 | 0.94 | 1 | 0.25 | 0.48 | 0.29 | 0.13 | 0.15 | 0.06 | 0.1 | 0.08 |
| LIVE DEAD Blue | 0.53 | 0.51 | 0.07 | 0.09 | 0.03 | 0.06 | 0.29 | 0.31 | 0.25 | 1 | 0.18 | 0.16 | 0.01 | 0.02 | 0.01 | 0.05 | 0.04 |
| BV480 | 0.04 | 0.39 | 0.08 | 0.06 | 0.01 | 0.01 | 0.31 | 0.37 | 0.48 | 0.18 | 1 | 0.84 | 0.57 | 0.25 | 0.14 | 0.09 | 0.03 |
| BV510 | 0.05 | 0.5 | 0.24 | 0.1 | 0.03 | 0.02 | 0.21 | 0.25 | 0.29 | 0.16 | 0.84 | 1 | 0.88 | 0.53 | 0.38 | 0.2 | 0.07 |
| Pacific Orange | 0.01 | 0.22 | 0.15 | 0.08 | 0.02 | 0.01 | 0.1 | 0.11 | 0.13 | 0.01 | 0.57 | 0.88 | 1 | 0.75 | 0.58 | 0.28 | 0.07 |
| BV570 | 0.01 | 0.1 | 0.37 | 0.09 | 0.02 | 0.01 | 0.18 | 0.17 | 0.15 | 0.02 | 0.25 | 0.53 | 0.75 | 1 | 0.87 | 0.26 | 0.06 |
| BV605 | 0.01 | 0.06 | 0.21 | 0.2 | 0.06 | 0.02 | 0.08 | 0.07 | 0.06 | 0.01 | 0.14 | 0.38 | 0.58 | 0.87 | 1 | 0.57 | 0.17 |
| BV650 | 0.02 | 0.06 | 0.06 | 0.42 | 0.15 | 0.04 | 0.12 | 0.11 | 0.1 | 0.05 | 0.09 | 0.2 | 0.28 | 0.26 | 0.57 | 1 | 0.45 |
| BV711 | 0.01 | 0.03 | 0.01 | 0.27 | 0.43 | 0.11 | 0.11 | 0.09 | 0.08 | 0.04 | 0.03 | 0.07 | 0.07 | 0.06 | 0.17 | 0.45 | 1 |

FIG. 18-2

| BV750 | BV785 | Qdot 800 | BB515 | FITC | CF514 | CF568 | PE | PE-Dazzle594 | PE-Cy5 | PerCP | PerCP-Cy5.5 | PerCP-eFluor 710 | PE-Cy7 | APC | Alexa Fluor 647 | APC-R700 | APC-eFluor 780 |
|---|---|---|---|---|---|---|---|---|---|---|---|---|---|---|---|---|---|
| 0.01 | 0.01 | 0 | 0.03 | 0 | 0.01 | 0 | 0 | 0 | 0 | 0 | 0.02 | 0 | 0 | 0 | 0.01 | 0.01 | 0 |
| 0.03 | 0.01 | 0.01 | 0.15 | 0.1 | 0.13 | 0.01 | 0.03 | 0.01 | 0.01 | 0.01 | 0.05 | 0.01 | 0.01 | 0 | 0.04 | 0.03 | 0 |
| 0.02 | 0 | 0.01 | 0.08 | 0.08 | 0.17 | 0.41 | 0.48 | 0.24 | 0.06 | 0.04 | 0.05 | 0.02 | 0.01 | 0.02 | 0.02 | 0.02 | 0 |
| 0.09 | 0.05 | 0.14 | 0.03 | 0.02 | 0.04 | 0.07 | 0.05 | 0.17 | 0.46 | 0.45 | 0.41 | 0.3 | 0.05 | [illegible] | 0.74 | 0.53 | 0.15 |
| 0.39 | 0.24 | [illegible] | 0.01 | 0 | 0.01 | 0.01 | 0.01 | 0.02 | 0.12 | 0.19 | 0.35 | 0.4 | 0.14 | 0.25 | 0.24 | 0.49 | 0.34 |
| 0.15 | 0.22 | 0.54 | 0.01 | 0 | 0.01 | 0 | 0 | 0.01 | 0.01 | 0.03 | 0.07 | 0.07 | 0.08 | 0.03 | 0.03 | 0.06 | 0.25 |
| 0.05 | 0.08 | 0.01 | 0.03 | 0.02 | 0.17 | 0 | 0.01 | 0.01 | 0.01 | 0.01 | 0.02 | 0.01 | 0 | 0 | 0.01 | 0.02 | 0 |
| 0.04 | 0.06 | 0 | 0.03 | 0.01 | 0.17 | 0 | 0.01 | 0 | 0 | 0 | 0.01 | 0 | 0.01 | 0 | 0.01 | 0.01 | 0 |
| 0.04 | 0.06 | 0 | 0.02 | 0.01 | 0.17 | 0 | 0.01 | 0 | 0 | 0 | 0.01 | 0 | 0.01 | 0 | 0.01 | 0.01 | 0 |
| 0.01 | 0.03 | 0.01 | 0.06 | 0.01 | 0.04 | 0 | 0 | 0 | 0.01 | 0.01 | 0.04 | 0.01 | 0.01 | 0.01 | 0.04 | 0.04 | 0 |
| 0.01 | 0.01 | 0.01 | 0.1 | 0.09 | 0.28 | 0.02 | 0.05 | 0.02 | 0.01 | 0.01 | 0.03 | 0.01 | 0.01 | 0 | 0.02 | 0.03 | 0.01 |
| 0.01 | 0.03 | 0.03 | 0.08 | 0.07 | 0.37 | 0.04 | 0.11 | 0.06 | 0.02 | 0.04 | 0.07 | 0.04 | 0.01 | 0.01 | 0.03 | 0.04 | 0 |
| 0.02 | 0.02 | 0.03 | 0.05 | 0.05 | 0.38 | 0.06 | 0.15 | 0.1 | 0.02 | 0.04 | 0.07 | 0.04 | 0.01 | 0.02 | 0.02 | 0.04 | 0 |
| 0.01 | 0.02 | 0.02 | 0.03 | 0.03 | 0.27 | 0.44 | 0.54 | 0.32 | 0.09 | 0.08 | 0.08 | 0.05 | 0.01 | 0.04 | 0.02 | 0.04 | 0 |
| 0.09 | 0.06 | 0.08 | 0.02 | 0.02 | 0.17 | 0.32 | 0.27 | 0.5 | 0.23 | 0.21 | 0.2 | 0.16 | 0.03 | 0.14 | 0.04 | 0.08 | 0.01 |
| 0.23 | 0.15 | 0.17 | 0.02 | 0.02 | 0.09 | 0.07 | 0.06 | 0.19 | 0.3 | 0.38 | 0.38 | 0.32 | 0.04 | 0.37 | 0.19 | 0.2 | 0.06 |
| [illegible] | 0.48 | 0.47 | 0 | 0 | 0.02 | 0.01 | 0.01 | 0.04 | 0.15 | 0.23 | 0.53 | [illegible] | 0.1 | 0.24 | 0.2 | 0.43 | 0.19 |

| | | | | | | | | | | | | | | | | | | |
|---|---|---|---|---|---|---|---|---|---|---|---|---|---|---|---|---|---|---|
| BV750 | 0.01 | 0.03 | 0.02 | 0.09 | 0.39 | 0.15 | 0.05 | 0.04 | 0.04 | 0.01 | 0.01 | 0.01 | 0.02 | 0.01 | 0.09 | 0.23 | [illegible] | 1 |
| BV785 | 0.01 | 0.01 | 0 | 0.05 | 0.24 | 0.22 | 0.08 | 0.06 | 0.06 | 0.03 | 0.01 | 0.03 | 0.02 | 0.02 | 0.06 | 0.15 | 0.48 | [illegible] |
| Qdot 800 | 0 | 0.01 | 0.01 | 0.14 | 0.52 | 0.53 | 0.01 | 0 | 0 | 0.01 | 0.01 | 0.03 | 0.03 | 0.02 | 0.08 | 0.17 | 0.47 | [illegible] |
| BB515 | 0.03 | 0.15 | 0.09 | 0.03 | 0.01 | 0.01 | 0.03 | 0.03 | 0.02 | 0.06 | 0.1 | 0.08 | 0.05 | 0.03 | 0.02 | 0.02 | 0 | 0.01 |
| FITC | 0 | 0.1 | 0.08 | 0.02 | 0 | 0 | 0.02 | 0.01 | 0.01 | 0.01 | 0.09 | 0.07 | 0.05 | 0.03 | 0.02 | 0.02 | 0 | 0.01 |
| CF514 | 0.01 | 0.13 | 0.17 | 0.04 | 0.01 | 0.01 | 0.17 | 0.17 | 0.17 | 0.04 | 0.28 | 0.37 | 0.38 | 0.27 | 0.17 | 0.09 | 0.02 | 0 |
| CF568 | 0 | 0.01 | 0.41 | 0.07 | 0.01 | 0 | 0 | 0 | 0 | 0 | 0.02 | 0.04 | 0.06 | 0.44 | 0.32 | 0.07 | 0.01 | 0 |
| PE | 0 | 0.03 | 0.46 | 0.05 | 0.01 | 0 | 0.01 | 0.01 | 0.01 | 0 | 0.05 | 0.11 | 0.15 | 0.54 | 0.27 | 0.06 | 0.01 | 0.01 |
| PE-Dazzle594 | 0 | 0.01 | 0.24 | 0.17 | 0.02 | 0.01 | 0.01 | 0 | 0 | 0 | 0.02 | 0.06 | 0.1 | 0.32 | 0.5 | 0.19 | 0.04 | 0.01 |
| PE-Cy5 | 0 | 0.01 | 0.06 | 0.46 | 0.12 | 0.01 | 0.01 | 0 | 0 | 0.01 | 0.01 | 0.02 | 0.02 | 0.09 | 0.23 | 0.3 | 0.15 | 0.04 |
| PerCP | 0 | 0.01 | 0.04 | 0.45 | 0.18 | 0.03 | 0.01 | 0 | 0 | 0.01 | 0.01 | 0.04 | 0.04 | 0.08 | 0.21 | 0.38 | 0.23 | 0.12 |
| PerCP-Cy5.5 | 0.02 | 0.05 | 0.05 | 0.41 | 0.35 | 0.07 | 0.02 | 0.01 | 0.01 | 0.04 | 0.03 | 0.07 | 0.07 | 0.08 | 0.2 | 0.38 | 0.53 | 0.29 |
| PerCP-eFluor 710 | 0 | 0.01 | 0.02 | 0.3 | 0.4 | 0.07 | 0.01 | 0 | 0 | 0.01 | 0.01 | 0.04 | 0.04 | 0.05 | 0.16 | 0.32 | 0.63 | 0.36 |
| PE-Cy7 | 0 | 0.01 | 0.01 | 0.05 | 0.14 | 0.08 | 0 | 0.01 | 0.01 | 0.01 | 0.01 | 0.01 | 0.01 | 0.01 | 0.03 | 0.04 | 0.1 | 0.13 |
| APC | 0 | 0 | 0.02 | 0.81 | 0.25 | 0.03 | 0 | 0 | 0 | 0.01 | 0 | 0.01 | 0.02 | 0.04 | 0.14 | 0.37 | 0.24 | 0.07 |
| Alexa Fluor 647 | 0.01 | 0.04 | 0.02 | 0.74 | 0.24 | 0.03 | 0.01 | 0.01 | 0.01 | 0.04 | 0.02 | 0.03 | 0.02 | 0.02 | 0.04 | 0.19 | 0.2 | 0.03 |
| APC-R700 | 0.01 | 0.03 | 0.02 | 0.53 | 0.49 | 0.06 | 0.02 | 0.01 | 0.01 | 0.04 | 0.03 | 0.04 | 0.04 | 0.04 | 0.08 | 0.2 | 0.43 | 0.13 |
| APC-eFluor 780 | 0 | 0 | 0 | 0.15 | 0.34 | 0.25 | 0 | 0 | 0 | 0 | 0.01 | 0 | 0 | 0 | 0.01 | 0.06 | 0.19 | 0.18 |

Complexity Index: 46.43

FIG. 18-3

| Laser (nm) | Primary Detector | Fluorochrome | Emission Max (nm) |
|---|---|---|---|
| 405 | V1 | Brilliant Violet 421™ | 421 |
| | V2 | Alexa Fluor® 405 | 405 |
| | | Super Bright 436 | 436 |
| | V3 | eFluor® 450 | 450 |
| | | BD Horizon™ V450 | 450 |
| | | VioBlue® | 452 |
| | | Pacific Blue™ | 455 |
| | V4 | BD Horizon™ BV480 | 480 |
| | V5 | eFluor® 506 | 510 |
| | V7 | Brilliant Violet 510™ | 510 |
| | | BD Horizon™ V500 | 510 |
| | | VioGreen™ | 520 |
| | V8 | Pacific Orange™ | 550 |
| | | Brilliant Violet 570™ | 570 |
| | V10 | Super Bright 600 | 600 |
| | | Brilliant Violet 605™ | 605 |
| | | Qdot® 605 | 605 |
| | V11 | Super Bright 645 | 645 |
| | | Brilliant Violet 650™ | 650 |
| | | Qdot® 655 | 655 |
| | V13 | Super Bright 702 | 702 |
| | | Qdot® 705 | 705 |
| | | Brilliant Violet™ 711 | 711 |
| | V14 | Brilliant Violet 750™ | 750 |
| | V15 | Brilliant Violet 785™ | 785 |
| | | BD Horizon™ BV786 | 786 |
| | | Qdot® 800 | 790 |

| Laser (nm) | Primary Detector | Fluorochrome | Emission Max (nm) |
|---|---|---|---|
| 488 | B2 | Vio®515 | 514 |
| | | sVio®515 | 514 |
| | | BD Horizon™ BB515 | 515 |
| | | Alexa Fluor® 488 | 520 |
| | | FITC | 520 |
| | | VioBright™ FITC | 522 |
| | B3 | Alexa Fluor® 532 | 550 |
| | B8 | PerCP | 680 |
| | B9 | PerCP-Cy™5.5 | 680 |
| | | BD Horizon™ BB700 | 695 |
| | B10 | PerCP-Vio® 700 | 704 |
| | | PerCP-eFluor® 710 | 730 |

FIG. 22A

| Laser (nm) | Primary Detector | Fluorochrome | Emission Max (nm) |
|---|---|---|---|
| 561 | YG1 | PE | 576 |
| | YG3 | PE/Dazzle™ 594 | 610 |
| | | BD Horizon™ PE-CF594 | 610 |
| | | PE-eFluor® 610 | 610 |
| | | PE-Texas Red® | 625 |
| | | PE-Alexa Fluor® 610 | 630 |
| | YG5 | PE-Cy™5 | 668 |
| | YG7 | PE-Cy™5.5 | 680 |
| | | PE-Alexa Fluor® 700 | 720 |
| | YG9 | PE-Vio® 770 | 775 |
| | | PE-Cy™7 | 780 |
| 640 | R1 | APC | 660 |
| | R2 | eFluor® 660 | 660 |
| | | Alexa Fluor® 647 | 668 |
| | | Vio® 667 | 668 |
| | | sVio® 667 | 668 |
| | R4 | BD Horizon™ APC-R700 | 705 |
| | | Alexa Fluor® 700 | 720 |
| | R7 | APC-Cy™5.5 | 680 |
| | | APC-Vio® 770 | 775 |
| | | APC/Fire™ 750 | 780 |
| | | APC-Cy™7 | 780 |
| | | APC-eFluor® 780 | 780 |
| | | BD™ APC-H7 | 780 |
| | | APC-Alexa Fluor® 750 | 785 |

| Laser (nm) | Primary Detector | Fluorochrome | Emission Max (nm) |
|---|---|---|---|
| | **UV2** | **BD Horizon™ BUV395** | |
| | UV2 | CELLTRACE BLUE | |
| | UV6 | ALEXA FLUOR 350 | |
| | UV6 | CELLTRACE CALCEIN BLUE, AM | |
| | UV6 | DYLIGHT 350 | |
| | UV6 | EFLUOR 455 | |
| | UV6 | GHOST DYE UV 450 | |
| | UV6 | LIVE/DEAD™ Blue | |
| 355 | UV7 | BD Horizon™ BUV496 | |
| | UV7 | DAPI | |
| | UV7 | HOECHST 33342 | |
| | UV7 | ZOMBIE UV | |
| | UV9 | BD Horizon™ BUV563 | |
| | UV10 | BD Horizon™ BUV615 | |
| | UV11 | BD Horizon™ BUV661 | |
| | UV14 | BD Horizon™ BUV737 | |
| | UV15, UV16 | BD Horizon™ BUV805 | |

FIG. 22B

905

Similarity Indices

904

| | | | | | | | |
|---|---|---|---|---|---|---|---|
| Alexa Fluor 546 | 1 | | | | | | |
| APC/Fire 810 | 0 | 1 | | | | | |
| DAPI | 0.06 | 0.02 | 1 | | | | |
| LIVE DEAD Yellow | 0.24 | 0.03 | 0.49 | 1 | | | |
| NucView 488 | 0.4 | 0 | 0.01 | 0.03 | 1 | | |
| Qdot 800 | 0 | 0.35 | 0.01 | 0.02 | 0.01 | 1 | |
| R718 | 0.12 | 0.34 | 0.28 | 0.31 | 0.11 | 0.22 | 1 |
| 907 | Alexa Fluor 546 | APC/Fire 810 | DAPI | LIVE DEAD Yellow | NucView 488 | Qdot 800 | R718 |
| Complexity Index: 2.73 | | | | | | | |

907

906

Chart of similarity Indexes and complexity index for first set of selected Fluorochromes and first flow cytometer configuration. Shown on a display device by computer. Generated by the Similarity and Complexity Button

FIG. 23B

Pull down menu of Flow Cytometer Configuration Options

Chart of similarity Indexes and complexity index for set of selected Fluorochromes and second flow cytometer options. Shown on a display device by computer. Generated by the Similarity and Complexity Button Similarity Indices

| | Alexa Fluor 546 | APC/Fire 810 | DAPI | LIVE DEAD Yellow | NucView 488 | Qdot 800 | R718 |
|---|---|---|---|---|---|---|---|
| Alexa Fluor 546 | 1 | | | | | | |
| APC/Fire 810 | 0 | 1 | | | | | |
| DAPI | 0.01 | 0.02 | 1 | | | | |
| LIVE DEAD Yellow | 0.02 | 0.03 | 0.27 | 1 | | | |
| NucView 488 | 0.03 | 0 | 0.01 | 0.03 | 1 | | |
| Qdot 800 | 0 | 0.37 | 0.01 | 0.01 | 0.01 | 1 | |
| R718 | 0.03 | 0.29 | 0.61 | 0.28 | 0.09 | 0.18 | 1 |

Complexity Index: 2.81

FIG. 24C

Similarity Indices

| | | | | | | | | | | | | |
|---|---|---|---|---|---|---|---|---|---|---|---|---|
| Alexa Fluor 546 | 1 | | | | | | | | | | | |
| APC/Fire 810 | 0 | 1 | | | | | | | | | | |
| DAPI | 0.01 | 0.02 | 1 | | | | | | | | | |
| LIVE DEAD Yellow | 0.02 | 0.03 | 0.27 | 1 | | | | | | | | |
| NucView 488 | 0.03 | 0 | 0.01 | 0.03 | 1 | | | | | | | |
| Qdot 800 | 0 | 0.37 | 0.01 | 0.01 | 0.01 | 1 | | | | | | |
| R718 | 0.03 | 0.29 | 0.61 | 0.28 | 0.09 | 0.18 | 1 | | | | | |
| Zombie Green | 0.01 | 0 | 0.01 | 0.01 | 0.85 | 0 | 0.09 | 1 | | | | |
| Zombie Yellow | 0.02 | 0.03 | 0.16 | 0.93 | 0.04 | 0.05 | 0.24 | 0.02 | 1 | | | |
| violetFluor 450 | 0 | 0.02 | 0.44 | 0.14 | 0 | 0 | 0.16 | 0 | 0.07 | 1 | | |
| Alexa Fluor 555 | 0.8 | 0.02 | 0.46 | 0.37 | 0.23 | 0.02 | 0.37 | 0.18 | 0.32 | 0.12 | 1 | |
| Alexa Fluor 660 | 0.02 | 0.19 | 0 | 0 | 0 | 0.12 | 0.61 | 0 | 0.01 | 0 | 0.03 | 1 |

904

FIG. 27B-1

905

FIG. 27B-2

905

904

| | | | | | | | | | | | | | | | | | | | | | | | | |
|---|---|---|---|---|---|---|---|---|---|---|---|---|---|---|---|---|---|---|---|---|---|---|---|---|
| BUV496 | 0.01 | 0.02 | 0.88 | 0.21 | 0.04 | 0 | 0.58 | 0.07 | 0.11 | 0.11 | 0.46 | 0 | 1 | | | | | | | | | | | |
| CF700 | 0 | 0.34 | 0 | 0.01 | 0 | 0.18 | 0.76 | 0 | 0.01 | 0 | 0.01 | 0.8 | 0 | 1 | | | | | | | | | | |
| CFSE | 0.01 | 0 | 0.02 | 0.03 | 0.83 | 0 | 0.09 | 1 | 0.03 | 0.01 | 0.19 | 0 | 0.07 | 0 | 1 | | | | | | | | | |
| eFluor 506 | 0.01 | 0.02 | 0.34 | 0.74 | 0.09 | 0.01 | 0.26 | 0.1 | 0.48 | 0.26 | 0.34 | 0 | 0.27 | 0 | 0.12 | 1 | | | | | | | | |
| Ghost Dye Violet 540 | 0.02 | 0.03 | 0.31 | 0.98 | 0.04 | 0.01 | 0.29 | 0.02 | 0.84 | 0.19 | 0.39 | 0 | 0.24 | 0 | 0.04 | 0.84 | 1 | | | | | | | |
| Live-or-Dye 510/550 | 0.04 | 0.01 | 0.08 | 0.33 | 0.91 | 0.01 | 0.16 | 0.67 | 0.3 | 0.04 | 0.33 | 0 | 0.09 | 0 | 0.65 | 0.3 | 0.34 | 1 | | | | | | |
| PE-Alexa Fluor 610 | 0.29 | 0.04 | 0 | 0.07 | 0.08 | 0.08 | 0.1 | 0.02 | 0.12 | 0 | 0.36 | 0.22 | 0 | 0.05 | 0.02 | 0.01 | 0.06 | 0.1 | 1 | | | | | |
| Qdot 655 | 0.04 | 0.02 | 0.03 | 0.19 | 0.04 | 0.01 | 0.1 | 0.01 | 0.32 | 0 | 0.14 | 0.05 | 0.02 | 0.01 | 0.01 | 0.03 | 0.15 | 0.08 | 0.43 | 1 | | | | |
| PerCP-eFluor 710 | 0.02 | 0.14 | 0 | 0.04 | 0.03 | 0.42 | 0.34 | 0 | 0.08 | 0 | 0.06 | 0.45 | 0 | 0.38 | 0.01 | 0 | 0.02 | 0.05 | 0.38 | 0.09 | 1 | | | |
| PE/Fire 780 | 0.02 | 0.21 | 0 | 0 | 0.01 | 0.59 | 0.08 | 0 | 0.01 | 0 | 0.03 | 0.1 | 0 | 0.07 | 0 | 0 | 0 | 0.01 | 0.11 | 0 | 0.29 | 1 | | |
| PE-Texas Red | 0.51 | 0.02 | 0.01 | 0.11 | 0.12 | 0.04 | 0.08 | 0.04 | 0.15 | 0 | 0.55 | 0.11 | 0.01 | 0.02 | 0.04 | 0.03 | 0.09 | 0.15 | 0.85 | 0.28 | 0.19 | 0.06 | 1 | |
| PerCP | 0.04 | 0.04 | 0.01 | 0.02 | 0.04 | 0.13 | 0.13 | 0 | 0.07 | 0.01 | 0.1 | 0.25 | 0.01 | 0.09 | 0 | 0.01 | 0.01 | 0.06 | 0.54 | 0.42 | 0.46 | 0.09 | 0.33 | 1 |

FIG. 27B-3

905

904

| | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|
| Qdot 705 | 0.03 | 0.11 | 0.01 | 0.07 | 0.03 | 0.42 | 0.31 | 0 | 0.15 | 0 | 0.06 | 0.4 | 0 | 0.31 | 0 | 0 | 0.05 | 0.05 | 0.4 | 0.28 | 0.86 | 0.2 | 0.21 | 0.58 | 1 | | | | | | | | | | | |
| TMRE | 0.97 | 0.01 | 0.01 | 0.05 | 0.03 | 0.01 | 0.04 | 0.01 | 0.06 | 0 | 0.79 | 0.04 | 0.01 | 0.01 | 0.01 | 0.02 | 0.05 | 0.05 | 0.42 | 0.09 | 0.05 | 0.03 | 0.64 | 0.09 | 0.06 | 1 | | | | | | | | | | |
| Zombie UV | 0 | 0.02 | 0.9 | 0.17 | 0.01 | 0.01 | 0.51 | 0.01 | 0.09 | 0.6 | 0.34 | 0 | 0.63 | 0 | 0.01 | 0.24 | 0.2 | 0.05 | 0.01 | 0.02 | 0.01 | 0 | 0.01 | 0 | 0.01 | 0.01 | 1 | | | | | | | | | |
| VioBright FITC | 0.02 | 0 | 0.02 | 0.05 | [illegible] | 0 | 0.1 | 0.98 | 0.05 | 0.01 | 0.21 | 0 | 0.07 | 0 | 0.98 | 0.13 | 0.06 | 0.78 | 0.04 | 0.01 | 0.01 | 0 | 0.06 | 0 | 0.01 | 0.02 | 0.02 | 1 | | | | | | | | |
| Super Bright 702 | 0.01 | 0.18 | 0.06 | 0.08 | 0 | 0.4 | 0.45 | 0 | 0.14 | 0.12 | 0.04 | 0.52 | 0.01 | 0.52 | 0 | 0.03 | 0.06 | 0.02 | 0.13 | 0.1 | 0.64 | 0.09 | 0.05 | 0.26 | 0.79 | 0.02 | 0.08 | 0 | 1 | | | | | | | |
| PE-Vio770 | 0.02 | 0.21 | 0 | 0 | 0.01 | 0.59 | 0.08 | 0 | 0.01 | 0 | 0.03 | 0.1 | 0 | 0.07 | 0 | 0 | 0 | 0.01 | 0.11 | 0 | 0.29 | 1 | 0.06 | 0.09 | 0.2 | 0.03 | 0 | 0 | 0.09 | 1 | | | | | | |
| mCherry | 0.48 | 0.03 | 0.01 | 0.03 | 0.03 | 0.05 | 0.06 | 0.01 | 0.05 | 0 | 0.46 | 0.16 | 0 | 0.03 | 0.01 | 0.01 | 0.03 | 0.04 | 0.86 | 0.24 | 0.2 | 0.1 | 0.92 | 0.32 | 0.23 | 0.65 | 0.01 | 0.02 | 0.06 | 0.1 | 1 | | | | | |
| Ghost Dye Blue 516 | 0.01 | 0 | 0.01 | 0.01 | 0.86 | 0 | 0.08 | 1 | 0.02 | 0 | 0.18 | 0 | 0.06 | 0 | 0.99 | 0.1 | 0.02 | 0.68 | 0.02 | 0.01 | 0 | 0 | 0.03 | 0 | 0 | 0.01 | 0.01 | 0.99 | 0 | 0 | 0.01 | 1 | | | | |
| CF750 | 0.01 | 0.7 | 0 | 0.01 | 0 | 0.43 | 0.35 | 0 | 0.01 | 0 | 0.01 | 0.24 | 0 | 0.44 | 0 | 0 | 0 | 0 | 0.02 | 0 | 0.18 | 0.24 | 0.01 | 0.04 | 0.16 | 0.01 | 0 | 0 | 0.25 | 0.23 | 0.02 | 0 | 1 | | | |
| BV570 | 0.37 | 0.02 | 0.17 | 0.75 | 0.05 | 0.02 | 0.22 | 0.02 | 0.85 | 0.15 | 0.55 | 0.02 | 0.09 | 0.01 | 0.03 | 0.28 | 0.65 | 0.24 | 0.22 | 0.21 | 0.05 | 0.01 | 0.32 | 0.06 | 0.09 | 0.4 | 0.14 | 0.04 | 0.08 | 0.01 | 0.23 | 0.02 | 0.01 | 1 | | |
| Alexa Fluor 350 | 0.01 | 0.02 | 0.86 | 0.18 | 0.04 | 0.06 | 0.55 | 0.04 | 0.15 | 0.16 | 0.37 | 0.01 | 0.69 | 0.01 | 0.04 | 0.15 | 0.18 | 0.08 | 0.03 | 0.07 | 0.05 | 0.02 | 0.04 | 0.05 | 0.08 | 0.01 | 0.87 | 0.05 | 0.08 | 0.02 | 0.02 | 0.04 | 0.02 | 0.14 | 1 | |
| 7AAD | 0.18 | 0.06 | 0 | 0.04 | 0.05 | 0.15 | 0.11 | 0.01 | 0.06 | 0 | 0.24 | 0.29 | 0 | 0.07 | 0.01 | 0.01 | 0.03 | 0.06 | 0.92 | 0.36 | 0.49 | 0.22 | 0.64 | 0.62 | 0.5 | 0.3 | 0.01 | 0.02 | 0.16 | 0.22 | 0.74 | 0.01 | 0.04 | 0.13 | 0.03 | 1 |

905

855C

Export Spectra Button

METHODS AND APPARATUS FOR A TWENTY-FIVE-COLOR FLUORESCENCE-BASED ASSAY AND FLOW CYTOMETRY PANEL

CROSS-REFERENCE TO RELATED APPLICATIONS

This United States (US) Non-Provisional Patent application claims the benefit of (US) Provisional Patent Application No. 63/336,010 titled METHODS AND APPARATUS FOR A TWENTY-FIVE-COLOR FLUORESCENCE-BASED ASSAY AND FLOW CYTOMETRY PANEL filed on Jun. 7, 2022 by inventors Maria Jaimes et al., incorporated herein by reference for all intents and purposes. Provisional Patent Application No. 63/336,010 claims the benefit of United States (US) Non-Provisional patent application Ser. No. 17/304,843 titled METHODS OF FORMING MULTI-COLOR FLUORESCENCE-BASED FLOW CYTOMETRY PANEL filed on Jun. 26, 2021 by inventors Maria Jaimes et al., incorporated herein by reference for all intents and purposes. (US) Non-Provisional patent application Ser. No. 17/304,843 claims the benefit of United States (US) Provisional Patent Application No. 63/045,040 titled METHODS OF FORMING MULTI-COLOR FLUORESCENCE-BASED FLOW CYTOMETRY PANEL filed on Jun. 26, 2020 by inventors Maria Jaimes et al., incorporated herein by reference for all intents and purposes. (US) Non-Provisional patent application Ser. No. 17/304,843 also claims the benefit of United States (US) Provisional Patent Application No. 63/045,103 titled METHODS OF FORMING MULTI-COLOR FLUORESCENCE-BASED FLOW CYTOMETRY PANEL filed on Jun. 27, 2020 by inventors Maria Jaimes et al., incorporated herein by reference for all intents and purposes.

This patent application is related to United States (US) patent application Ser. No. 15/659,610 titled COMPACT DETECTION MODULE FOR FLOW CYTOMETERS filed on Jul. 25, 2017 by inventors Ming Yan et al., incorporated herein by reference for all intents and purposes. This patent application is further related to U.S. patent application Ser. No. 15/498,397 titled COMPACT MULTI-COLOR FLOW CYTOMETER filed on Apr. 26, 2017 by David Vrane et al. that describes a flow cytometer with which the embodiments can be used and is incorporated herein by reference for all intents and purposes. This patent application is further related to U.S. patent application Ser. No. 16/418,942 titled FAST RECOMPENSATION OF FLOW CYTOMETERY DATA FOR SPILLOVER READJUSTMENTS filed on May 21, 2019 by Zhenyu Zhang that describes matrices with which the embodiments can be used and is incorporated herein by reference for all intents and purposes.

FIELD

The embodiments of the invention relate generally to fluorochrome and marker selection to analyze biological samples with a flow cytometer.

BACKGROUND

Flow cytometry is a technology that provides rapid analysis of physical and chemical characteristics of single cells in solution. Flow cytometers utilize lasers as light sources to produce both scattered and fluorescent light signals that are read by detectors such as photodiodes or photomultiplier tubes. Cell populations can be analyzed and/or purified based on their fluorescent or light scattering characteristics. Flow cytometry provides a method to identify cells in solution and is most commonly used for evaluating peripheral blood, bone marrow, and other body fluids.

Flow cytometry is generally used in the analysis of biological cells. Examples of biological cells include Astrocyte, Basophil, B Cell, Embryonic Stem Cell, Endothelial Cell, Eosinophil, Epithelial Cell, Erythrocyte, Fibroblast, Hematopoietic Stem Cell, Macrophage, Mast Cell, Myeloid-derived suppressor cells (MDSCs), Megakarocyte, Mesenchymal Stem Cell, Microglia, Monocyte, Myeloid Dendritic Cell, Naïve T Cell, Neurons, Neutrophil, NK Cell, Plasmacytoid Dendritic Cell, Platelets, Stromal Cells, T Follicular Helper, Th1, Th2, Th9, Th17, Th22, and Treg. Although flow cytometry was developed originally for analysis of relatively large mammalian cells, it is finding increased use by microbiologists.

The basic principle of flow cytometry is the passage of cells in single file in front of a laser so they can be detected, counted and sorted. A beam of laser light is directed at a hydrodynamically-focused stream of fluid that carries the cells. Several detectors are carefully placed around the stream, at the point where the fluid passes through the light beam. The stream of fluid is focused so that the cells pass through the laser light one at a time.

In hydrodynamic focusing, the sample fluid is enclosed by an outer sheath fluid and injected through a nozzle or cuvette. The nozzle or cuvette can be cone shaped causing a narrowing of the sheath and subsequent increase in the fluid velocity. The sample is introduced into the center and is focused by the Bernoulli effect. This allows the creation of a stream of particles in single file and is called. Under optimal conditions (laminar flow) there is no mixing of the central fluid stream and the sheath fluid.

Once the cells are lined up in a single file flow, they are passed through one or more lasers. One or more detectors are placed proximate the point where the fluid passes the laser beam. Those detector(s) in line with the light beam, and typically up to 20 degrees offset from the laser beam's axis, are used to measure Forward Scatter or FSC. This FSC measurement can give an estimation of a particle's size with larger particles refracting more light than smaller particles, but this can depend on several factors such as the sample, the wavelength of the laser, the collection angle and the refractive index of the sample and sheath fluid.

Other detector(s) are placed perpendicular to the stream and are used to measure Side Scatter (SSC). The SSC can provide information about the relative complexity (for example, granularity and internal structures) of a cell or particle; however as with forward scatter this can depend on various factors.

Both FSC and SSC are unique for every particle and a combination of the two may be used to roughly differentiate cell types in a heterogeneous population such as blood. However, this depends on the sample type and the quality of sample preparation, so fluorescent labeling is generally required to obtain more detailed information.

In modern flow cytometry, cells are fluorescently labelled and then excited by laser(s) to emit light at varying wavelengths. The fluorescence can then be measured to determine the amount and type of cells present in a sample. In preparation for flow cytometric analysis, single cells in suspension are fluorescently labeled, typically with a fluorescently conjugated monoclonal antibody. Antibodies are stained with a fluorophore (fluorochrome or dye) and introduced to the cell population, where they bind to cell markers.

Fluorophores are fluorescent markers used to detect the expression of cellular molecules such as proteins or nucleic acids. They accept light energy (for example, from a laser) at a given wavelength and re-emit it at a longer wavelength. These two processes are called excitation and emission. Emission follows excitation extremely rapidly, commonly in nanoseconds and is known as fluorescence.

When a fluorophore absorbs light, its electrons become excited and move from a resting state, to a maximal energy level called the excited electronic singlet state. The amount of energy required for this transition will differ for each fluorophore. The duration of the excited state depends on the fluorophore and typically lasts for 1-10 nanoseconds. The fluorophore then undergoes a conformational change, the electrons fall to a lower, more stable energy level called the electronic singlet state, and some of the absorbed energy is released as heat. The electrons subsequently fall back to their resting state releasing the remaining energy as fluorescence.

Cells express characteristic (proteins, lipids, glycosylation, etc.) that can be used to help distinguish unique cell types. These markers are referred to as cell markers that can be expressed both extracellularly on the cells surface (surface or extracellular cell marker) or as an intracellular molecule (intracellular cell marker). Markers are generally functional membrane proteins involved in cell communication, adhesion, or metabolism. Surface and intracellular cell markers can be used for a variety of cell types including immune cells, stem cells, central nervous system cells, and more.

Antibodies can specifically bind to cell markers. The affinity between the paratope region of antibodies and the corresponding epitope region of cell markers is a very useful way to identify a specific cell population. However, the cell markers will often be expressed on more than one cell type. Therefore, flow cytometry staining strategies have led to methods for immunophenotyping cells with two or more antibodies simultaneously.

CD markers (cluster of differentiation markers) are used for the identification and characterization of leukocytes and the different subpopulations of leukocytes. Many immunological cell markers are CD markers and these are commonly used for detection in flow cytometry of specific immune cell populations and subpopulations. The majority of flow cytometer analysis are conducted on leukocytes; however, the general principle of the invention is applicable to other bodily fluids.

The fluorescently labelled cell components are excited by the laser and emit light at a longer wavelength than the light source. The detectors therefore pick up a combination of scattered and fluorescent light. The intensity of the emitted light is directly proportional to the antigen density or the characteristics of the cell being measured. Data from the detectors can then analyzed by a computer using special software. The computer can be coupled in communication with the flow cytometer.

Fluorescence measurements taken at different wavelengths can provide quantitative and qualitative data about fluorophore-labeled cell surface receptors or intracellular molecules such as DNA and cytokines. Most flow cytometers use separate channels and detectors to detect emitted light, the number of which vary according to the instrument and the manufacturer.

The need to understand the mechanisms and pathways of immune evasion seen either post immunotherapy or during natural immune responses to cancer, autoimmunity, and infectious diseases, requires methods and protocols which will enable a deeper profiling of the immune system. Greater characterization of immune subpopulations allows for more informed decisions regarding the identification of targetable biomarkers and the development of new therapeutic approaches. Unraveling the complexity of the human immune response requires the ability to perform high throughput, in-depth analysis, at the single cell and population levels.

Sample availability can often be limited, especially in cases of clinical trial material, when multiple types of testing are required from a single sample or timepoint. Maximizing the amount of information that can be obtained from a single sample not only provides more in-depth characterization of the immune system, but also serves to address the issue of limited sample availability.

BRIEF SUMMARY

The embodiments of the invention are summarized by the claims that follow below.

BRIEF DESCRIPTIONS OF THE DRAWINGS

This patent or application file contains at least one drawing executed in color. Copies of this patent or patent application publication with color drawing(s) will be provided by the United States Patent and Trademark Office upon request and payment of the necessary fec.

FIGS. 6A-6D illustrate data from an exemplary 40-color panel.

FIG. 9 introduces a simple 3 detector and two fluorochrome example to show and describe how the similarity index for a pair of fluorochromes and the complexity index for a set of two fluorochromes are generated.

FIG. 10 illustrates two reference control vectors for two reference samples of two fluorochromes in continuing with the example introduced by FIG. 9.

Figure 11:
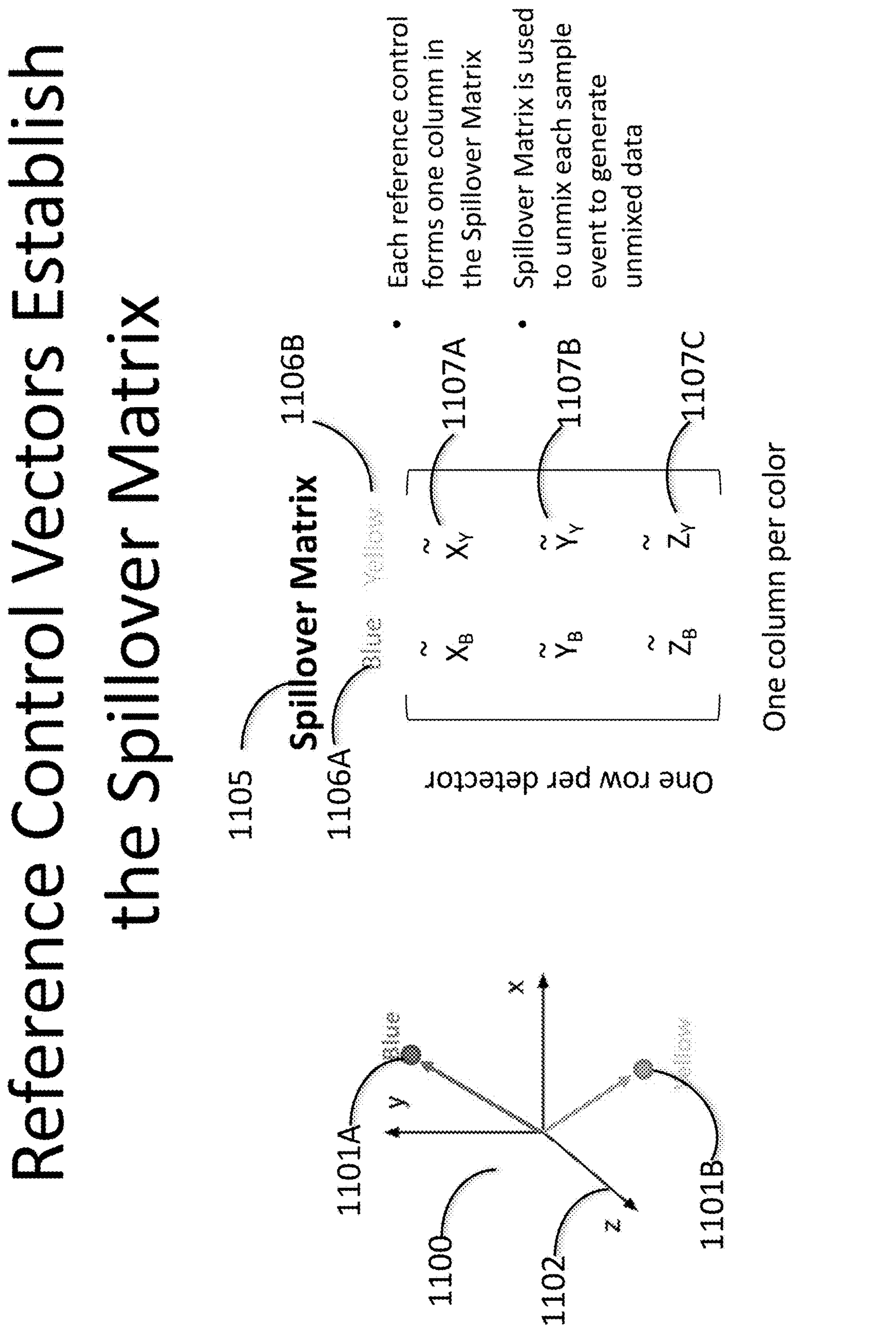

FIG. 11 illustrates a simple spillover matrix for the example introduced by FIG. 9.

FIG. 12 illustrates event vectors obtained by running a mixed sample through a flow cytometer for the two reference samples and two fluorochromes introduced by FIG. 9.

Figure 13:
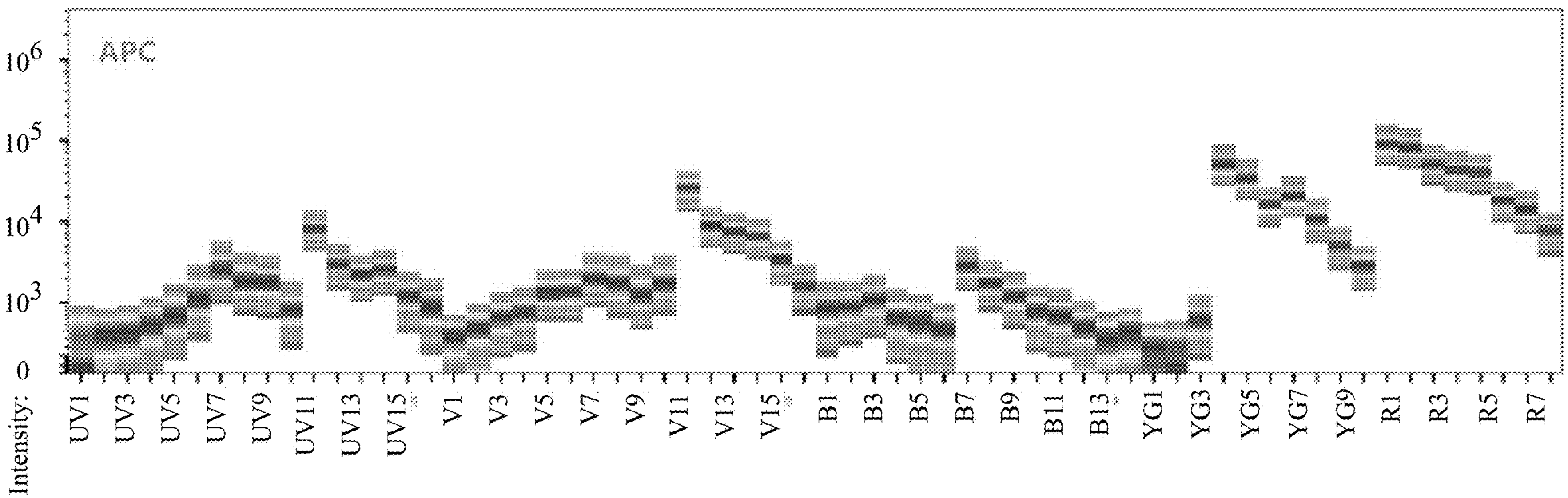

FIG. 13 illustrates a spectra signature obtained by a more complex flow cytometer with 64 detectors that generates a 64-dimension vector representing that spectral signature to contrast it with the simplified example.

Figure 14:
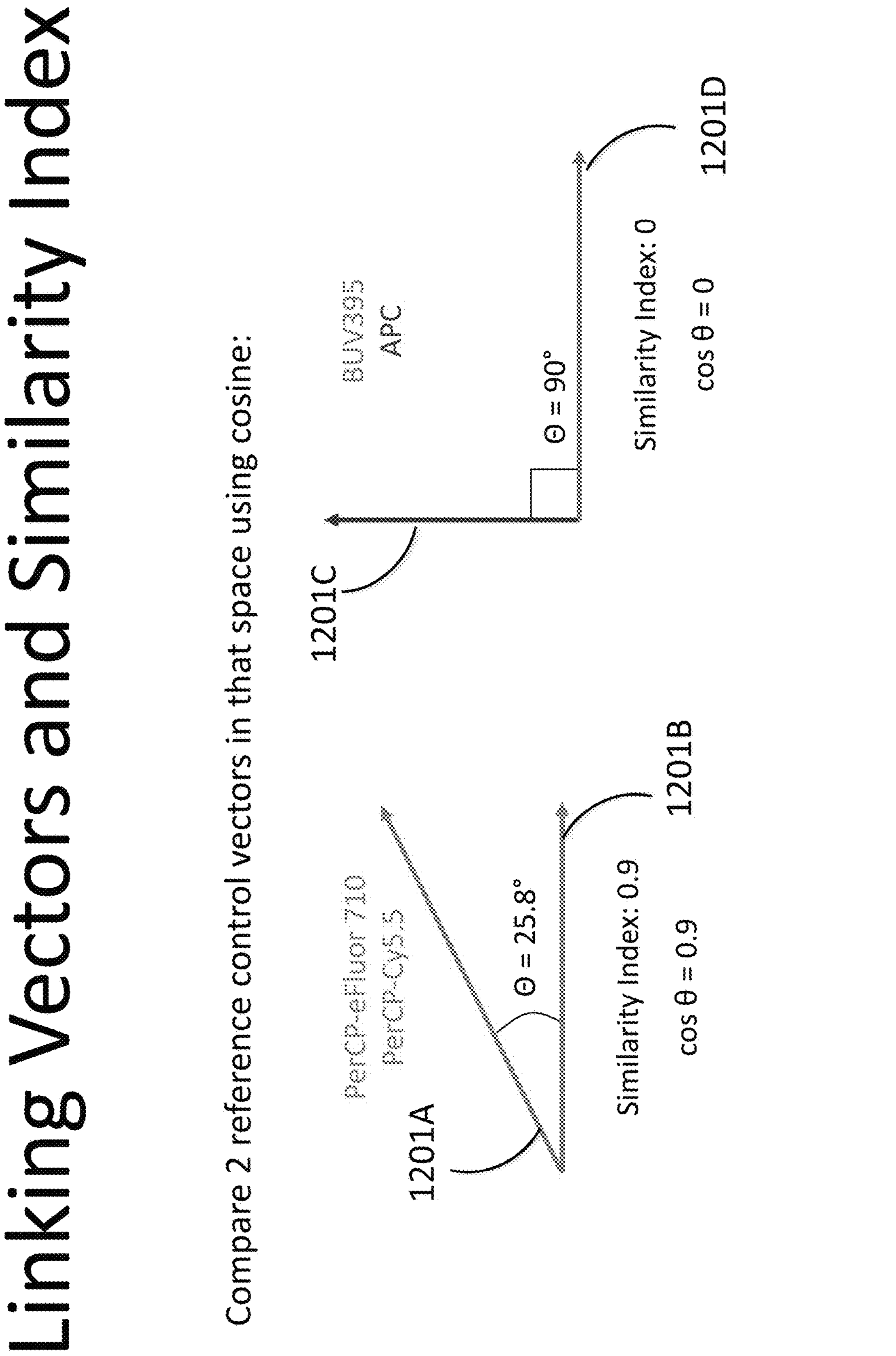

FIG. 14 illustrates a simple example of a similarity index and its association with the reference control vectors of two reference samples.

Figure 15:
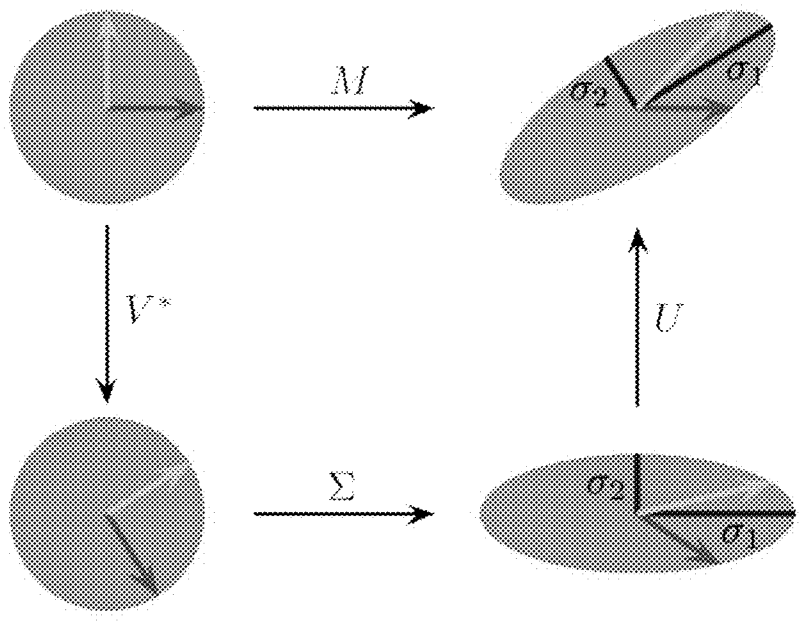
Figure 16:
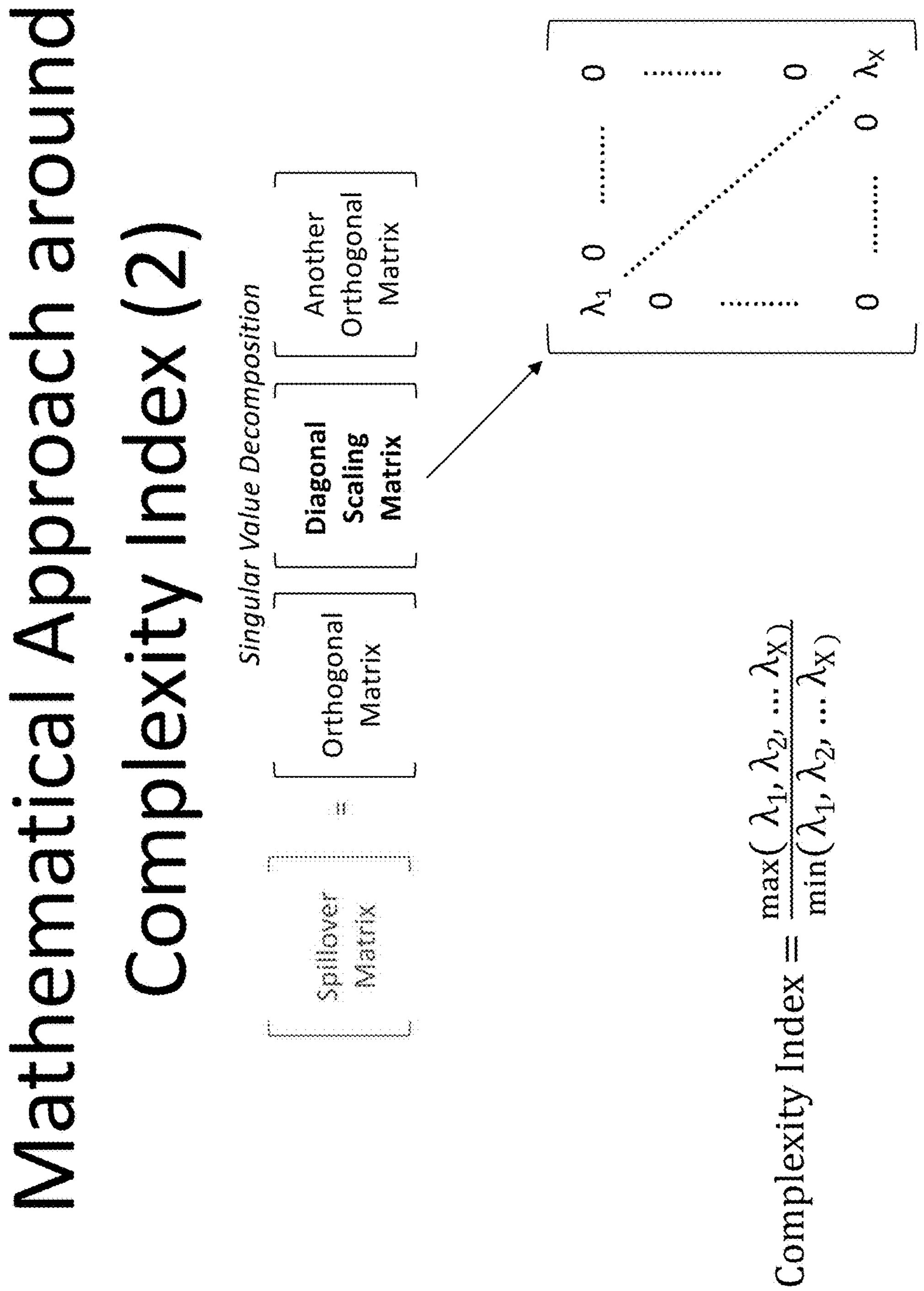

FIGS. 15-16 introduces the matrices and linear algebra that can be used to compute a complexity index.

Figure 17:
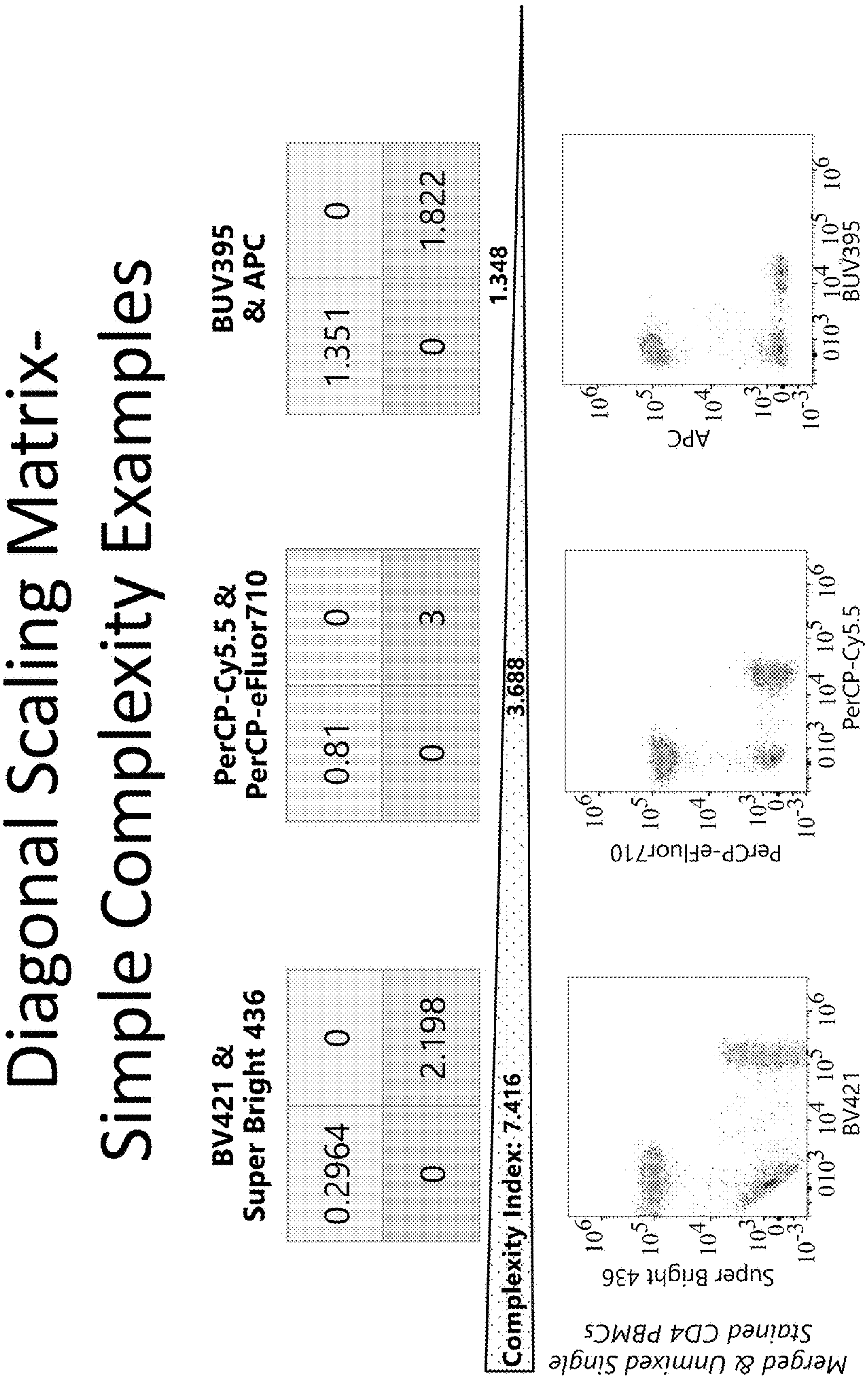

FIG. 17 illustrates three simple complexity examples with a set of two fluorochromes.

Figure 18:
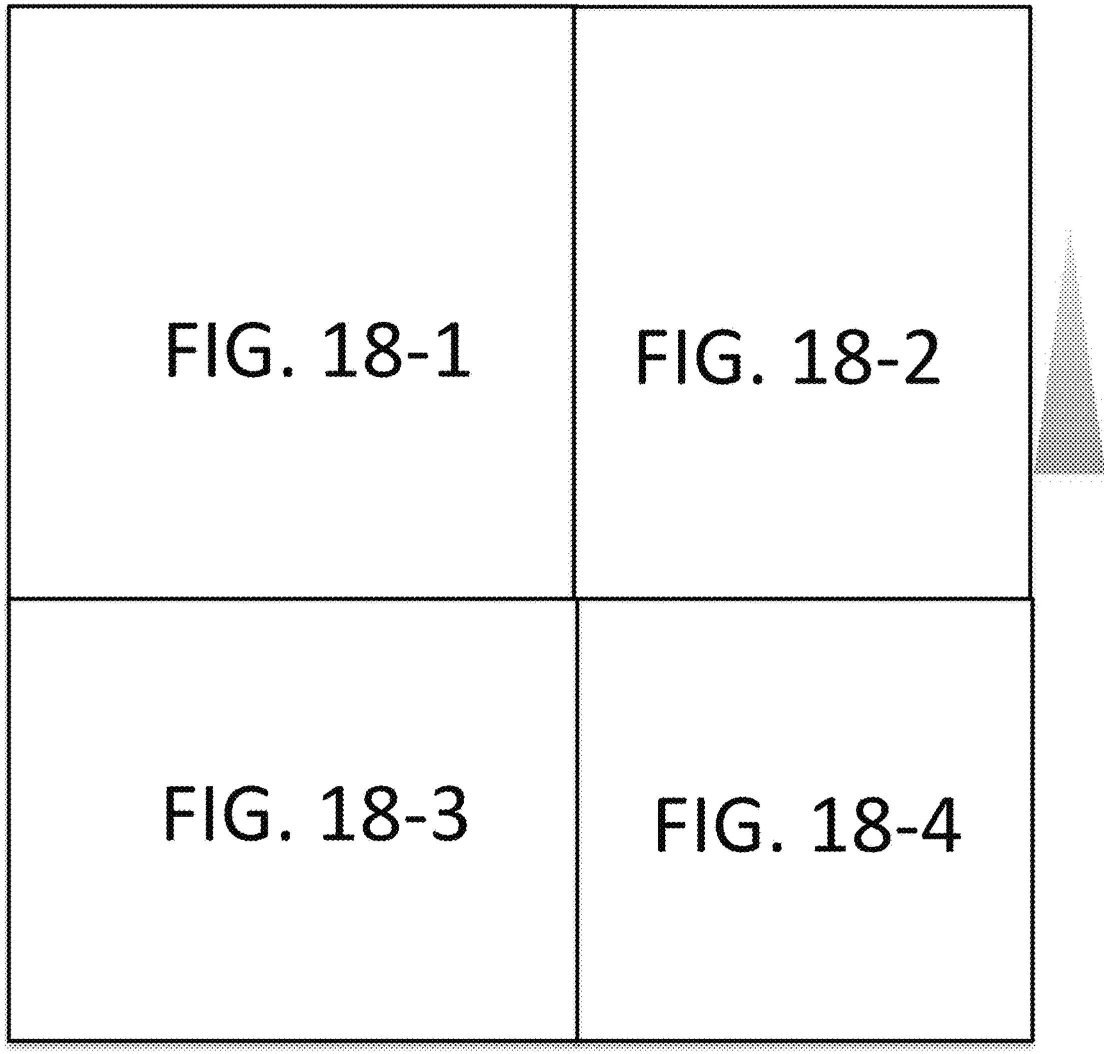
Figures 4, 18:
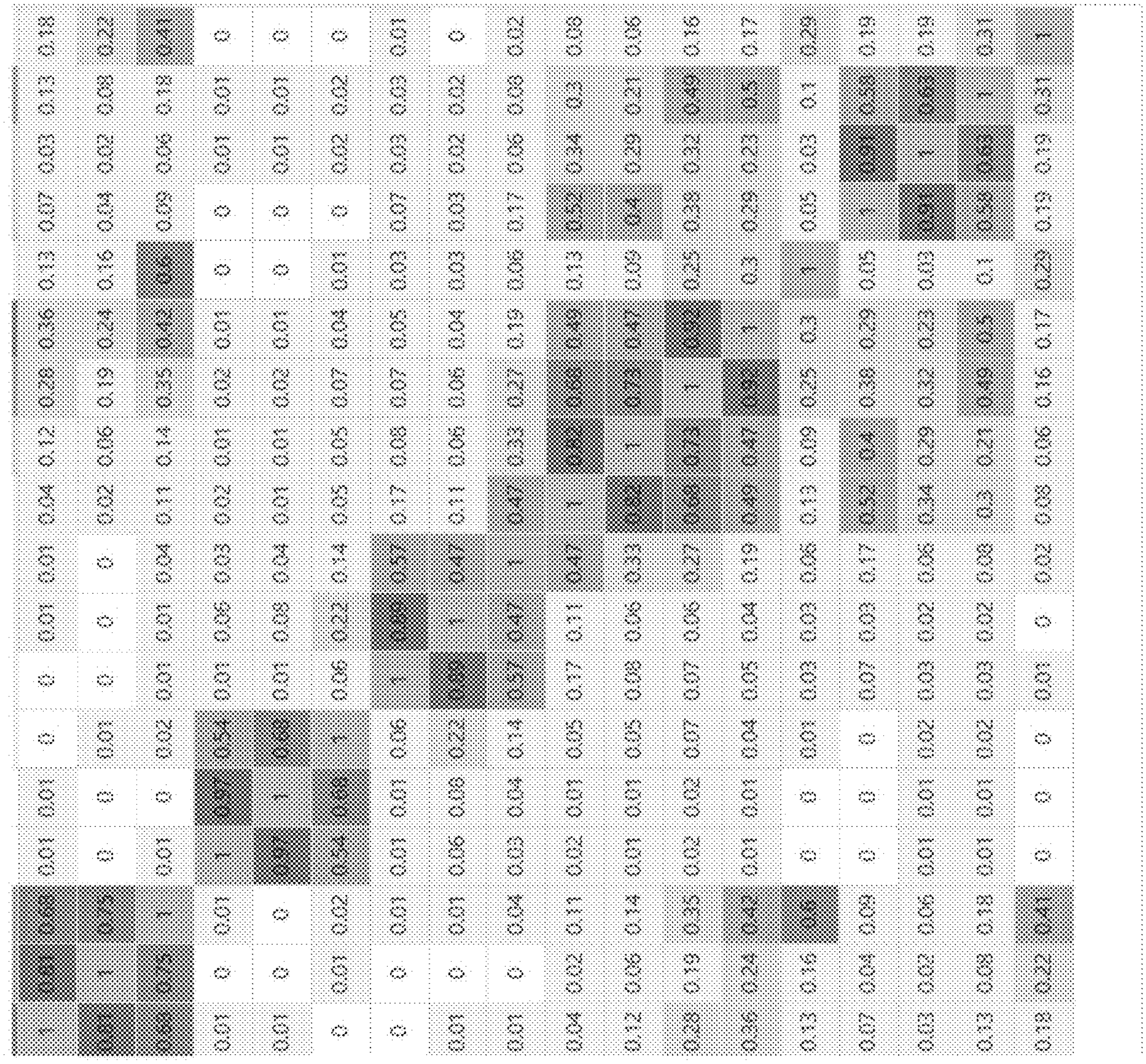

FIGS. 18 (18-1, 18-2, 18-3, and 18-4) illustrates a similarity matrix with similarity indexes and example computations of a complexity index for a 35 fluorochrome sample.

Figure 19:
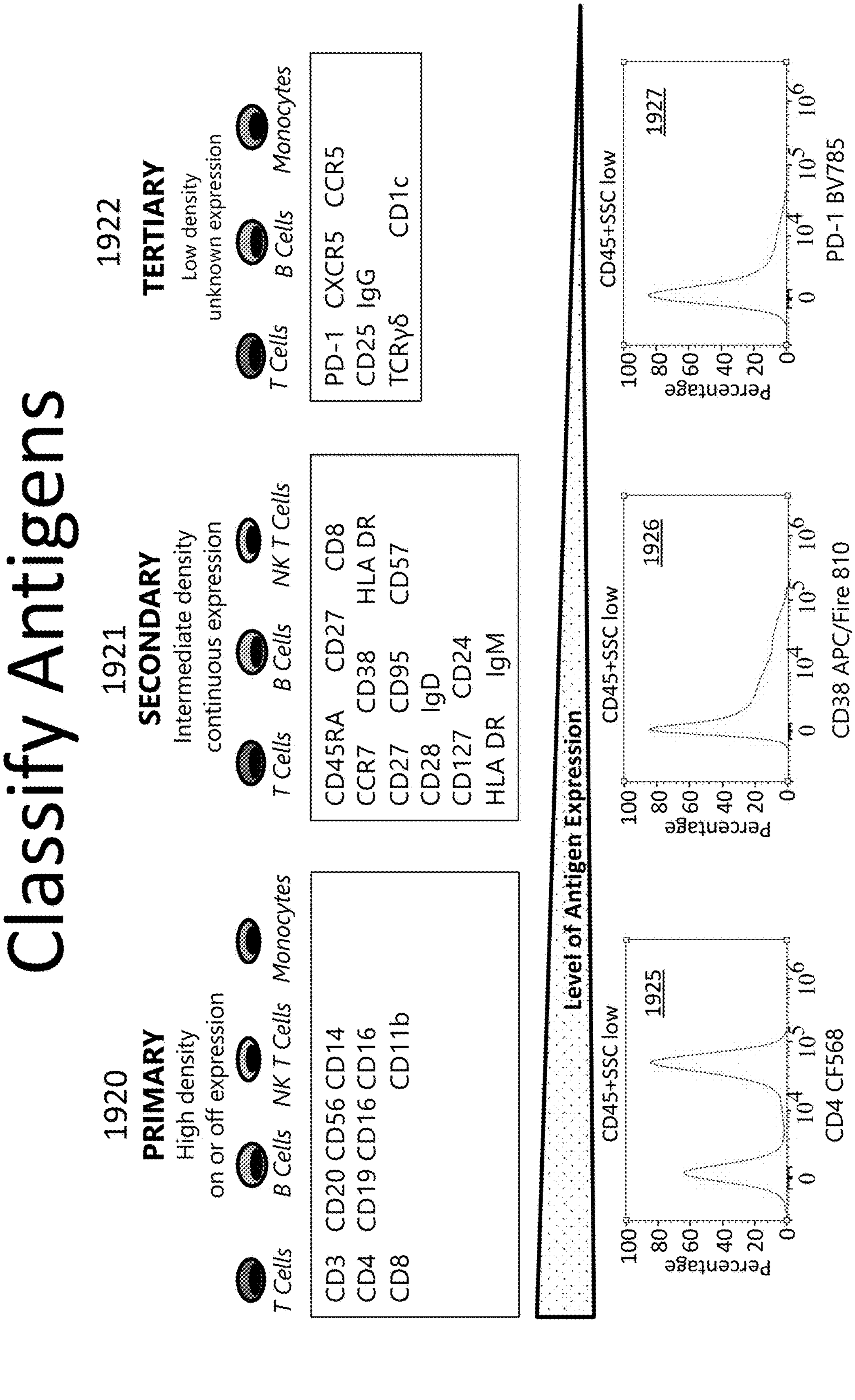

FIG. 19 is a chart illustrating a classification of antigens/cell markers that can affect the detected data.

Figure 20A:
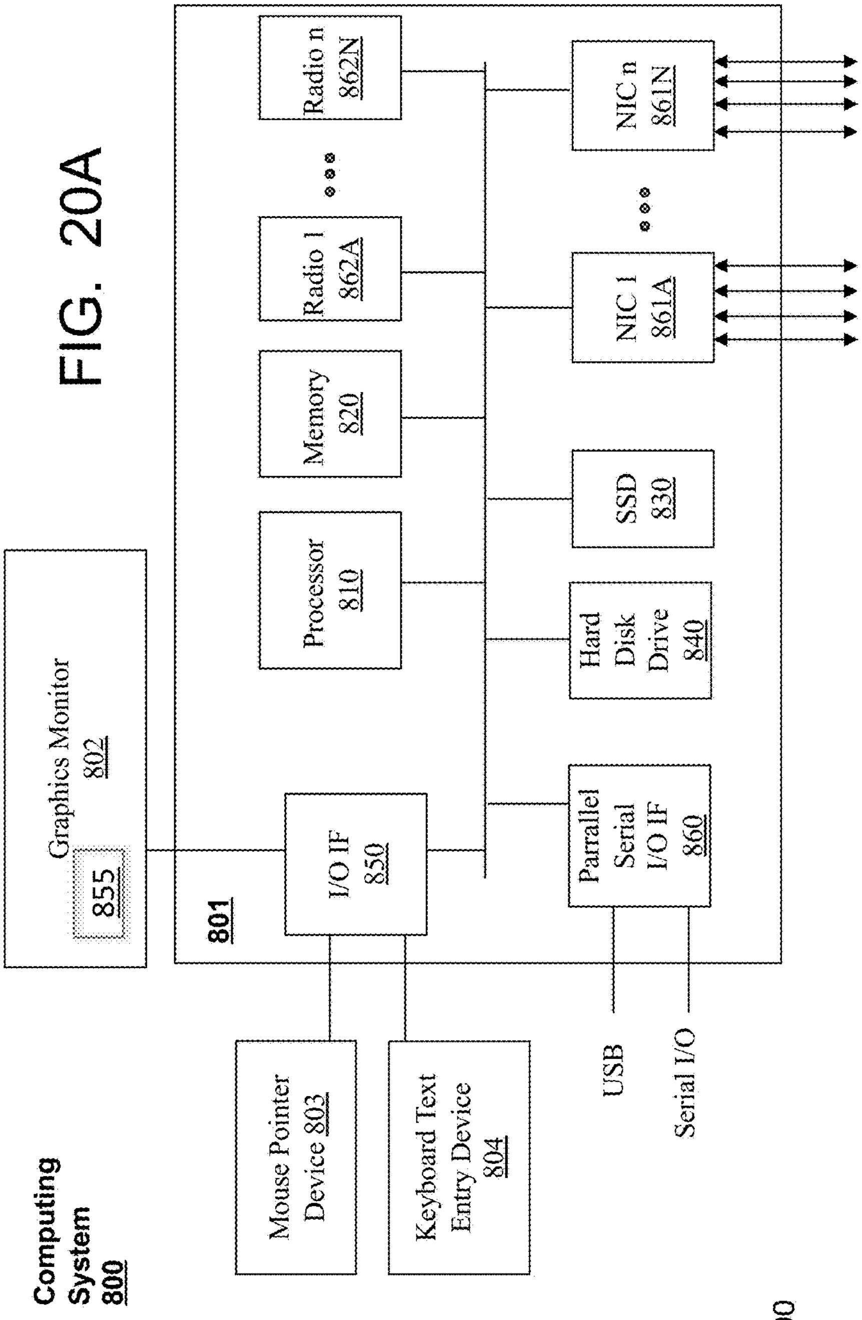
Figure 20B:
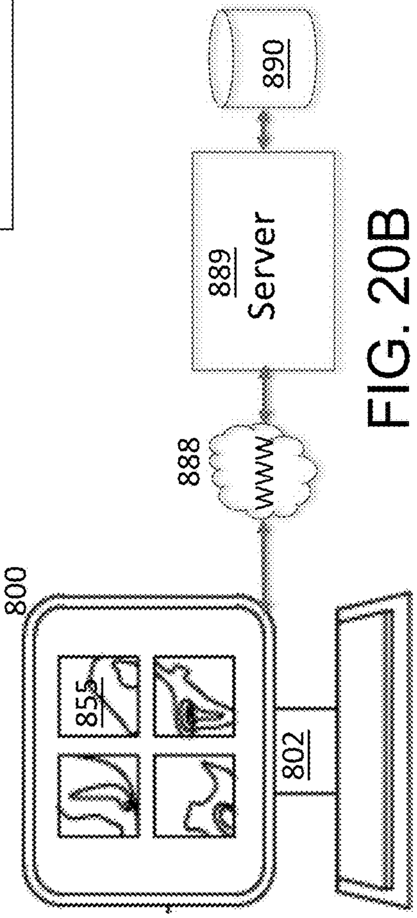

FIGS. 20A-20B are block diagrams of a computer system that can execute software instructions to display a graphical user interface and remotely interact with a web-based spectrum viewer software application.

Figure 21:
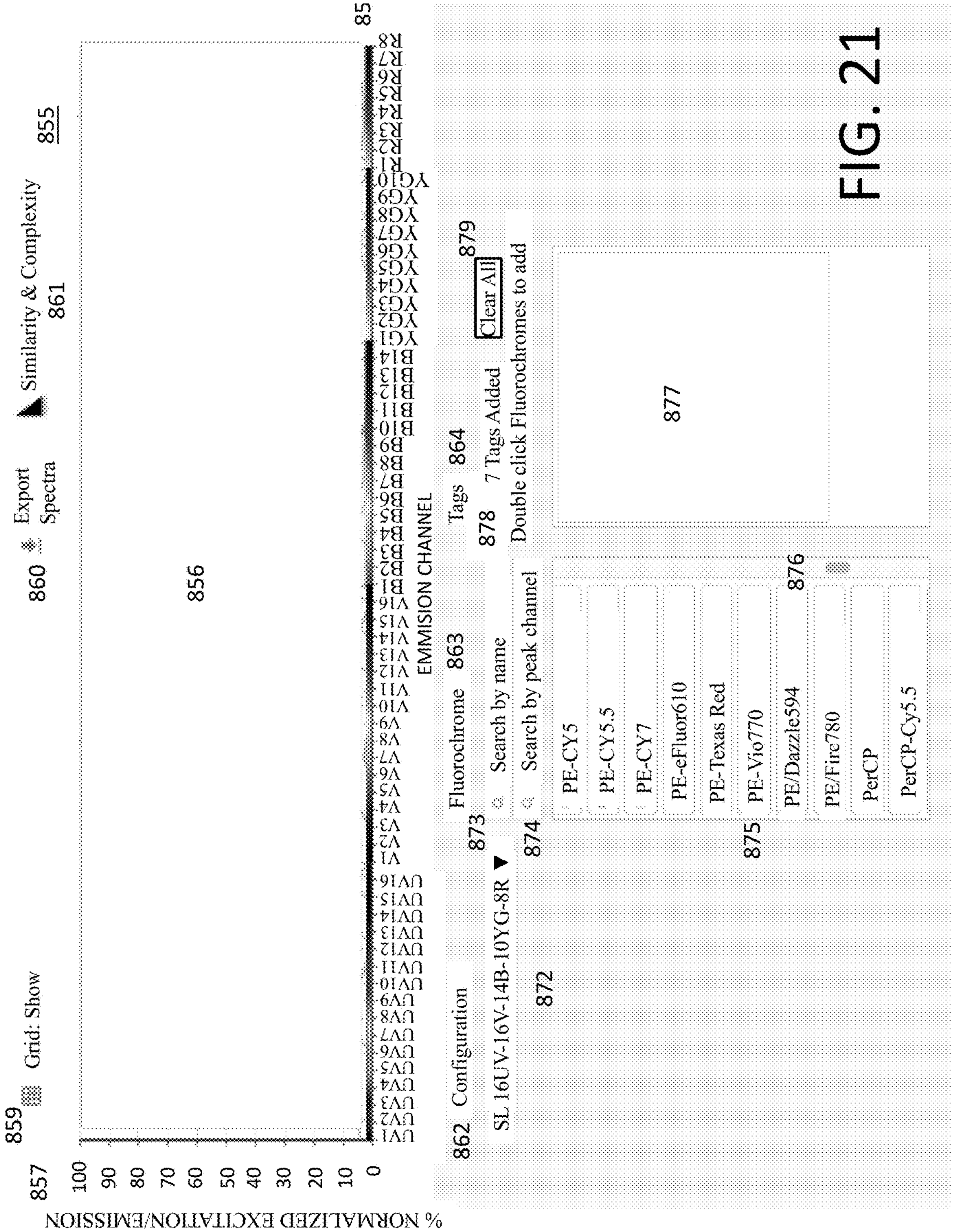

FIG. 21 illustrates a graphical user interface (GUI) generated by a spectrum viewer software application displayed on a monitor of a computer system.

FIGS. 22A-22B illustrate some of the fluorochromes that can be selected by the GUI.

Figure 23A:
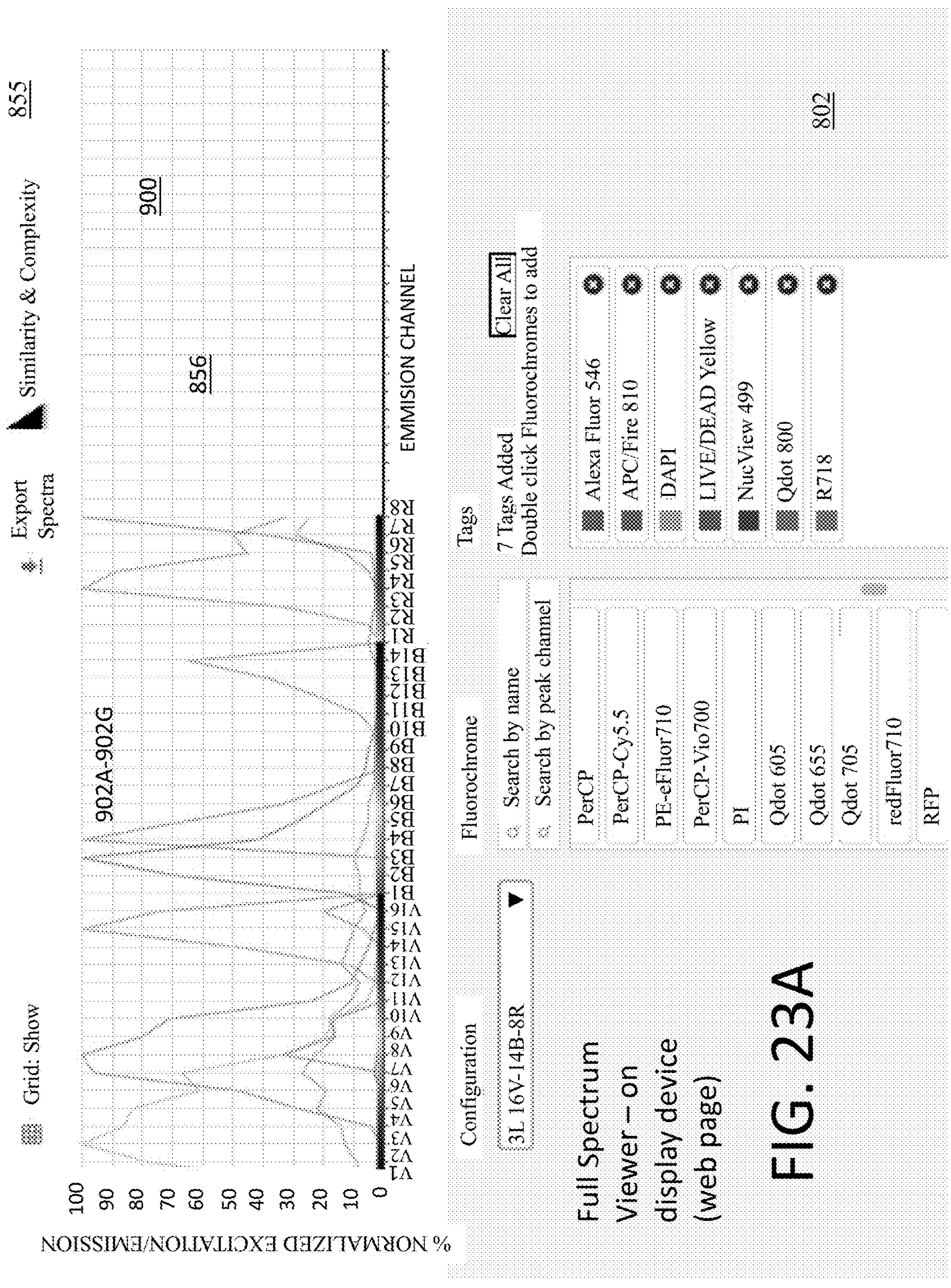

FIG. 23A illustrates an exemplary set of seven fluorochromes selected in the GUI and displayed by the monitor.

FIG. 23B illustrates a similarity/complexity chart of similarity indexes opened in a new GUI window associated with the seven fluorochromes selected in FIG. 23A.

Figure 24A:
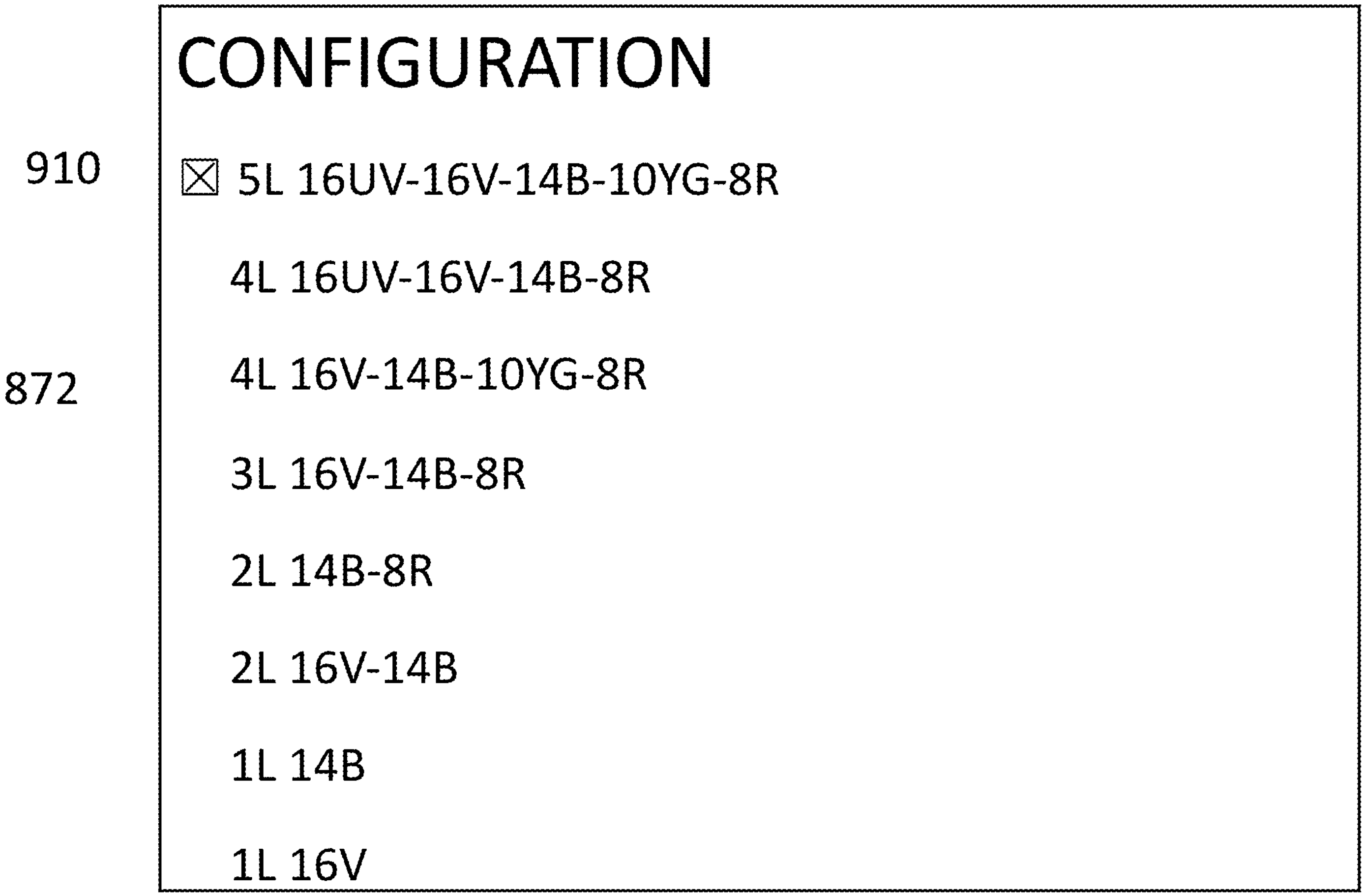

FIG. 24A illustrates a plurality of configurations 872 for the modular flow cytometer that are selectable by the pull-down menu 872.

Figure 24B:
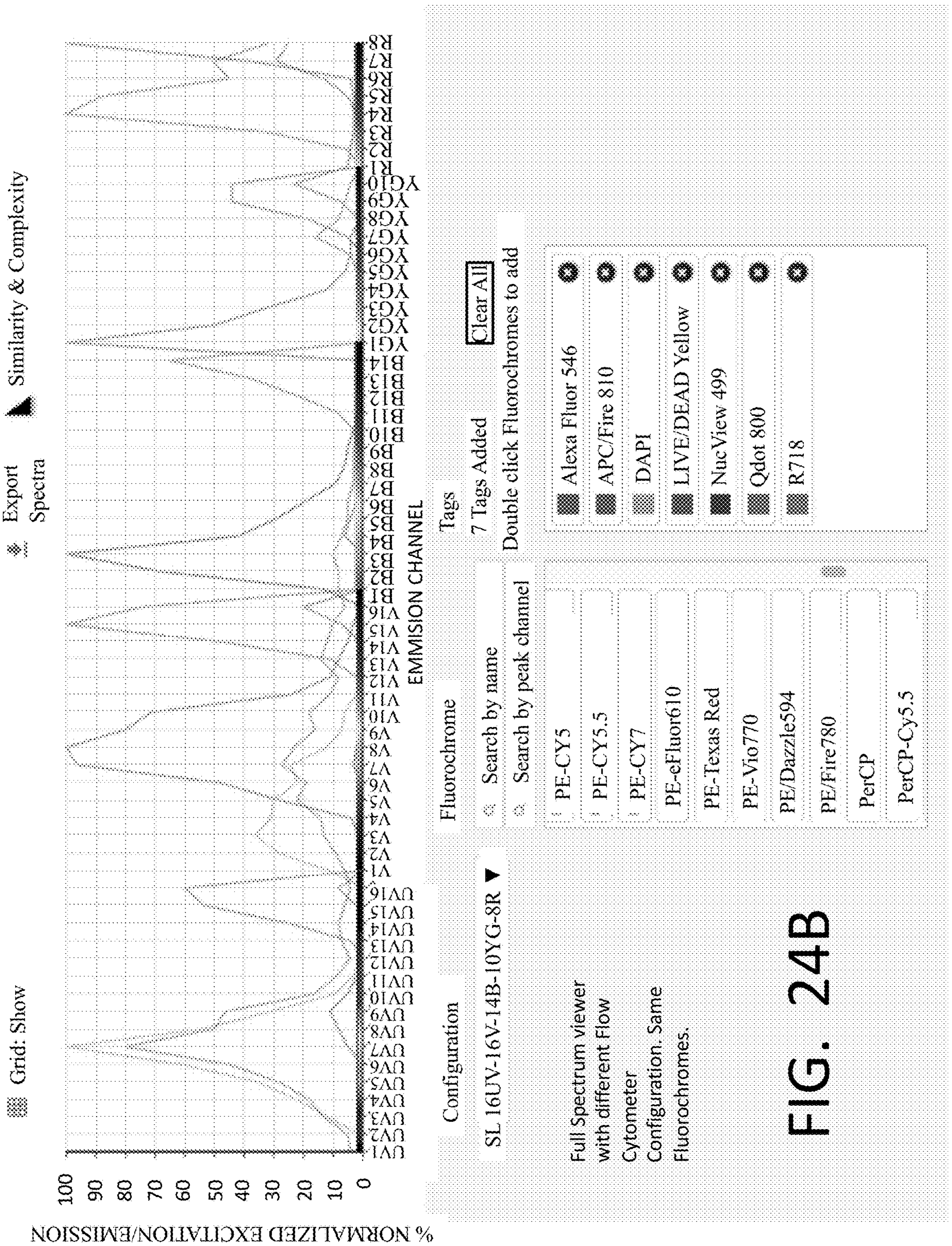

FIG. 24B illustrates the GUI with an improved flow cytometer configuration with the same seven selected fluorochromes selected in FIG. 23A.

FIG. 24C is an updated similarity/complexity chart for the improved flow cytometer configuration with the same seven selected fluorochromes selected in FIG. 23A.

Figure 25:
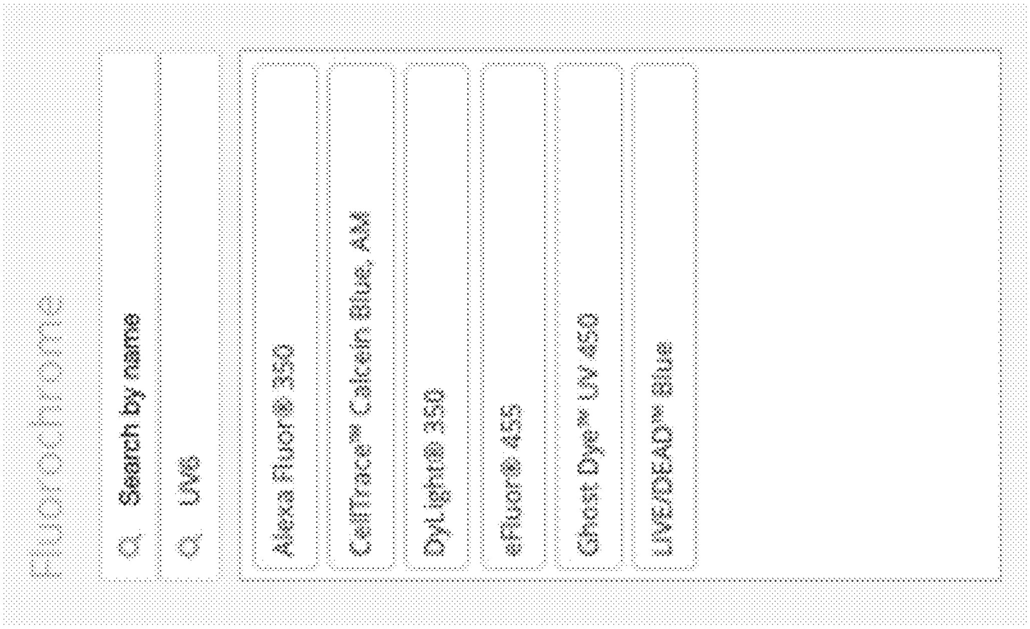

FIG. 25 illustrates searching for fluorochromes by name with an input field.

Figure 26:

FIG. 26 illustrates searching for fluorochromes by peak channel with an input field.

Figure 27A:
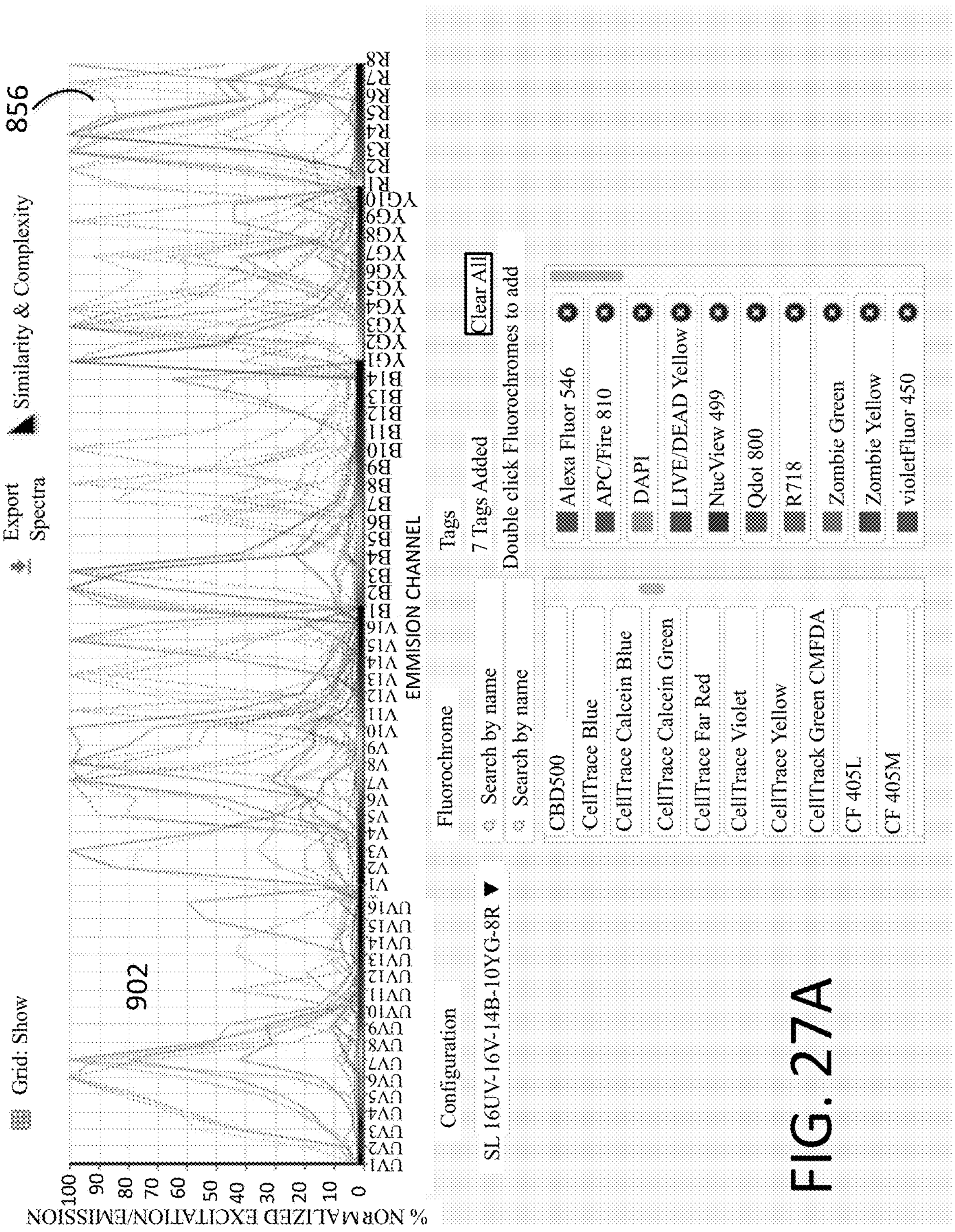

FIG. 27A illustrates a GUI with a selection of a large number of fluorochromes (e.g., 46 randomly) with a full spectrum configuration for the flow cytometer.

Figure 27B:
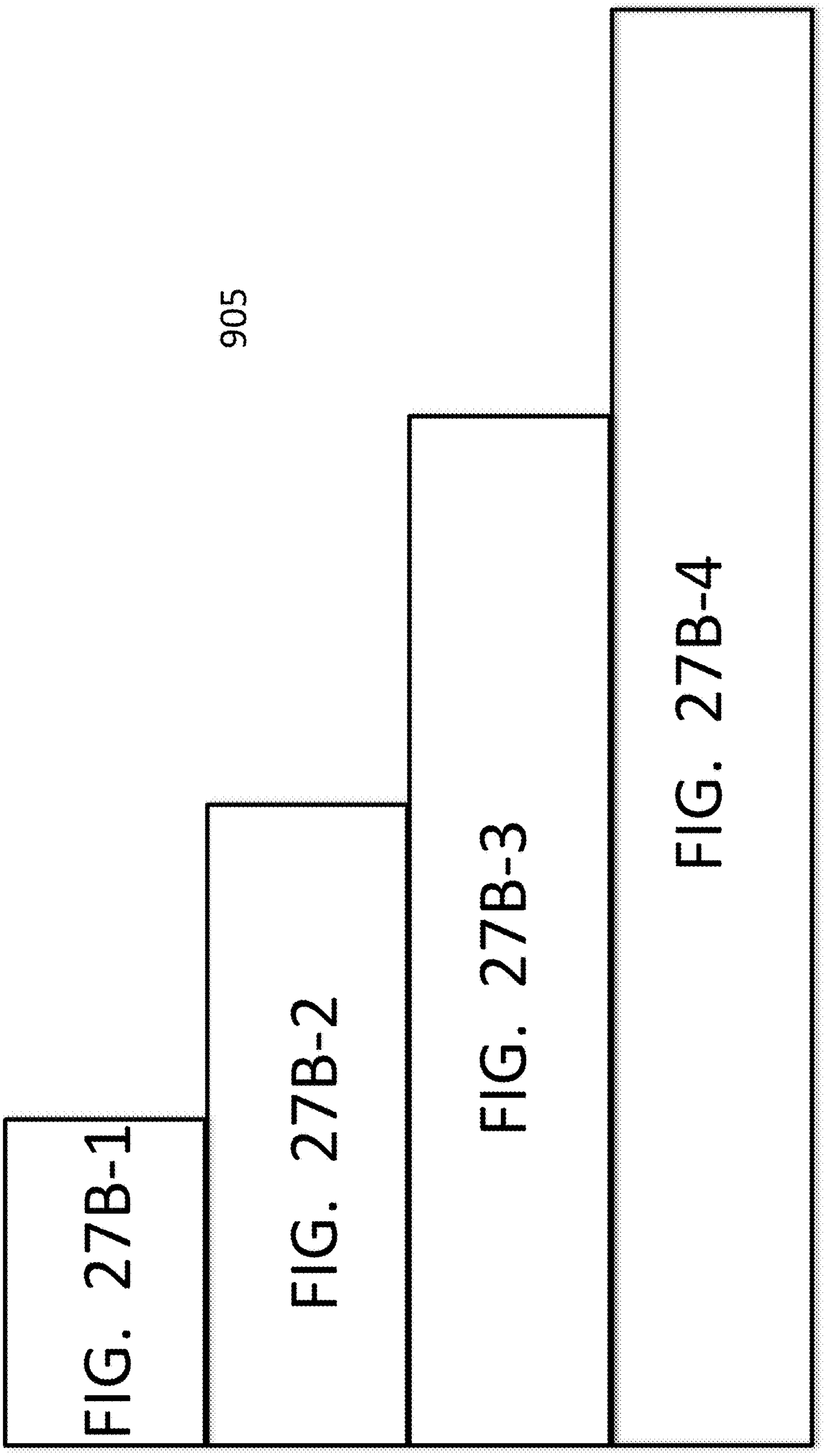
Figures 4, 27B:
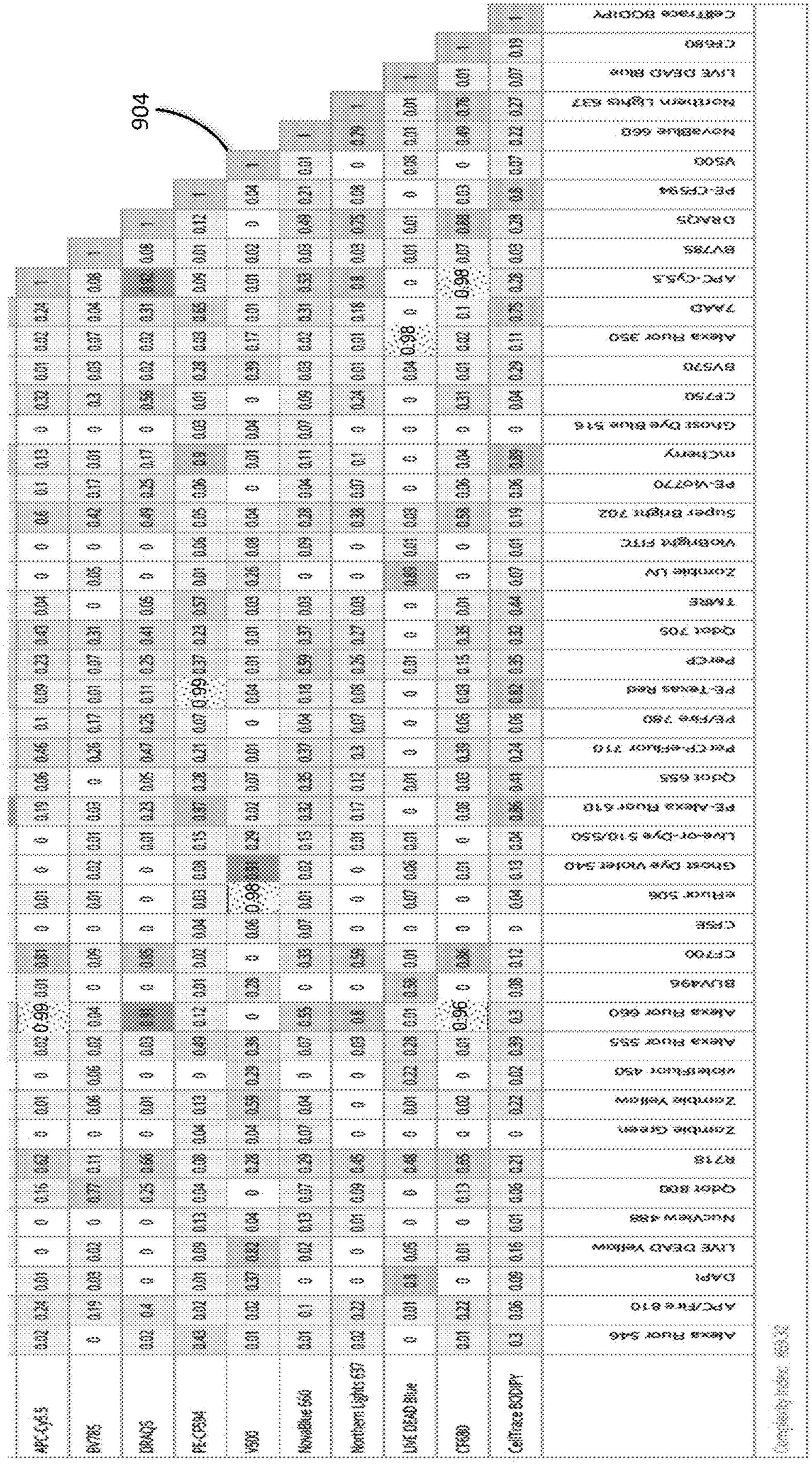

FIG. 27B (27B-1, 27B-2, 27B-3, and 27B-4) illustrates a GUI window with a similarity/complexity chart of similarity indexes for the large number of selected fluorochromes associated with FIG. 27A.

Figure 27C:
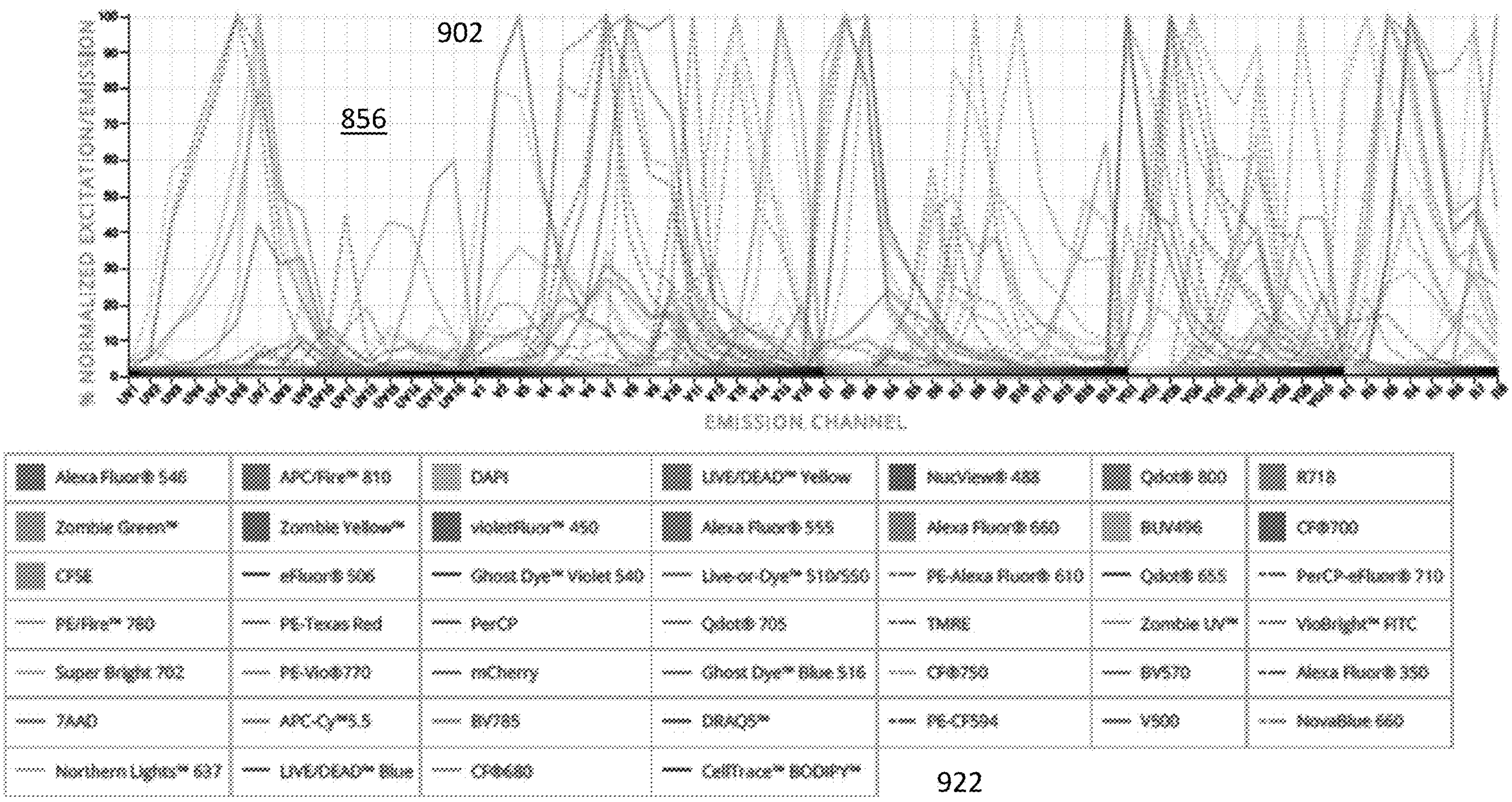

FIG. 27C illustrates a GUI window shown in response to a selection of the export spectra button.

Figure 28:
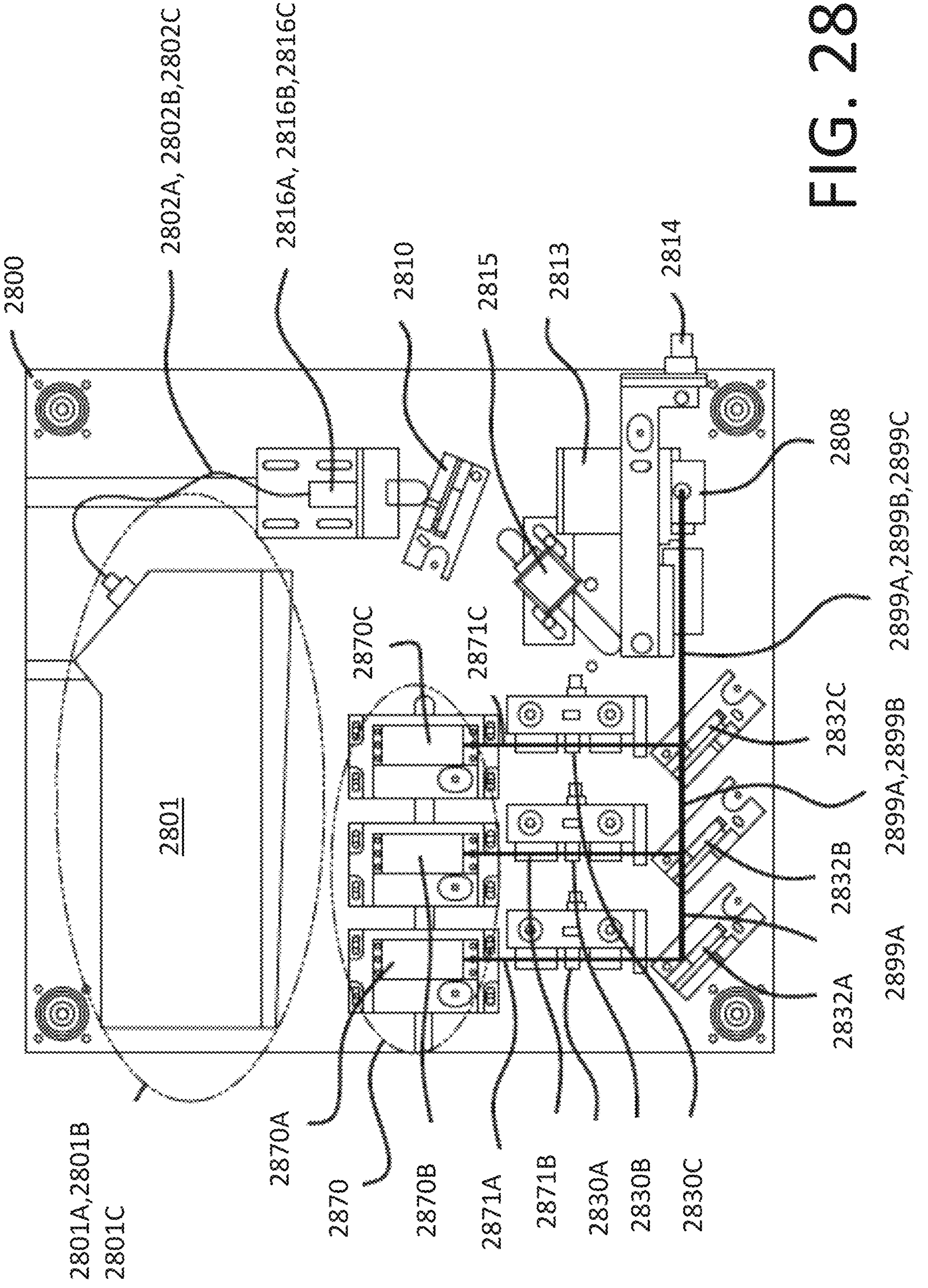

FIG. 28 is a top view of an optical plate assembly in a modular flow cytometry system with three excitation lasers.

Figure 29:
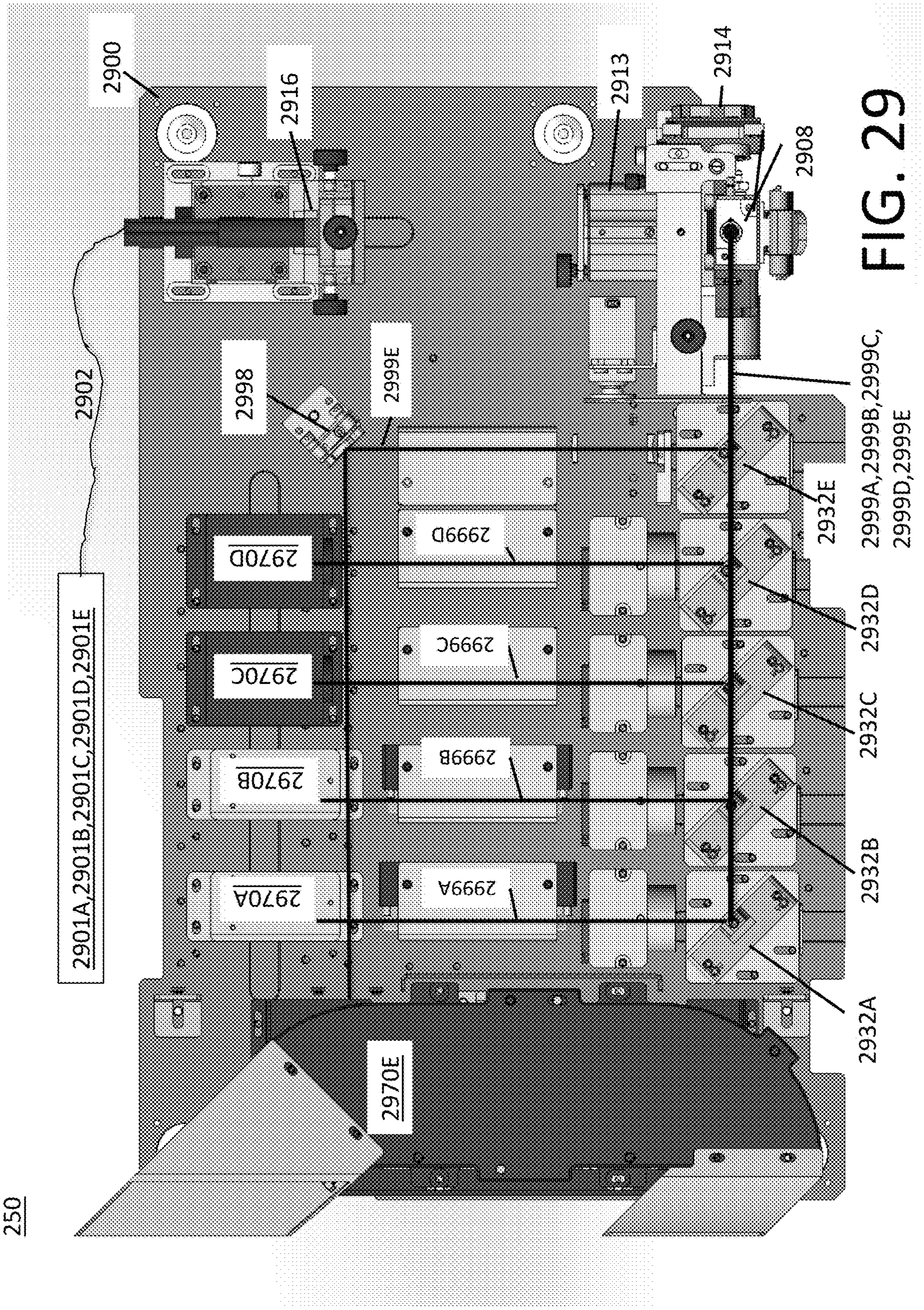

FIG. 29 is a top view of an optical plate assembly in a modular flow cytometry system with five excitation lasers, including a UV excitation laser, of the full spectrum flow cytometer.

DETAILED DESCRIPTION

In the following detailed description of the embodiments of the invention, numerous specific details are set forth in order to provide a thorough understanding of the present invention. However, it will be obvious to one skilled in the art that the embodiments of the invention may be practiced without these specific details. In other instances, well known methods, procedures, components, and circuits have not been described in detail so as not to unnecessarily obscure aspects of the embodiments of the invention.

The embodiments include a method, apparatus and system for building a multi-color fluorescence-based flow cytometry panel.

Full spectrum flow cytometry is a technology that enables the development of such highly multiparametric panels. A full spectrum flow cytometer measures the entire fluorochrome emission, from ultra-violet to near infra-red, across multiple lasers using many more detectors compared to a conventional flow cytometer. It produces very specific spectral fingerprints that are used to mathematically distinguish one fluorophore from another, even when their maximum emissions (the primary component measured by a conventional flow cytometer) are very similar. Leveraging this full spectrum technology, the ability to combine 30 or more fluorescently labeled antibodies becomes possible using a fluorescence-based flow cytometer.

Figure 1A:
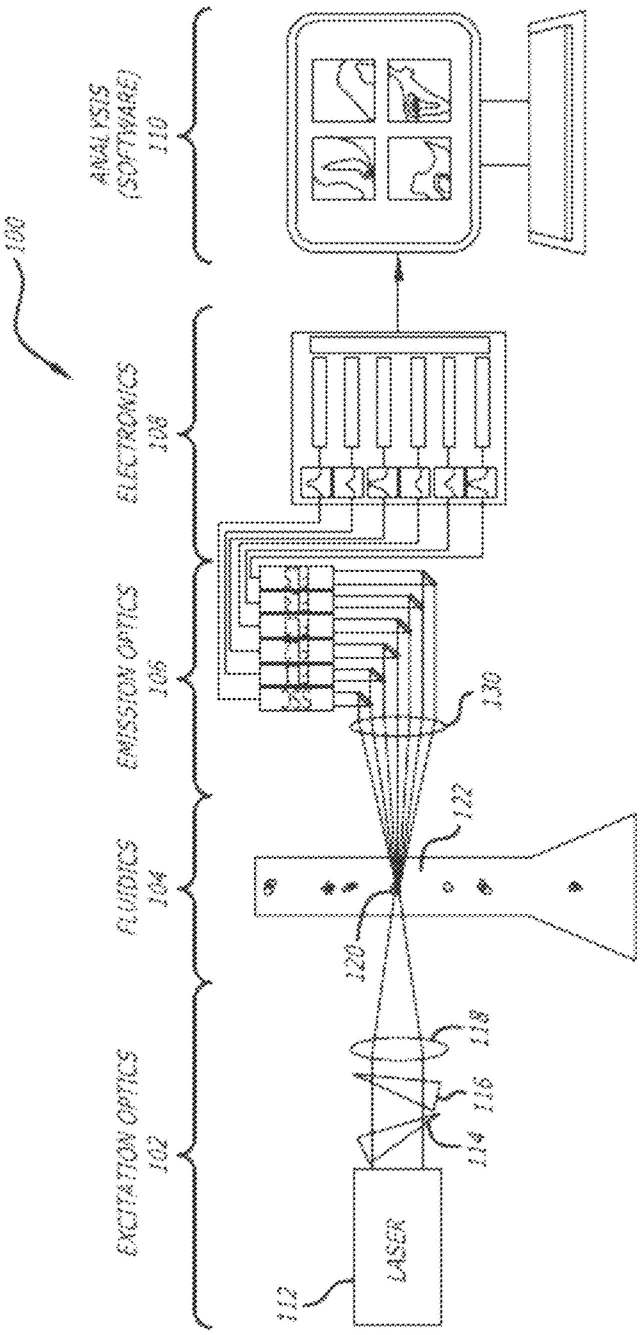
FIG. 1A is a basic conceptual diagram of a flow cytometer system.

Referring now to FIG. 1A, a basic conceptual diagram of a flow cytometer system 100 is shown. Various embodiments of the flow cytometer 100 may be commercially available. Five major subsystems of the flow cytometer system 100 include an excitation optics system 102, a fluidics system 104, an emission optics system 106, an acquisition system 108, and an analysis system 110. Generally, a "system" includes hardware devices, software devices, or a combination thereof.

The excitation optics system 102 includes, for example, a laser device 112, an optical element 114, an optical element 116, and an optical element, 118. Example optical elements include an optical prism and an optical lens. The excitation optics system 102 illuminates an optical interrogation region 120. The fluidics system 104 carries fluid samples 122 through the optical interrogation region 120. The emission optics system 106 includes, for example, an optical element 130 and optical detectors SSC, FL1, FL2, FL3, FL4, and FL5. The emission optics system 106 gathers photons emitted or scattered from passing particles. The emission optics system 106 focuses these photons onto the optical detectors SSC, FL1, FL2, FL3, FL4, and FL5. Optical detector SSC is a side scatter channel. Optical detectors FL1, FL2, FL3, FL4, and FL5 are fluorescent detectors may include bandpass, or long-pass, filters to detect a particular fluorescence wavelength. Each optical detector converts photons into electrical pulses and sends the electrical pulses to the acquisition system 108. The acquisition system 108 processes and prepares these signals for analysis in the analysis system 110.

The analysis system 110 can store digital representations of the signals for analysis after completion of acquisition. The analysis system 110 is a computer with a processor, memory, and one or more storage devices that can store and execute analysis software to obtain laboratory results of biological samples (or other types of samples, e.g., chemical) that are analyzed. The analysis system 110 can be further used to calibrate the flow cytometer with compensation controls when initialized, before running a reference sample through the flow cytometer. Reference samples can be formed in different ways to determine spillover vectors for a fluorescent dye or fluorochrome. A fluorochrome can be conjugated with an antibody and then attached to a biological cell or attached to a bead or particle.

Figure 1B:
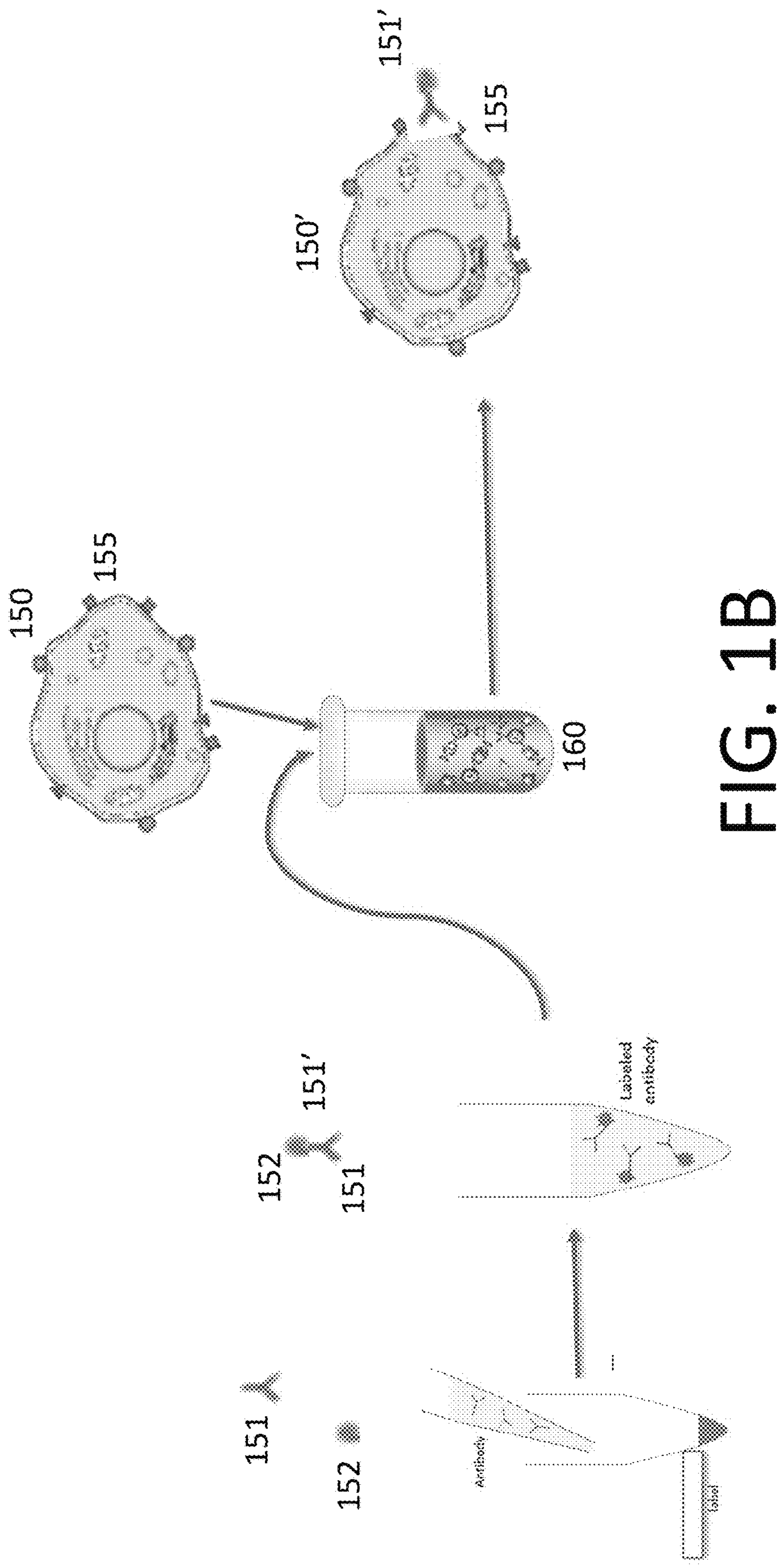
FIG. 1B is a conceptual diagram of a fluorochrome, an antibody, and a cell.

Referring now to FIG. 1B, a cell 150, an antibody 151, and a fluorochrome (dye) 152 are coupled together to form a reference sample with direct marking or staining of a cell. The cell 150 has one or more cell marker 155 sites to which an antibody can attach. The fluorochrome (dye) 152 is conjugated with the antibody 151 in advance to form a conjugated antibody 151'. For a reference sample, a single fluorochrome (dye) 152 is conjugated with a single antibody to generate a spillover vector. Subsequently, when analyzing a biological fluid with different unknown counts of cells in the biological fluid, multiple conjugated antibodies with different antibodies and different fluorochrome, can be used and add into the same biological sample.

The conjugated antibodies 151' and the cells 150 are mixed together in a test tube 160 so the conjugated antibodies 151' can attached to the desired cell marker sites 155 for the given type of cells 150 to form marked or stained cells 150' in the sample biological fluid. When run through the flow cytometer, the fluorochromes can be excited by laser light to fluoresce so that the fluorescence can be detected by detectors as events generating an event vector. The event vector can be used to generate a spill over matrix for the fluorochrome. When running a sample biological fluid with unknown counts, the cells counted by a flow cytometer by analyzing the events.

Figure 1C:
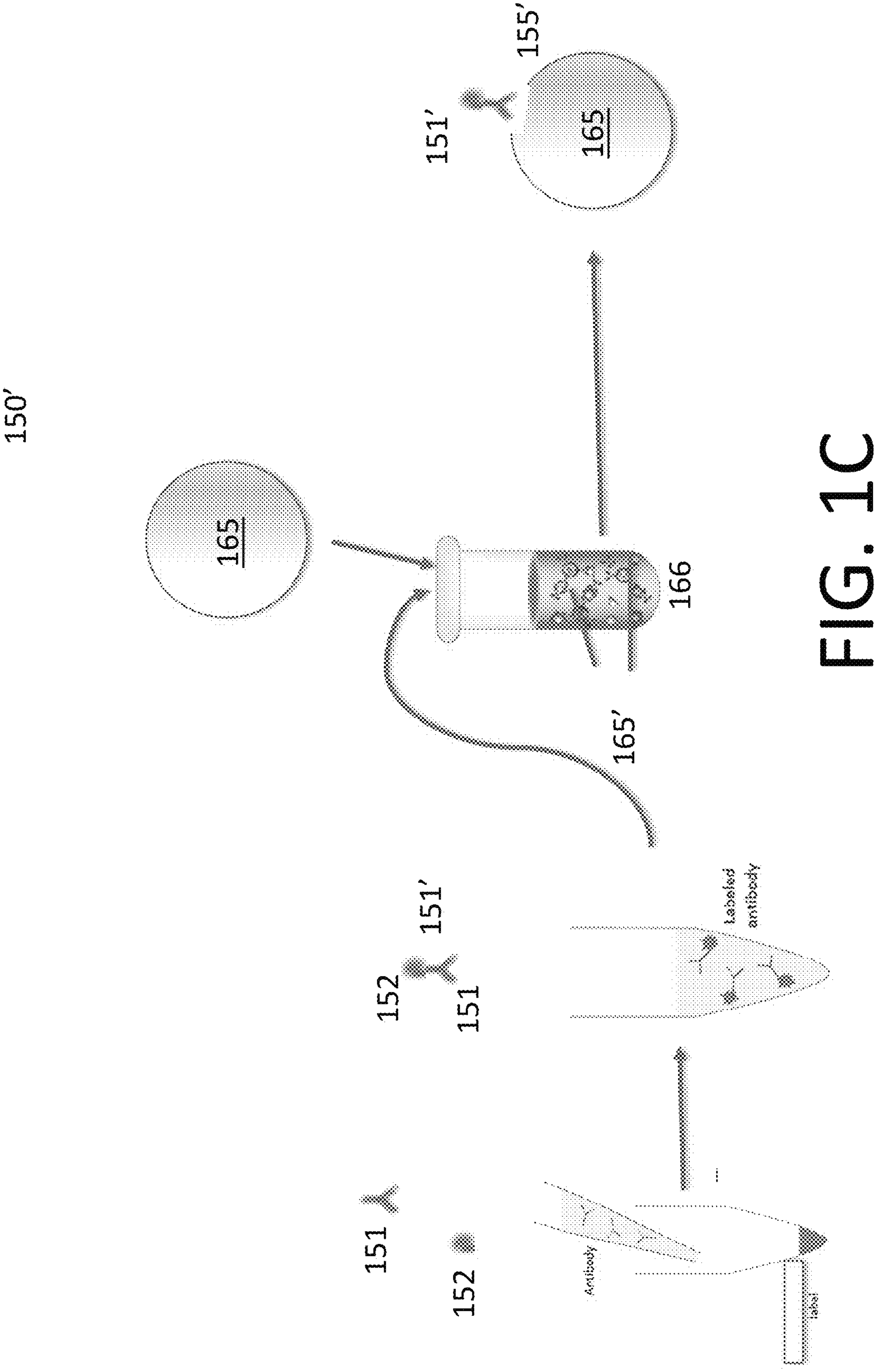
FIG. 1C is a conceptual diagram of forming a reference sample with a bead.

Referring now to FIG. 1C, a conceptual diagram of forming a reference sample with a bead 165 is shown. A bead 165, an antibody 151, and a fluorochrome (dye) 152 are coupled together to form a reference sample with a bead. The bead 165 may have one or more cell marker 155' sites to which an antibody can attach. As with the cell, the fluorochrome (dye) 152 is conjugated with the antibody 151 in advance to form a conjugated antibody 151'. For a reference sample, a single fluorochrome (dye) 152 is conjugated with a single antibody to generate a spillover vector.

The conjugated antibodies 151' and the beads 165 are mixed together in a test tube 166 so the conjugated antibodies 151' can attached to the desired marker sites 155' for the beads 165 to form marked beads 165' in a reference sample. When run through the flow cytometer, the fluorochromes can be excited by laser light to fluoresce so that the fluorescence can be detected by detectors as events generating an event vector. The event vector can be used to generate a spill over matrix for the fluorochrome. In this manner, either cells or beads can be used to test and fluorochrome for suitability to be used with a flow cytometer.

Reference Sample Run

Figure 2A:
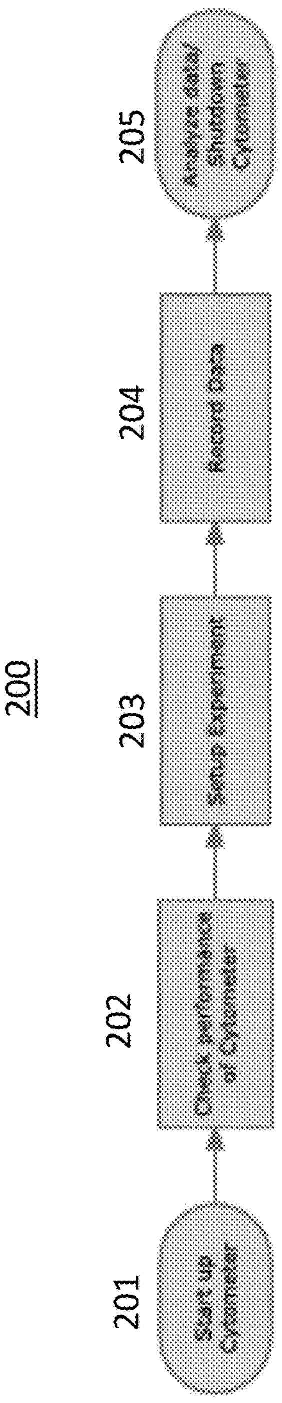
FIG. 2A is an overall method for performing an experiment with a biological sample and/or running calibration beads through a flow cytometer.

Referring now to FIG. 2A, a flowchart of a method 200 for a flow cytometer is shown. The flow cytometry system 100 of FIG. 1, or other flow cytometer systems (e.g., system 250 shown if FIG. 2E) disclosed herein, can carry out the method 200. Flow cytometry allows for data collection and analysis of data on single cells or particles of a plurality that are in a sample fluid.

In step 201, the system starts up the flow cytometer. In step 202, the system checks the performance of the flow cytometer and performs calibration if and as needed with calibration beads. If the flow cytometer was recently calibrated (e.g., same day or same hour), this step can be skipped.

In step 203, multiple experiments are setup to run to generate spillover vectors for each dye. A reference sample is prepared (fluorochrome conjugated to an antibody that is attached to a cell or a bead) to initially run to generate event vectors that can be converted into a spillover vector.

In step 204, the reference sample fluid with one fluorochrome is run through the flow cytometer for analysis with the data captured from N detectors being recorded. Multiple runs through the flow cytometer with the same reference sample fluid may be performed to be sure measurements are well understood. The data from N detectors is recorded for each run of the reference sample through the flow cytometer.

In step 205, after the sample fluid or calibration beads are run through the flow cytometer, the recorded data can be analyzed to determine results from the analysis by the flow cytometer.

Each spillover vector for one fluorochrome can be subsequently compared with another spillover vector for another fluorochrome to determine how different combinations of pairs of fluorochromes (dyes) and markers interact and spectrally interfere. The spillover vectors for each dye can be subsequently combined together into a spillover matrix for a total number and types of dye being used together to identify cells/particles in a single sample. Combinations of pairs of spillover vectors (columns) in the spillover matrix can be compared together to determine a similarity index between the two fluorochromes. For each reference sample, the light intensity density for each channel can saved as a reference vector and the data can be binned and plotted to form a full spectrum signature for the given fluorochrome.

The flow cytometer can also be shut down if no further samples or calibration beads are to be run. Alternatively, another sample or more calibration beads can be run through the flow cytometer to obtain and record (save) data and subsequently analyze the recorded data.

Figure 2B:
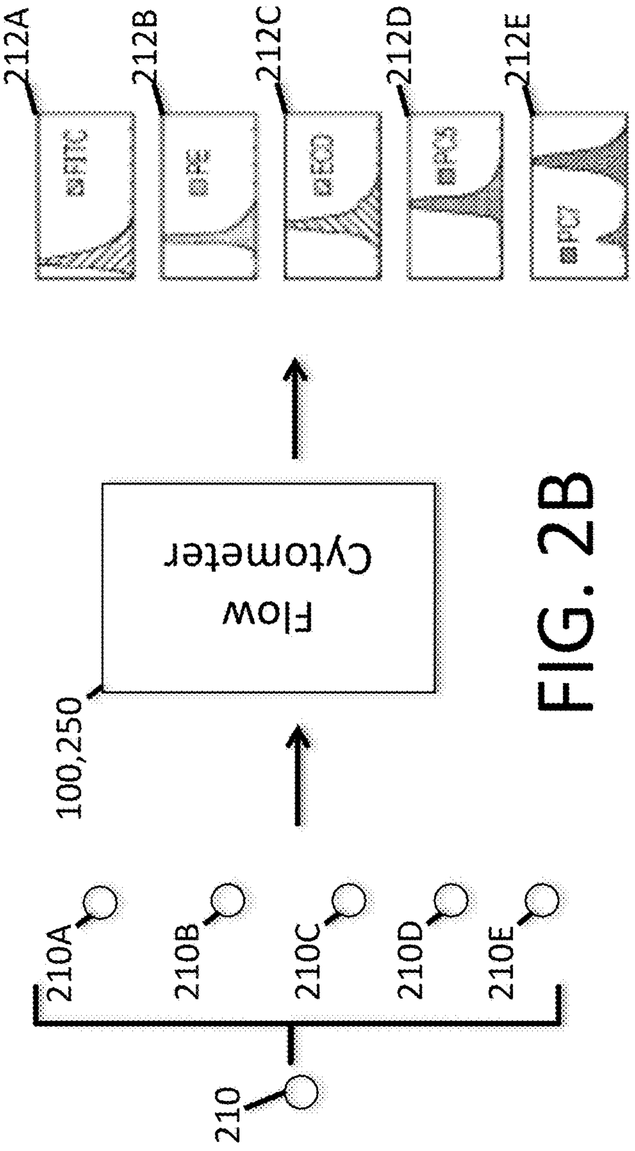
FIG. 2B is a diagram of a calibrating process of a flow cytometer with single stained compensation controls to generate an initial spillover matrix or reference matrix with levels of compensation.

In step 205, the system performs single stained compensation controls to generate an initial spillover matrix or reference matrix. When performing multicolor flow cytometry, the system uses single stained samples (reference samples) 210A-210E (collectively referred to by reference number 210) run through a flow cytometer 100,250 to determine the levels of compensation, such as shown in FIG. 2B. Single staining of the particles 210A-210E can reveal the respective spectral profile or signature 212A-212E of respective fluorochromes to the fluorescent photo-detectors of the instrument. The information obtained from the single stained particles 210 can be subsequently used to determine a simplicity index and a complexity index of a set of fluorochromes attached to the particles 210. The information obtained from the single stained particles 210 can also be subsequently used to determine a reference full spectrum signature for a fluorochrome useful for unmixing data from a mixed sample labeled with multiple fluorochromes.

The staining of the compensation control usually should be as bright or brighter than the sample. Antibody capture beads can be substituted for cells and one fluorophore conjugated antibody for another, if the fluorescence measured is brighter for the control. The exceptions to this are tandem dyes, which cannot be substituted. Tandem dyes from different vendors or different batches must be treated like separate dyes, and a separate single-stained control should be used for each because the amount of spillover may be different for each of these dyes. Also, the compensation algorithm should be performed with a positive population and a negative population. Whether each individual compensation control contains beads, the cells used in the experiment, or even different cells, the control itself must contain particles with the same level of auto-fluorescence. The entire set of compensation controls may include individual samples of either beads or cells, but the individual samples must have the same carrier particles for the fluorophores. Also, the compensation control uses the same fluorophore as the sample. For example, both green fluorescent protein (GFP) and Fluorescein isothiocyanate (FITC) emit mostly green photons, but have vastly different emission spectra. Accordingly, the system cannot use one of them for the sample and the other for the compensation control. Also, the system must collect enough events to make a statistically significant determination of spillover (e.g., about 5,000 events for both the positive and negative population).

During calibration in a conventional flow cytometer, the system obtains an initial spillover matrix from single stained reference controls. In a conventional flow cytometer, the fluorescence signals (e.g., colors) are separated out into discrete fluorescent bands using a series of edge filters and dichroic mirrors. The system detects (e.g., measures) each individual channel with a photo multiplying tube (PMT). During detection of the fluorescent signals, "spillover" can occur between fluorescent bands, which ideally are completely discrete, such as shown in the combined profile 226. The system defines the spillover (e.g., spillover 228 in the combined profile 226 in FIG. 2C) between the fluorescent bands with a spillover matrix [S].

Alternatively, during calibration in a spectral flow cytometer, the system obtains an initial reference matrix from single stained reference controls 210. Spectral flow cytometry is a technique based on conventional flow cytometry where a spectrograph and multichannel detector (e.g., charge-coupled device (CCD)) is substituted for the traditional mirrors, optical filters and photomultiplier tubes (PMT) in conventional systems. In the spectral flow cytometer, the side scattered light and fluorescence light is collected and coupled into a spectrograph, either directly or through an optical fiber, where the whole light signal is dispersed and displayed as a high-resolution spectrum on the CCD or coupled into one or more multichannel detectors for detection.

Figure 2C:
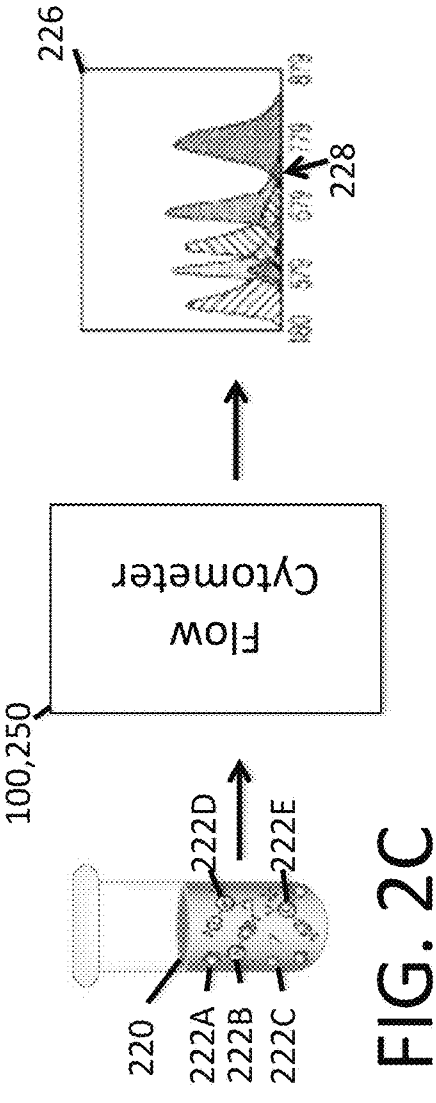
FIG. 2C is a diagram of running a sample through the flow cytometer resulting in a mixed sample event vector with an overlapping spectral profile due to multi-stained cells or particles.

In process step 204 of FIG. 2A, the sample 220 shown in FIG. 2C is run through the flow cytometer 100,250. The sample 220 includes a plurality of marked cells or particles 222A-222E that flow through each laser beam of each laser and generates fluorescent light and/or scattered light referred to as an event. The fluorescent light and/or scattered light is captured and detected in order to identify the particle and generate counts for the various types of particles in the sample 220. For each particle in the sample fluid 210 passing by the laser beam(s) and fluorescing light and/or scattering light, the system generates, obtains, and/or records data (e.g., event data) representing the overall spectral profile 226. For example, fluoresced cells in the sample fluid flowing through the flow cytometer are detected. An event occurs per particle/cell. Each full spectrum detection of a fluoresced cell by the detector modules excited by the lasers is an event. The event data for a particle/cell may be defined according to a measured sample event vector.

Figure 2D:
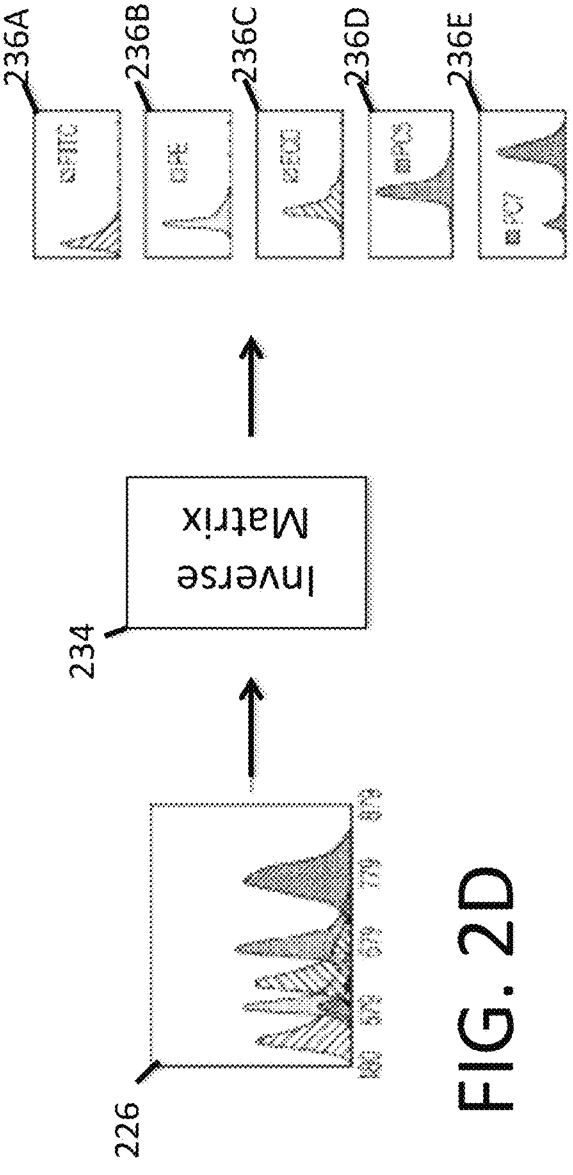
FIG. 2D is a diagram of a processing using an inverse matrix (determined from the initial spillover matrix and/or the initial reference matrix with fine adjustments) on the event data to generate a compensated sample event vector or an unmixed sample event vector.

In step 205, the system generates a compensated sample event vector (for conventional flow cytometer) or an unmixed sample event vector (for spectral flow cytometer) to count the number of various types of cells or particles in a sample 222 to obtain a measure of concentration. Generally as shown in FIG. 2D, an inverse matrix 234 (determined from the initial spillover matrix and/or the initial reference matrix with fine adjustments) is used on the event data representing the spectral profile 226 to generate the compensated sample event vector or the unmixed sample event vector representing separate spectral profiles or signatures 236A-236E of the various auto-luminescence (generated by the cells or particles themselves) or luminescence given off by the fluorochromes tagged to the various cells 222A-222E in the sample 220. For the conventional flow cytometer, the system calculates the compensated event vector based on the initial spillover matrix and the measured sample event vector. For the spectral flow cytometer, the system calculates the unmixed sample event vector based on the initial reference matrix and the measured sample event vector.

Unfortunately, the initial spillover matrix and the reference matrix tend to be insufficiently accurate to yield reliable results. An additional step can be taken, a fast compensation step, which includes compensating for inaccuracies of the initial spillover matrix and/or the reference matrix. Subsequently thereafter, based on the fast compensation, the system generates can generate a re-compensated sample event vector.

Obtaining Spillover Matrix from Single Stain Controls

A conventional flow cytometer generates or obtain a spillover matrix from single stained controls. A spectral flow cytometer can similarly obtain a spillover matrix. The steps for generating or obtaining a spillover matrix by using a conventional flow cytometer are further discussed.

Assume matrix [S] is an N×N dimensional spillover matrix obtained from single stained compensation controls, where N is the number of fluorescent detectors. Example compensation controls include beads 210 stained or dyed with fluorochromes such as fluorescein isothiocyanate (FITC), R-phycoerythrin (PE), Peridinin Chlorophyll Protein Complex (PerCP), phycoerythrin and cyanine dye (PE-Cy7), Allophycocyanin (APC), and a tandem fluorochrome combining APC and cyanine dye (APC-Cy7).

Assume vector {U} is a measured sample event vector with N values, each of which is from one of the N detectors detecting a compensation control (e.g., FITC, PE, PerCP, PE-Cy7, APC, APC-Cy7).

Assume vector {V} is the compensated sample event vector with N values. The measured sample event vector {U} is equal to the spillover matrix [S] multiplied with the compensated sample event vector {V}. This can be represented with the following matrix relationship with the measured sample event vector {U}:

$$[S]\{V\}=\{U\} \quad \text{Eq. 1}$$

Therefore, with the inverse spillover matrix [S]-1, the compensated sample event vector {V} can be obtained from the matrix equation:

$$\{V\} = [S]^{-1}\{U\} \quad \text{Eq. 2}$$

An initial spillover matrix [S] can be obtained by measuring each single stained control (e.g., FITC, PE, PerCP, PE-Cy7, APC, APC-Cy7) at each detector to obtain the following matrix:

$$[S] = \begin{bmatrix} 1.0 & S_{1,2} & \cdots & S_{1,n} \\ S_{2,1} & 1.0 & \cdots & S_{2,n} \\ \vdots & \vdots & \vdots & \vdots \\ S_{n,1} & S_{n,2} & \cdots & 1.0 \end{bmatrix} \quad \text{Eq. 3}$$

In the subscript x,y in Eq. 3, the x value represents the detector number. The y value of the subscript x,y in Eq. 3 represents the column associated with a single stained control.

Each column in the initial spillover matrix [S], a separation of variables (SOV) matrix, corresponds to one single stained control (e.g., FITC, PE, PerCP, PE-Cy7, APC, APC-Cy7). For example, column one corresponds to FITC single stained control. As another example, column two corresponds to PE single stained control; and so on for each single stained control that is run to calibrated the flow cytometer. Each row in the initial spillover matrix [S] corresponds to a given detector number. For example, row one corresponds with detector 1. Row two corresponds to detector 2, and so on.

In general, the initial spillover matrix that is generated is not accurate enough to accurately separate spectrum and identify cells or particles. Accordingly, fine adjustment of the non-diagonal element values of the initial spillover matrix [S] is needed (e.g., fine adjustment to the initial spillover matrix [S] generating an adjusted spillover matrix [S]' and its associated inverse, the adjusted compensation matrix [C]'). The fine adjustments may be made based on experience and judgment of the lab technician/operator. The fine adjustments are often made to correct the distortion caused by either the interactions of fluorochromes stained on the same cells or particles, or by the system for the measurements of the single stained and unstained controls, or by both distortions caused by the interactions and the system. Assume an adjustment matrix [D] is the fine adjustments to be made (e.g., added) to the non-diagonal element values of the initial spillover matrix [S]. A re-compensated event vector $\{V_R\}$ can be determined from the matrix equation $\{V_R\}=[[S]+[D]]^{-1}\{U\}$.

Obtaining Unmixed Event List Data for a Spectral Flow Cytometer

Alternatively, the system can include a spectral flow cytometer to generate or obtain unmixed event list data. The steps for generating or obtaining unmixed event list data by using a spectral flow cytometer are further discussed.

Assume [R] is a N×M reference matrix obtained from single stained reference controls, where N is the number of detectors, M is the number of fluorochromes ((e.g., FITC, PE, PerCP, PE-Cy7, APC, APC-Cy7) to be measured with M always less than N. In other words, the number of fluorochromes that are to be used to mark particles/cells in a mixed sample is less than the number of detectors. The matrix [R] is a set of full spectrum signatures obtain by independent runs of the single stained reference control for each fluorochrome that is to be used to label particles/cells in a mixed sample.

Assume {U} is a measured sample event vector with N values, each value of intensity is from one of the N detectors over a predetermined range of wavelengths. The measured sample event vector is obtained by running the labeled mixed sample with particles/cells that were labeled with the M fluorochromes.

Assume {V} is the unmixed sample event vector with M values (e.g., fluorescence intensity), each of which is the unmixed value for a fluorochrome (e.g., one of the FITC, PE, PerCP, PE-Cy7, APC, APC-Cy7).

The unmixed sample event vector {V} has the following matrix relationship with the measured sample event vector {U}:

$$[R]\{V\}=\{U\}$$

Since the number of the variables M in the unmixed sample event vector {V} is less than the number of variables N in the measured sample event vector {U} (e.g., the dimension of the unmixed sample event vector is less than the dimension of the measured sample even vector), then the system uses a least square algorithm to obtain the solution of the above equation.

Compared with conventional flow cytometer, the unmixed sample event vector is equivalent to the compensated event vector. Therefore, the spectral spillover matrix [S] for the unmixed event list data (e.g., unmixed sample event vector) is an identity matrix [I] as follows:

$$[S] = \begin{bmatrix} 1.0 & 0 & \cdots & 0 \\ 0 & 1.0 & \cdots & 0 \\ \vdots & \vdots & \vdots & \vdots \\ 0 & 0 & \cdots & 1.0 \end{bmatrix}$$

In general, the unmixed event list data is not accurate enough so that fine adjustment of identity spectral spillover is needed (e.g., fine adjustment to generate an adjusted spectral spillover matrix). Accordingly, the equation for the re-compensated event vector becomes $\{V_R\}=[[I]+[D]]^{-1}\{V\}$ where [D] is an n×n delta matrix with fine adjustments $\delta_{i,j}$ in the $i^{th}$ row and $j^{th}$ column respectively and zeroes where no fine adjustment is needed. For example, a delta matrix can be $$[D] = \begin{bmatrix} \delta_{1,1} & \cdots & 0 & \cdots & \delta_{1,n} \\ \delta_{2,1} & \cdots & \vdots & \cdots & \delta_{2,n} \\ \vdots & \cdots & \vdots & \cdots & \vdots \\ 0 & \cdots & \delta_{i,j} & \cdots & 0 \\ \vdots & \cdots & \vdots & \cdots & \vdots \\ \delta_{n,1} & \cdots & 0 & \cdots & \delta_{n,n} \end{bmatrix}.$$

Fast Compensation of Flow Cytometry Data

Accordingly, in flow cytometry (e.g., conventional and spectral), Flow Cytometry Standard (FCS) data collected from a cytometer is linear raw list data. The list data needs to be compensated before it is consumed on plots and used for statistics analysis.

The system performs fast compensation to account for insufficient accuracies in a spillover matrix and/or unmixed event list data.

Compensation of list data is based on an initial spillover matrix that the system obtains from measured single stained compensation controls and/or from fine adjustment input. The obtained initial spillover matrix is in general not accurate enough. Fine adjustments are made that generate an adjusted spillover matrix by finely adjusting values in the initial spillover matrix.

Every time a spillover value is finely adjusted, the spillover matrix needs to be inverted to obtain the compensation matrix. Then the compensation matrix is multiplied by each list data event vector to generate the compensated list data (e.g., re-compensated event vector).

Take an experiment of N fluorescent parameters, for example. For the compensation of each event vector, it requires $N^2$ multiplications plus N×(N−1) additions to generate the compensated event vector. The computation complexity is on the order of $N^2$ (e.g., $O(N^2)$).

For an experiment with a limited number of fluorochrome parameters and limited number of events, compensation calculation may not be the bottleneck in flow cytometry data analysis. However, if an experiment contains a large number of fluorescent parameters (e.g., over 20 fluorescent parameters) with a large number of events (e.g., 2 million events), the compensation calculation can be extremely time consuming. The consequence is that each time the system changes a spillover value, displayed plots and statistics can be extremely slow to respond on a computer interface due to extensive amount of computations processed.

Advantageously, the present system performs a fast compensation algorithm that significantly reduces the amount of computations without sacrificing any accuracy for the compensated list data when the system receives or performs fine adjustment of the spillover matrix for flow cytometry data analysis. This fast compensation algorithm requires, for example, only (3N+1) multiplications/divisions plus (N+1) additions. The complexity of this fast compensation algorithm is on the order of N (e.g., O(N)). Therefore, the present system can significantly improve the responsiveness of the displayed plots and statistics.

Consider, for example, a 20-color experiment with one million events. Whenever the system receives or performs fine adjustment of a spillover value, a typical compensation algorithm requires a total of 400 million multiplications plus 399 million additions. In contrast, the fast compensation algorithm of the present system requires only a total of 60 million multiplications plus 20 million additions. The saving of the total multiplications and additions are 566% and 1895%, respectively, compared with a typical compensation algorithm.

The following is the derivation of the present fast compensation algorithm:

Assume matrix [C] is the compensation matrix. The compensation matrix [C] is the inverse of the spillover matrix [S] by the matrix equation $[C]=[S]^{-1}$. If the compensation matrix [C] and the spillover matrix [S] are multiplied together, one acquires the identity matrix such as in the matrix equation [C] [S]=[I]. The compensated event vector {V} can be computed by multiplying the compensation matrix [C] and the uncompensated measured event vector {U} together represented by the matrix equation {V}=[C] {U}.

Due to a fine adjustment, the system generates or calculates an adjusted spillover matrix [S]'. Assume the value of one element in the initial spillover matrix [S] is changed, for example $S_{i,j}' \Rightarrow S_{i,j}+\delta_{i,j}$, the finely adjusted spillover matrix [S]' can be represented by the sum of the initial spillover matrix [S] summed with the fine adjustments in the delta matrix [D] by the matrix equation [S]'=[S]+[D] where $$[D] = \begin{bmatrix} 0 & \cdots & 0 & \cdots & 0 \\ \vdots & \cdots & \vdots & \cdots & \vdots \\ \vdots & \cdots & \vdots & \cdots & \vdots \\ 0 & \cdots & \delta_{i,j} & \cdots & 0 \\ \vdots & \cdots & \vdots & \cdots & \vdots \\ 0 & \cdots & 0 & \cdots & 0 \end{bmatrix}$$

is the delta matrix in which subscripts i and j represent the $i^{th}$ row and $j^{th}$ column respectively. The re-compensated event vector $\{V_R\}$ can be calculated by multiplying the inverse of the finely adjusted spillover matrix [S]', the finely adjusted compensation matrix [C]', and the uncompensated measured event vector {U} together such as represented by the matrix equation $\{V_R\}=[[S]+[D]]^{-1}\{U\}$. The delta matrix [D] has the same dimensions as the initial spillover matrix [S]. The delta matrix [D] includes delta values $\delta_{i,j}$ for finely adjusting the initial spillover matrix [S].

Since [S]+[D]=[S]([I]+[C][D]), $[[S]+[D]]^{-1}=([I]+[C][D])^{-1}[C]$, the equation for the re-compensated event vector $\{V_R\}$ can be rewritten as $$\{V_R\} = ([I]+[C][D])^{-1}[C]\{U\} = ([I]+[C][D])^{-1}\{V\}$$

where $([I]+[C][D])^{-1}$ is a re-compensation matrix.

Since the re-compensation matrix can be simplified as $$([I]+[C][D])^{-1} = \begin{bmatrix} 1 & \cdots & C_{1,i}\delta_{i,j} & \cdots & 0 \\ \vdots & \cdots & \vdots & \cdots & \vdots \\ \vdots & \cdots & \vdots & \cdots & \vdots \\ 0 & \cdots & 1+C_{j,i}\delta_{i,j} & \cdots & 0 \\ \vdots & \cdots & \vdots & \cdots & \vdots \\ 0 & \cdots & C_{n,i}\delta_{i,j} & \cdots & 1 \end{bmatrix}^{-1} = \begin{bmatrix} 1 & \cdots & \frac{-C_{1,i}\delta_{i,j}}{1+C_{j,i}\delta_{i,j}} & \cdots & 0 \\ \vdots & \cdots & \vdots & \cdots & \vdots \\ \vdots & \cdots & \vdots & \cdots & \vdots \\ 0 & \cdots & \frac{1}{1+C_{j,i}\delta_{i,j}} & \cdots & 0 \\ \vdots & \cdots & \vdots & \cdots & \vdots \\ 0 & \cdots & \frac{-C_{n,i}\delta_{i,j}}{1+C_{j,i}\delta_{i,j}} & \cdots & 1 \end{bmatrix},$$

then the matrix equation for the re-compensated event vector can be written as $$\{V_R\} = \begin{bmatrix} 1 & \cdots & \frac{-C_{1,i}\delta_{i,j}}{1+C_{j,i}\delta_{i,j}} & \cdots & 0 \\ \vdots & \cdots & \vdots & \cdots & \vdots \\ \vdots & \cdots & \vdots & \cdots & \vdots \\ 0 & \cdots & \frac{1}{1+C_{j,i}\delta_{i,j}} & \cdots & \vdots \\ \vdots & \cdots & \vdots & \cdots & \vdots \\ 0 & \cdots & \frac{-C_{n,i}\delta_{i,j}}{1+C_{j,i}\delta_{i,j}} & \cdots & 1 \end{bmatrix} \begin{bmatrix} V_1 \\ \vdots \\ V_j \\ \vdots \\ \vdots \\ V_n \end{bmatrix} = \begin{bmatrix} V_1 - V_j\frac{C_{1,i}\delta_{i,j}}{1+C_{j,i}\delta_{i,j}} \\ \vdots \\ V_j - V_j\frac{C_{j,i}\delta_{i,j}}{1+C_{j,i}\delta_{i,j}} \\ \vdots \\ \vdots \\ V_n - V_j\frac{C_{n,i}\delta_{i,j}}{1+C_{j,i}\delta_{i,j}} \end{bmatrix}$$

Each component of the re-compensated vector is determined by an addition/subtraction and multiplication/division with components of the uncompensated measured event vector {U} thereby significantly reducing the number of computations. Accordingly, the re-compensated event vector $\{V_R\}$ can be computed much more quickly by a processor of a computer using the fast compensation algorithm.

Thus, using the fast compensation algorithm, calibration bead samples can be more quickly analyzed with a flow cytometer and results more efficiently obtained. Instead of a researcher or a lab technician spending one or more days to obtain data, data can be obtained within hours by using the fast compensation algorithm.

Full Spectrum Flow Cytometer

Figures 1, 2E:
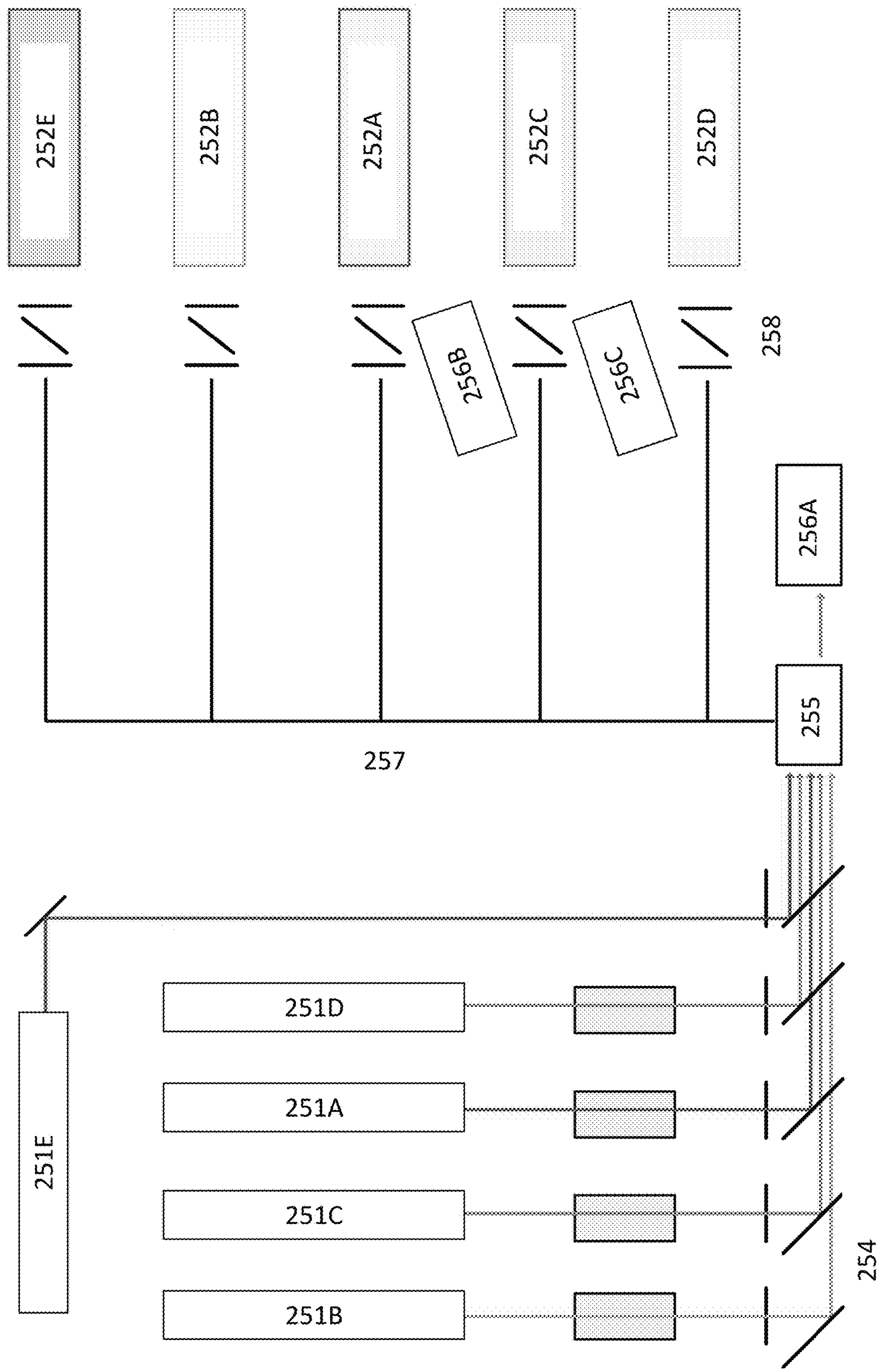
FIG. 2E (2E-1 and 2E-2) is a schematic diagram of a full spectrum flow cytometer.
Figures 2, 2E:
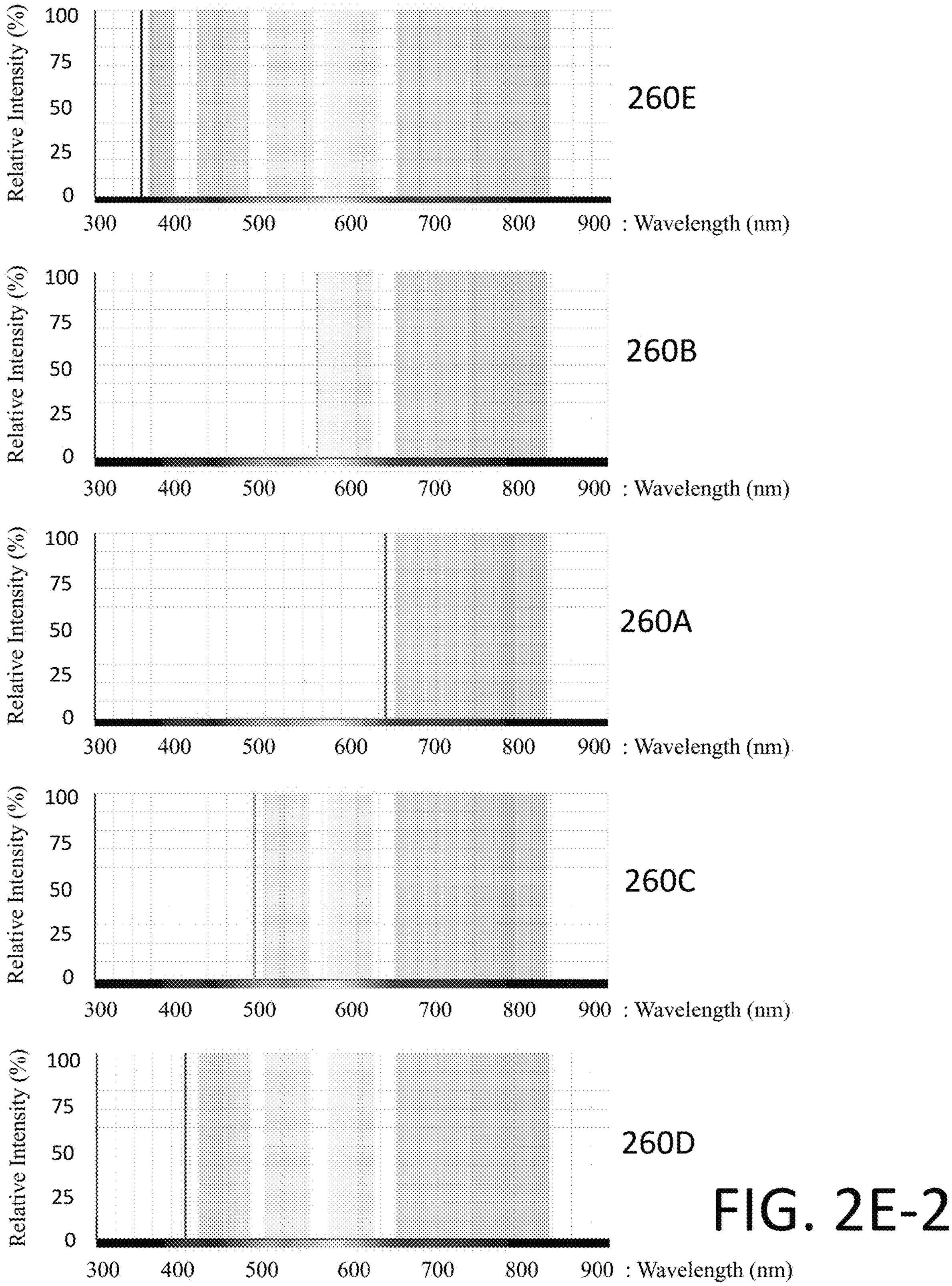

Referring now to FIG. 2E, a schematic diagram of a full spectrum flow cytometer 250 is shown. United States (US) patent application Ser. No. 15/659,610 titled COMPACT DETECTION MODULE FOR FLOW CYTOMETERS filed on Jul. 25, 2017 by inventors Ming Yan et al., and U.S. patent application Ser. No. 15/498,397 titled COMPACT MULTI-COLOR FLOW CYTOMETER filed on Apr. 26, 2017 by David Vrane et al. describes further details of flow cytometers and are incorporated herein by reference.

The full spectrum flow cytometer 250 can be variably configured with different numbers of lasers and different numbers of detector modules. In one embodiment, the full spectrum flow cytometer 250 can include five lasers (Red 640 nm, Yellow-Green 561 nm, Blue 488 nm, Violet 405 nm, and UV 355 nm) 251A-251E and five detector modules 252A-252E as shown in FIG. 2E to provide full spectrum analysis. With five detector modules, each of the detector modules (Red, Yellow-Green, Blue, Violet, and UV) 252A-252E can be associated with one of the five lasers as shown in FIG. 2E. Each of the five lasers generate laser light of five different wavelengths such as ultraviolet (UV) 355 nm, Violet 405 nm, Blue 488 nm, Yellow Green 561 nm, and Red 640 nm. Equipped with five lasers and five detectors, the full spectrum flow cytometer 250 can be used to develop color panels with 28 or more colors.

The optical paths of the laser light for each of the five lasers (UV 355 nm, Violet 405 nm, Blue 488 nm, Yellow Green 561 nm, and Red 640 nm) is shown in FIG. 2E. The lasers are spatially separated, each having an independent optical path to the flow cell 255. One or more optical components 254, such as mirrors, lenses, and filters, can be used to direct the laser light of each laser into the flow cell 255 to strike particles/cells in the sample fluid as they pass by an interrogation region.

After striking a particle in the flow cell 255, the fluorescent light is collected and directed through a plurality of optical fibers 257 and one or more optical elements (e.g., lenses) 258 into each of the individual detector modules 252A-252E. Each of the detector modules 252A-252E uses a sequential array of a plurality of avalanche photodiodes (APD) as the photodetectors. The full spectrum flow cytometer 250 can further include a plurality of scatter detectors, including a forward scatter (FSC) detector 256A near the flow cell, a blue side scatter detector 256B near the lens/filters for the red detector module, and a violet side scatter detector 256C near the lens/filters for the blue detector module. The plurality of scatter detectors are typically used to control data capture by the detector modules in the flow cytometer and data storage in a storage device. Each of the detector modules 252A-252E can capture a plurality of raw digital data for a given particle/cell as each laser beam of the plurality of lasers strike the same particle. The plurality of raw digital data is captured at slightly different times (laser delay) as the marked particle/cell passes by each laser beam in the flow channel. For example, the yellow/green laser may first strike the particle generating a first set of raw digital data, the violet laser second generating a second set of raw digital data, the blue laser third generating a third set of raw digital data, the red laser fourth generating a fourth set of raw digital data, and the UV laser lastly generating a fifth set of raw digital data for the same particle. If the plurality of lasers are arranged in a different order along the flow channel, the sequential order of generation of raw digital data by the same particle will be different. While an associated detector module is capturing light from its associated lasers, data from detectors in the other detector modules can be ignored. For example, at the time when the red laser strikes the particle/cell, the data from the red detector module is captured while the data from the UV, violet, yellow green, and blue detector modules can be ignored.

With the addition of the UV laser 251A and having five detector modules providing sixty-four (64) fluorescence detectors (see FIG. 2G), the full spectrum flow cytometer 250 has the power to take highly multiplexed assays beyond thirty (30) colors. The incorporation of the UV laser 251A allows the full spectrum flow cytometer 250 to perform at a different wavelength and discriminate different colors than those systems without. The UV laser enables the use of UV light excited fluorochromes, such as BUV737 and BUV395 fluorochromes, giving researchers additional flexibility on how they design experiments for a sample of particles.

FIG. 2F illustrates the configuration of each photo-detector in each of the five detector modules 252A-252E used in the embodiments of a full spectrum flow cytometer 250. Each detector has a bandpass filter in front of it to filter out light. The bandpass filter allows predetermined wavelengths through to the photo detector for detection while filtering out other wavelengths. The detector number (also referred to herein as channel number) and wavelength information of the bandpass filters associated with each photo-detector is shown. The ultraviolet (UV) detector module 252E has sixteen (16) detectors labeled as channels UV1-UV16 based on their position in the sequential array of detectors in the module. The violet detector module 252D has sixteen (16) detectors labeled as channels V1-V16 based on their position in the sequential array of detectors in the module. The blue detector module 252C has fourteen (14) detectors labeled as channels B1-B14 based on their position in the sequential array of detectors in the module. The yellow green detector module 252B has ten (10) detectors labeled as detector channels YG1-YG10 based on their position in the sequential array of detectors in the module. The red detector module 252A has eight (8) detectors labeled as detector channels R1-R8 based on their position in the sequential array of detectors in the module.

The multiple lasers in the flow cytometer are slightly spaced apart and sequentially strike the same particle/cell as it flows through the flow channel. This sets up a small amount of time delay between each subsequent laser strike (laser intercept) of the same particle/cell. There is a similar amount of time delay in the respective signal detected by the detectors and the generation of digital data from each laser strike (laser intercept) for the same particle/cell. The small amount of time is referred to as laser delay time and is predetermined by running a quality control experiment (e.g., daily QC runs) before running an experiment with a biological sample or other control. The full spectrum of fluorescence light from each laser striking the particle/cell is sent to each detector module by the fiber optic cables 257. Based on the laser delay time, the data generated by the detectors from each laser strike (laser intercept) can be associated with a given laser. For example, at one point in time a blue laser strikes the particle/cell and the detectors in the blue detector module can detect fluorescence and generate data for the blue laser strike. After a predetermined laser delay time between blue and red lasers, the same particle is struck by the red laser. Based on the time of the red laser strike, the detectors in the red detector module can detect fluorescence and generate data associated with the red laser strike. The laser delay time between the different lasers can be different but predetermined in order to be able to associate the captured data with the appropriate laser. Furthermore, the arrangement of the lasers can be in a different sequential order such that the sequence of laser strikes can differ. Moreover, the associated laser delay time can differ between laser strikes between power cycles of the flow cytometer. In any case, the data generated by each respective module that is delayed from the first data generated, is aligned together in time and associated with the particle/cell of a single event. The captured data from each detector module may be tagged with a particle/cell number count in the sample run and temporarily stored in a storage device, such as a register, memory or hard drive, for subsequent alignment together as a single event.

Fluorochromes are excited over a wavelength range (excitation wavelength range) associated with the wavelength of the laser and when excited, can emit fluorescence over a different wavelength range (emission wavelength range). The wavelength range of each detector module is associated with the expected emission wavelength range from the excitation of fluorochromes for the associated laser.

With reference to FIG. 2F, the bandpass filter before each detector is used to selectively pass the desirable wavelengths in the pass band range to be detected at a given photo detector for the associated excitation laser. The band bass filter rejects the wavelengths of light outside the pass band range of wavelengths. For example, the first red detector channel (R1 detector channel), the band pass filter has a center wavelength of 661 nanometers (nm) and a bandwidth of 17 nanometers around the center wavelength. Accordingly, in the band pass of wavelengths, a detector can reliably detect a wavelength range around a center wavelength and plus and minus one half the bandwidth. In the case of the R1 detector channel shown in FIG. 2F, the wavelength range is from the center wavelength minus one half the bandwidth (661 nm−8.5 nm=652.5 nm) to the center wavelength plus one half the bandwidth (661 nm+8.5 nm=669.5 nm). In the case of the R8 detector channel, the wavelength range is from the center wavelength minus one half the bandwidth (811.5 nm−17 nm=794.5 nm) to the center wavelength plus one half the bandwidth (811.5 nm+17 nm=828.5 nm). Accordingly, the red detector module detects fluorescent light over a wavelength range from 625 nm to 828.5 nm for fluorescent particles excited by the red laser. The yellow green detector module detects fluorescent light over a wavelength range from 567 nm to 828.5 nm for fluorescent particles excited by the yellow green laser. The blue detector module detects fluorescent light over a wavelength range from 498 nm to 828.5 nm for fluorescent particles excited by the blue laser. The violet detector module detects fluorescent light over a wavelength range from 420 nm to 828.5 nm for fluorescent particles excited by the violet laser. The ultra violet detector module detects fluorescent light over a wavelength range from 365 nm to 828.5 nm for fluorescent particles excited by the ultra violet laser. This detection range includes the full visible light (electromagnetic) spectrum from 380 nm to 780 nm, a portion (365 nm to 379 nm) of the non-visible UV light spectrum, and a portion (781 nm to 828.5 nm) of the non-visible infrared light spectrum.

If even more than 64 detectors are used, an increased granularity in the data at various wavelengths can be captured. The compactness of photo detectors (e.g., avalanche photo-diodes) and the detector array in the detector module has led to embodiments of up to 64 detectors and can lead to a further increase in the numbers of available detectors. A larger number of detectors can lead to increased numbers of colors that can be detected (discriminated) and an increased number of fluorochromes that can be used to examine particles within a single sample by a single run through a flow cytometer. The use of compact photodetectors in a compact photo detector array as the detector modules in the full spectrum flow cytometer 250 has improved the efficiency of running samples through a flow cytometer and examining the resultant data.

While a single particle has been described passing through each laser, a sample fluid run through a flow cytometer can have thousands of cells/particles per micro liter with hundreds of thousands or more of particles in a sample fluid size of hundreds of microliters (e.g. 500,000 particles in a 500 microliter sample size). The same sample can have different types of cells with hundreds of thousands or more. With a multi-color experiment, different fluorochromes are attached to different particles/cells to count different types of particles in the same sample. In a single run through the flow cytometer, the intensity and wavelength of each color of fluorescent light generated by the excited fluorochrome on the labeled cells can be detected and plotted on a chart by wavelengths to indicate the spectrum of light captured by the sample run. Furthermore, the intensity of fluorescent light for each given color/detector channel can be binned into count ranges with the particle count falling into these ranges being summed up together and plotted on the chart to show the particle cell density for the wavelengths of light.

Figures 1, 2G:
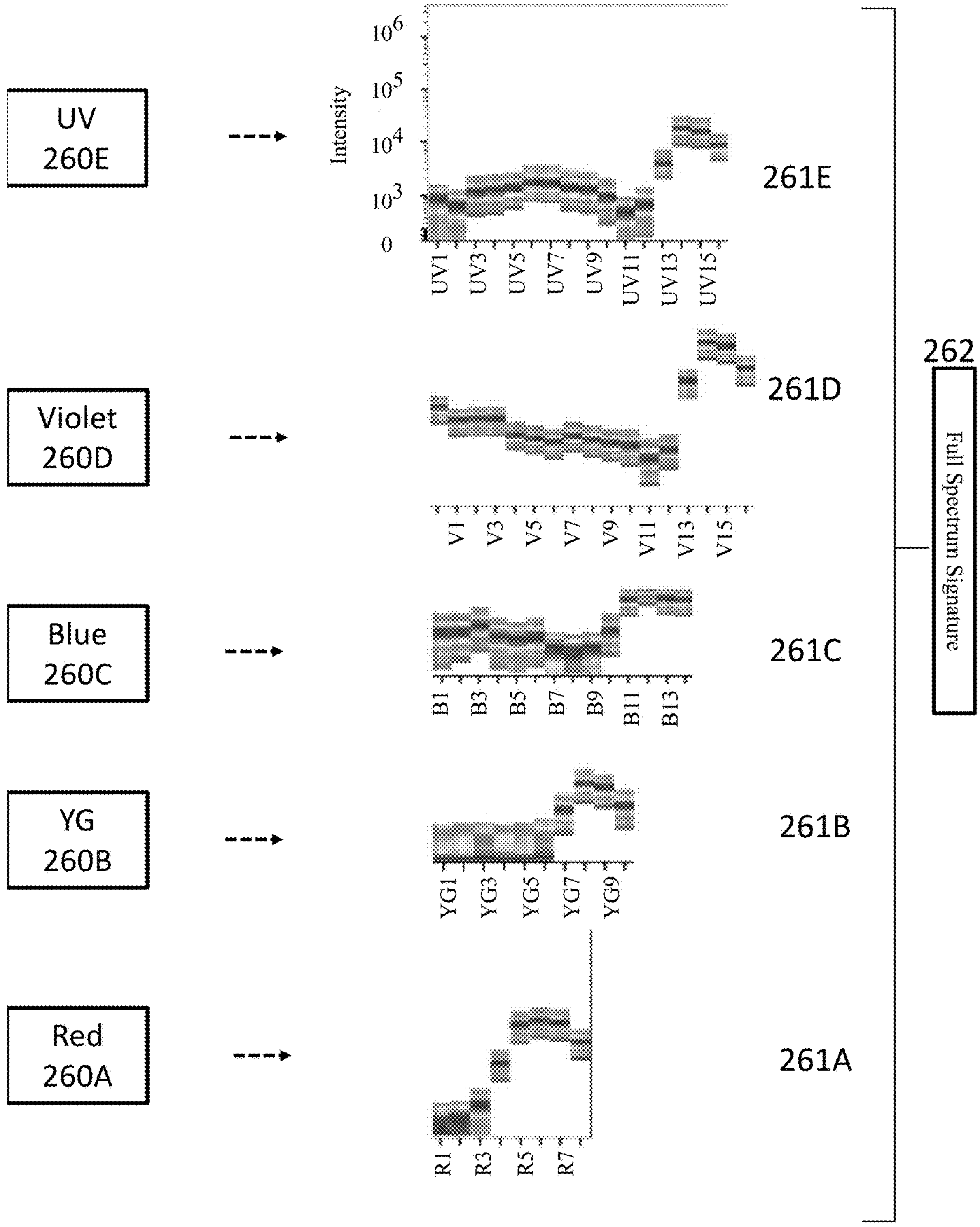
FIG. 2G (2G-1 and 2G-2) illustrates the individual spectrum signature of each color laser and combined full spectrum signature of an exemplary fluorochrome.
Figures 2, 2G:
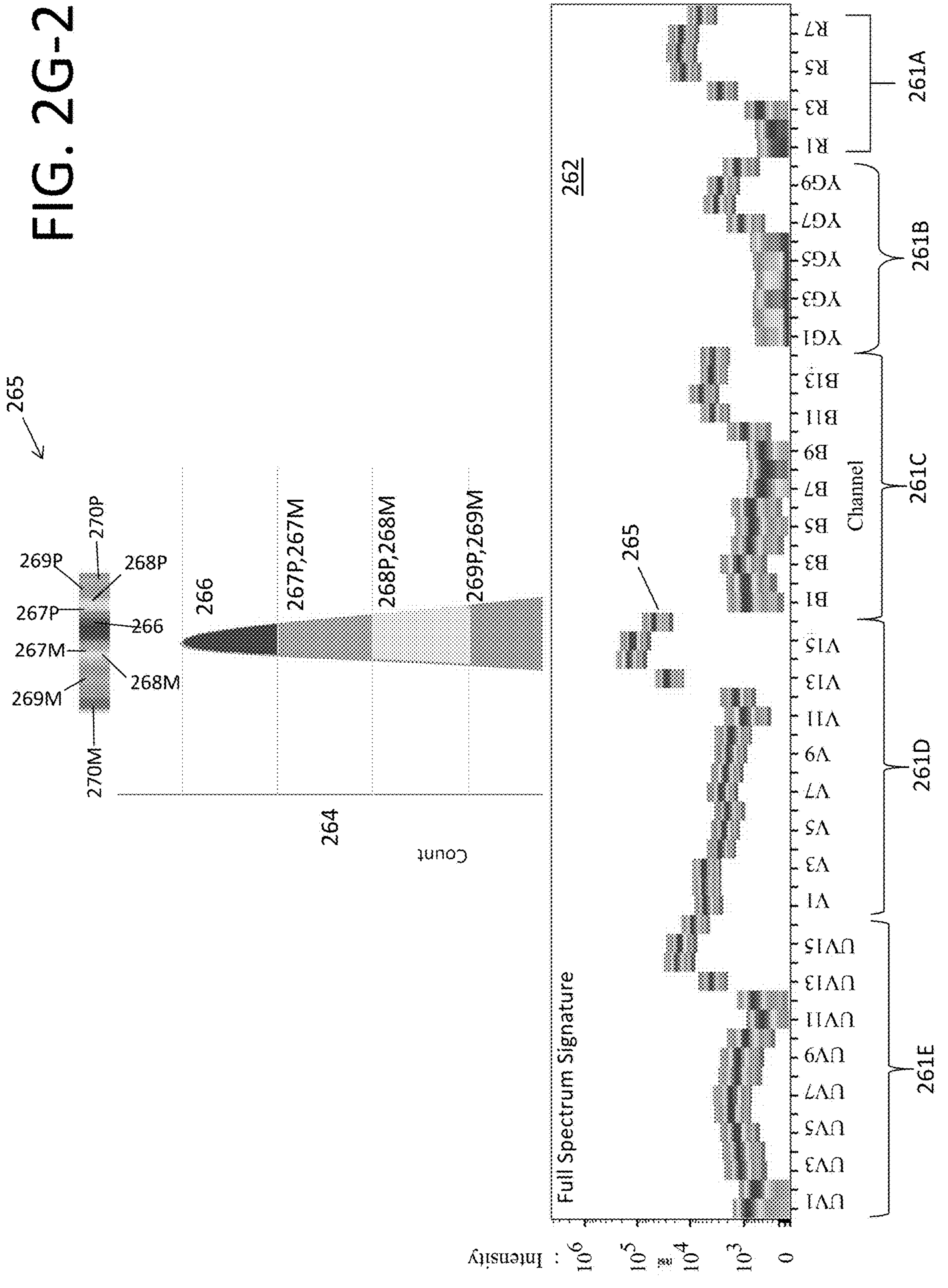

In FIG. 2E, the charts 260A-260E of data, normalized intensity (Y axis) versus wavelength (X axis), represents the range of light spectral components captured by each respective detector module for all events (each cell passing through the lasers) in a sample, such as a reference control with a single fluorochrome being used to generate a reference full spectrum signature. In FIG. 2G, the raw channel data captured for each detector module 252A-252E can respectively be plotted, based on the detector channel number, as a portion (individual detector module spectrum signature) 261A-261E of a full spectrum (spectral) signature of the sample run. In the plots of the individual detector module spectrum signature portions 261A-261E associated with each color laser 251A-251E and associated detector module 252A-252E pairing, the intensity (Y axis) and binned density count are plotted as a function of the detector channel number (X axis). Each of the individual detector module spectrum (spectral) signatures is formed out of a channel spectrum signature, such as channel spectrum signature 265 for the detector module spectrum (spectral) signature 261D for example.

The channel spectrum signature is plotted based on a plurality of binned intensity levels and the particle counts within those bins. For example, the greatest count (highest density) at the binned intensity level range for the channel is given a first color (e.g., red) located at the center intensity level range 266 of the channel spectrum signature 265. For each channel spectrum signature, the other binned intensity levels are either above 267P,268P,269P or below 267M, 268M,269M the center intensity level 266 having the greatest particle/cell count. The second intensity levels 267P, 267M respectively just above 267P and below 267M the center intensity level 266 are assigned a second color differing from the first color of the center intensity level. The third intensity level 268P above the second and center intensity levels and the third intensity level 268M below the second and center intensity levels are assigned a third color differing from the first and second colors. The fourth intensity level 269P above the third, second, and center intensity levels and the fourth intensity level 269M below the third, second and center intensity levels are assigned a fourth color differing from the first, second, and third colors. In this manner, intensity density information can be communicated to the user for a given detector channel.

After generating plots of the individual detector module spectrum (spectral) signatures 261A-261E, the plots of the individual detector module spectrum (spectral) signatures can then be merged together. In FIG. 2G, the individual detector module spectrum (spectral) signatures 261A-261E are merged together along an X axis of detector channel number to form a plot of a full spectrum (spectral) signature 262 of the exemplary sample run through the full spectrum flow cytometer. Along the X axis, from right to left, are the red detector module spectrum signature 261A, the yellow green detector module spectrum signature 261B, the blue-detector module spectrum signature 261C, the violet detector module spectrum signature 261D, and the ultraviolet detector module spectrum signature 261E merged together forming the full spectrum signature for a given sample run. Different labeled samples run through the flow cytometer 250, will generate different detector module signatures and accordingly different merged full spectrum (spectral) signatures. Single stained control samples (reference controls) are run through the full spectrum flow cytometer used to determine the full spectrum signature of each fluorochrome before being used with other fluorochromes to label a particle/cell in a mixed sample of a plurality of particles/cells.

Instead of just looking at peak intensity levels, the full spectrum signature for one fluorochrome can be used to distinguish from noise and another fluorochrome having a different full spectrum signature. Detecting light intensity over the full spectrum is an advantage of a full spectrum flow cytometer over that of a conventional flow cytometer that just looks at peak intensity levels. When a conventional flow cytometer shows overlap in the spectrum plots of fluorescent dies, the full spectrum signatures of each when run through a full spectrum flow cytometer can be distinguishable. In planning an experiment, it is desirable to select different fluorochromes that can be distinguishable from each other by their full spectrum signatures. Fluorochromes with similar emission but different spectral signatures can be distinguished from each other. The mathematical method to differentiate between multiple fluorophores (mixed fluorescent light) is called spectral unmixing and results in an unmixing matrix that is applied to the captured data of the sample.

Particles/cells may autofluoresce when struck by the five lasers and have its own full spectrum signature. Accordingly, the autofluorescence of the various particles/cells can also be unmixed, based on the autofluorescence full spectrum signature, and be used to distinguish it from other particle/cell types and the fluorochrome attached to other cells in a mixed sample.

Optimized Multicolor Immunofluorescence Panel (OMIP)

Figure 5B:
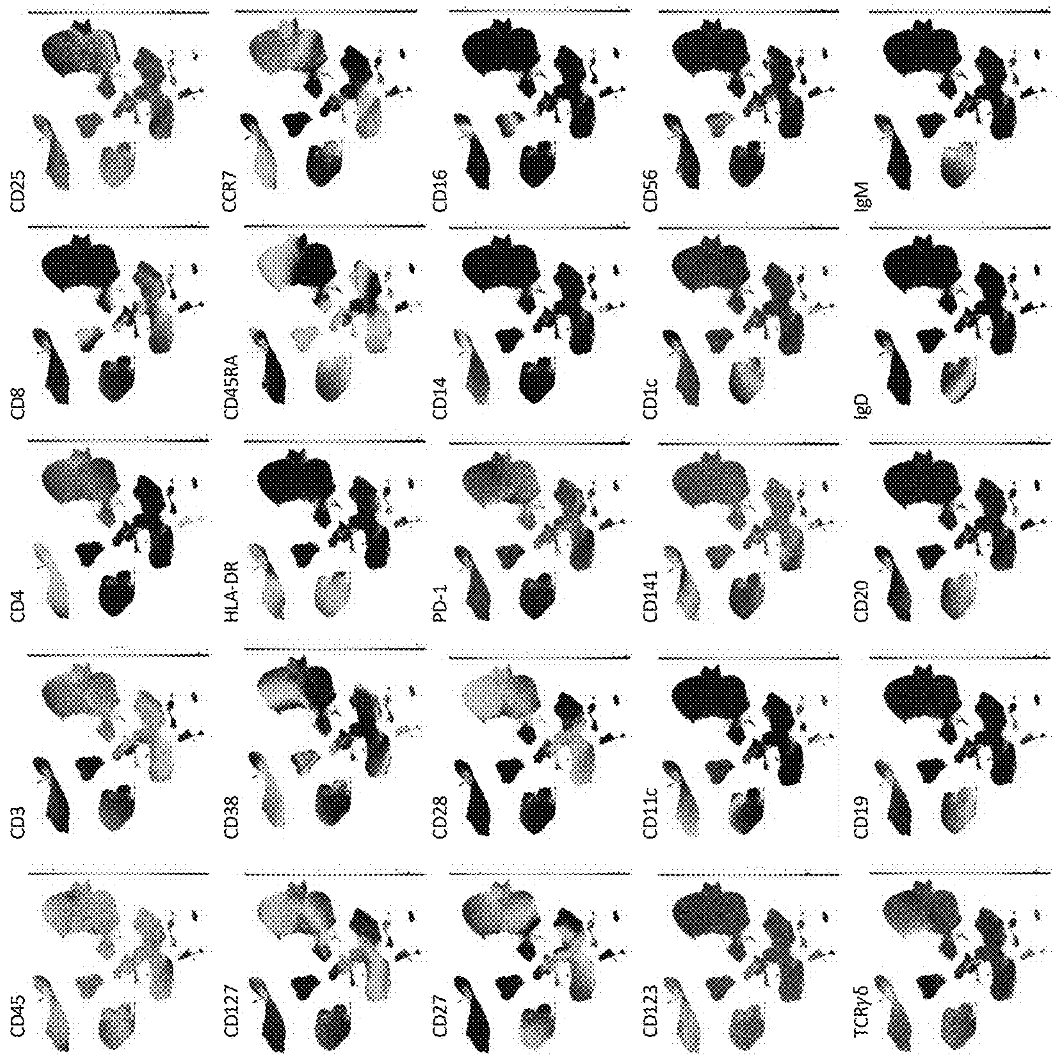
FIGS. 5A-5Q illustrate data from a 25 color panel developed using a full spectrum cytometer with four lasers.
FIG. 5R illustrates the spectrum signature of the exemplary fluorochromes of the 25 color panel.
Figure 5C:
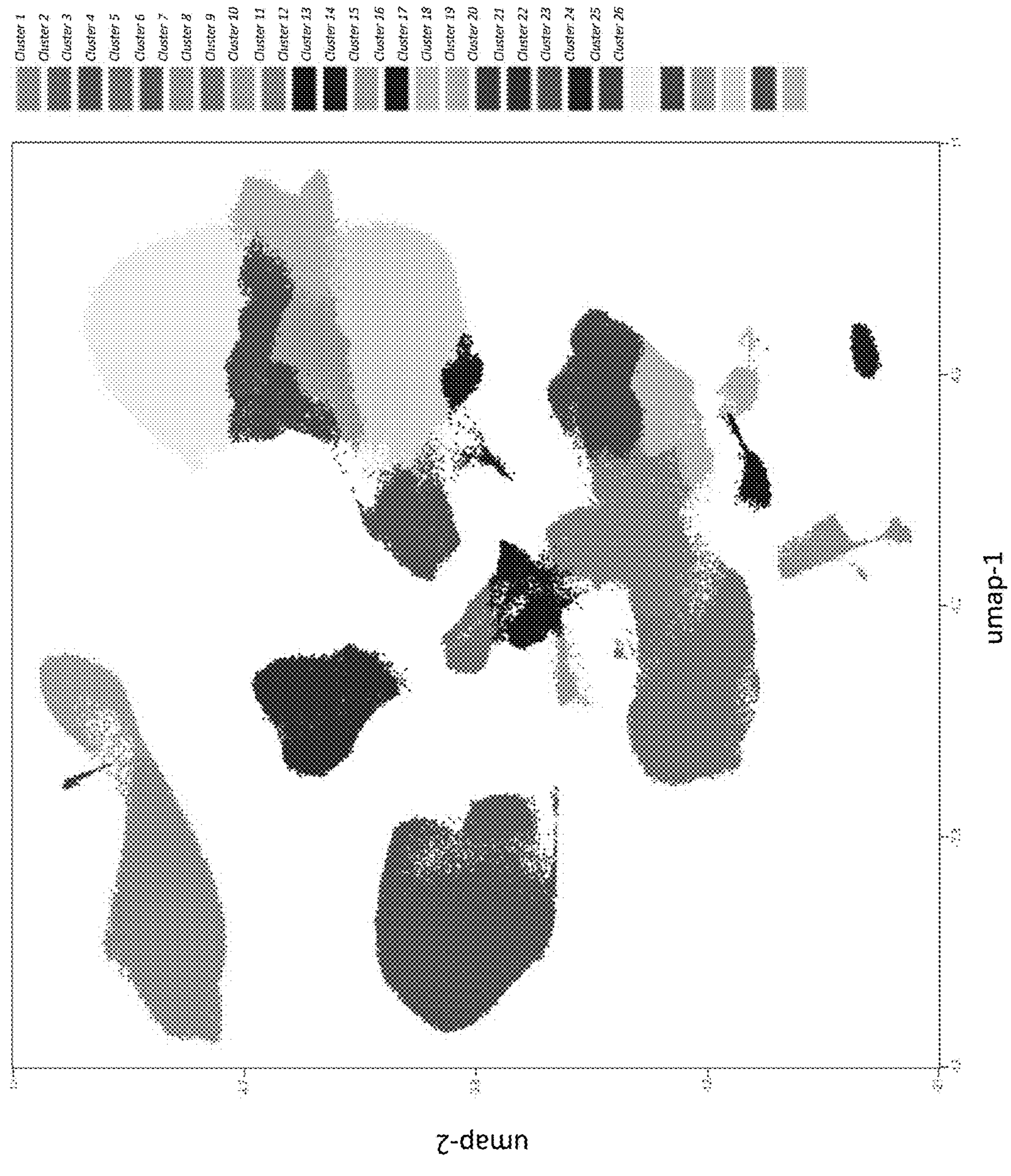
Figure 5D:
Figures 1, 5E:
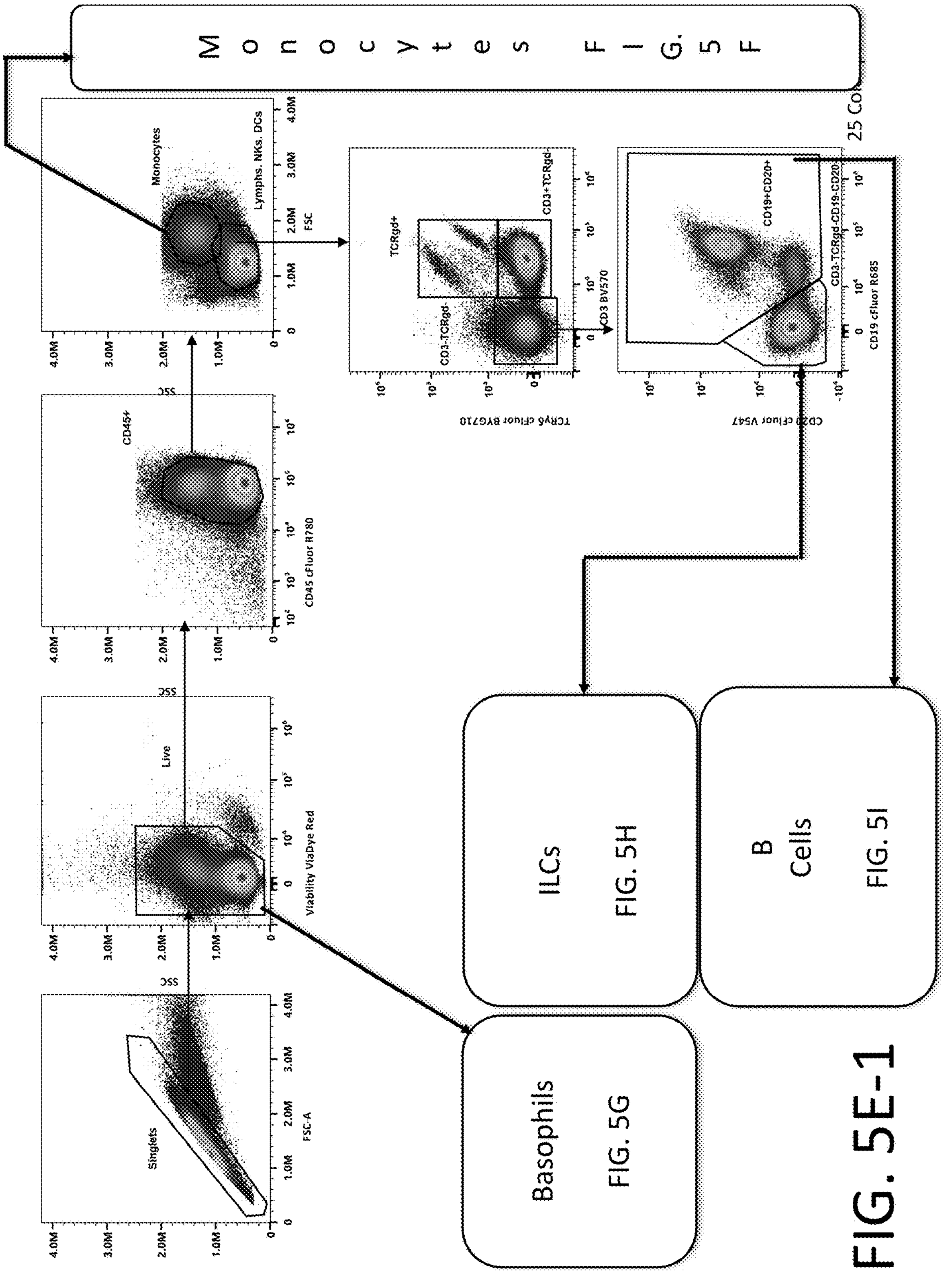
Figures 2, 5E:
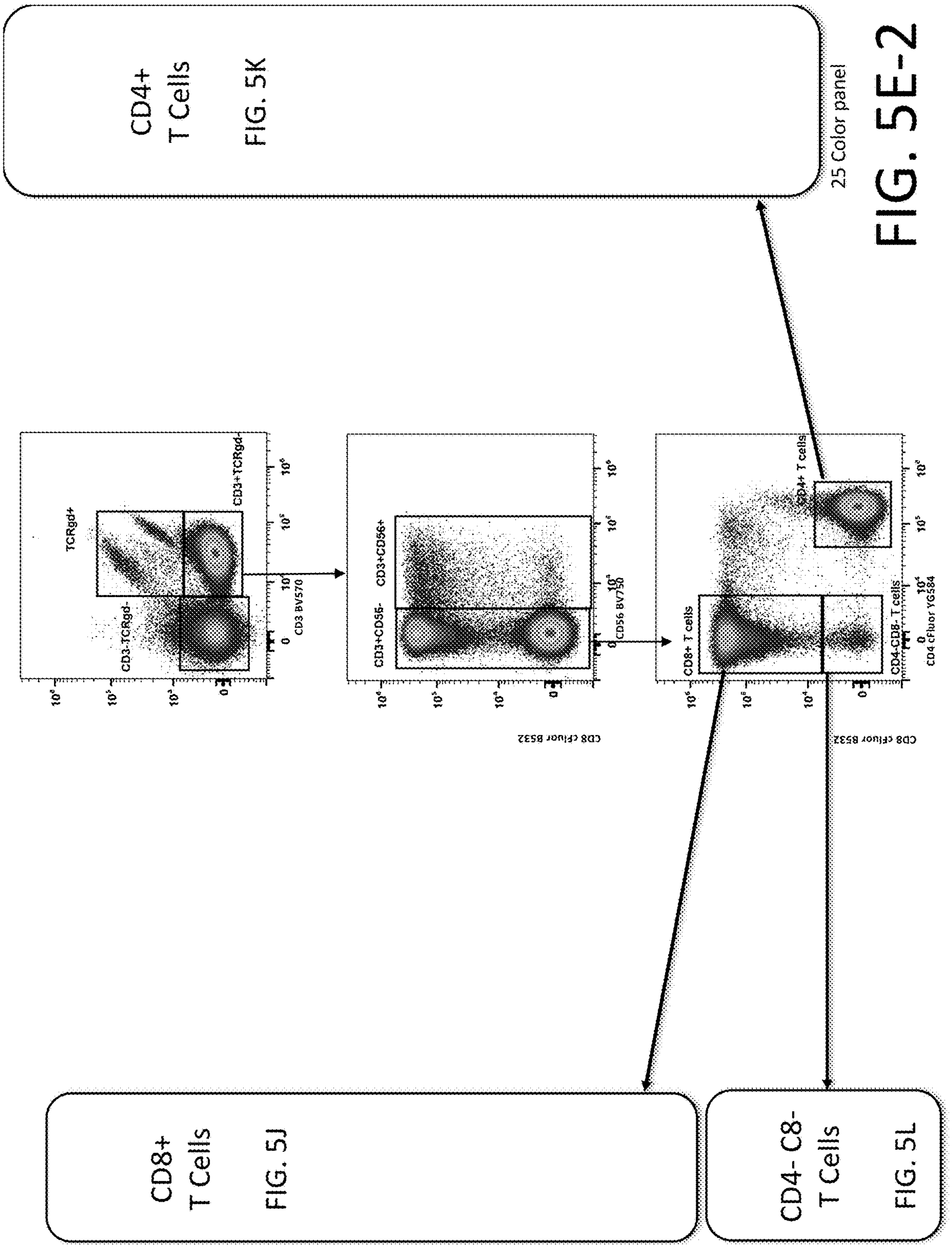
FIG. 2F shows configuration details of the photo detectors in the detector modules for a full spectrum flow cytometer.
Figures 3, 5E:
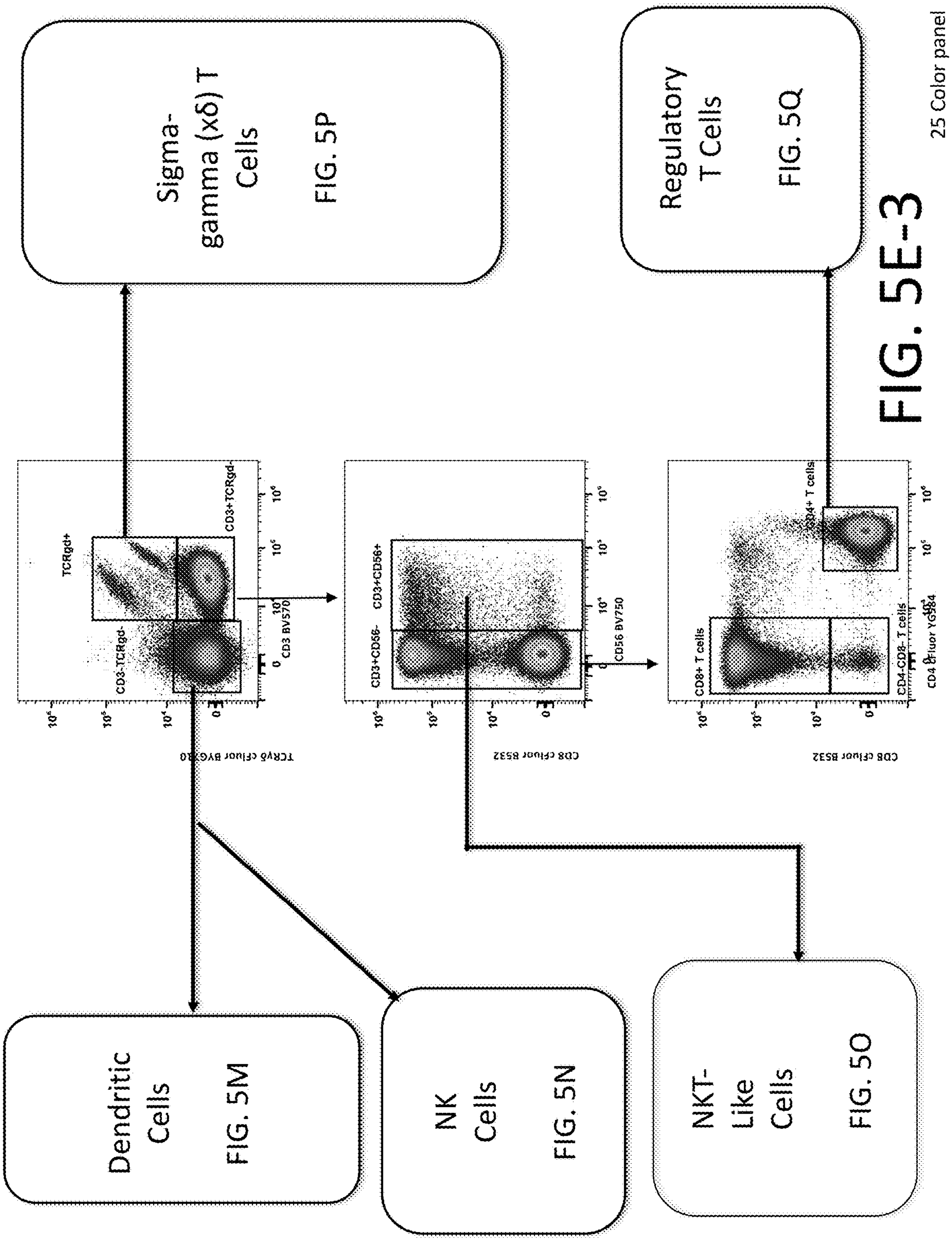
FIG. 3 is a listing of the exemplary cell markers and fluorochromes in a 28 color Optimized Multicolor Immunofluorescence Panel (OMIP).

A 28 color Optimized Multicolor Immunofluorescence Panel (OMIP) is illustrated in FIG. 3. The 28 color OMIP was developed using a full spectrum five laser cytometer as in embodiments of the invention. Markers are listed in the SPECIFICITY columns and corresponding fluorochromes are listed under the FLUOROCHROME columns. Markers and fluorochromes are further grouped under the laser that will optimally excite the fluorochrome.

Figure 4A:
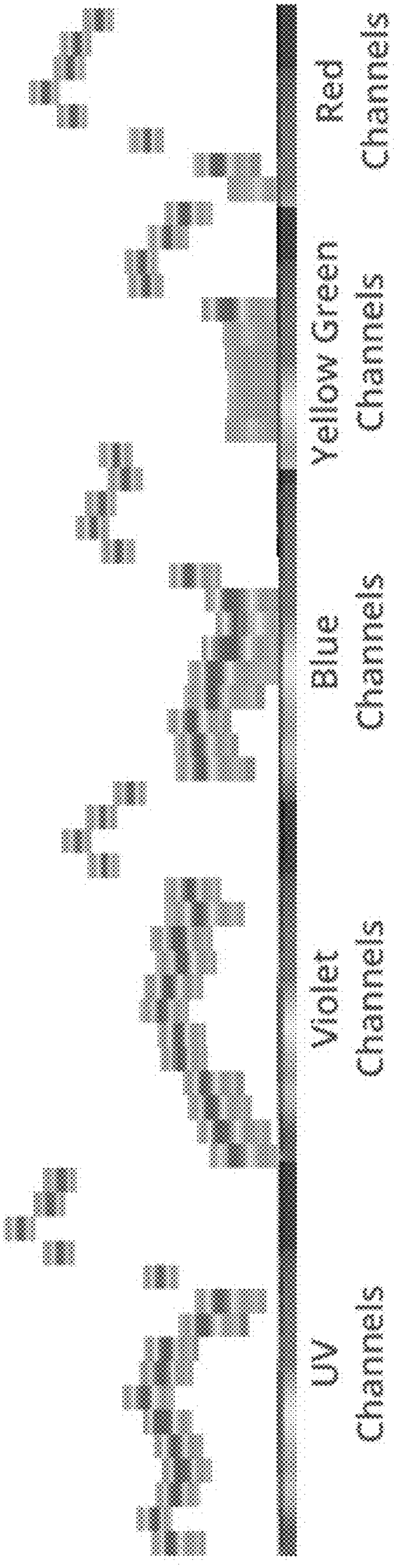
FIG. 4A illustrates the spectrum signature of BUV737.
Figure 4B:
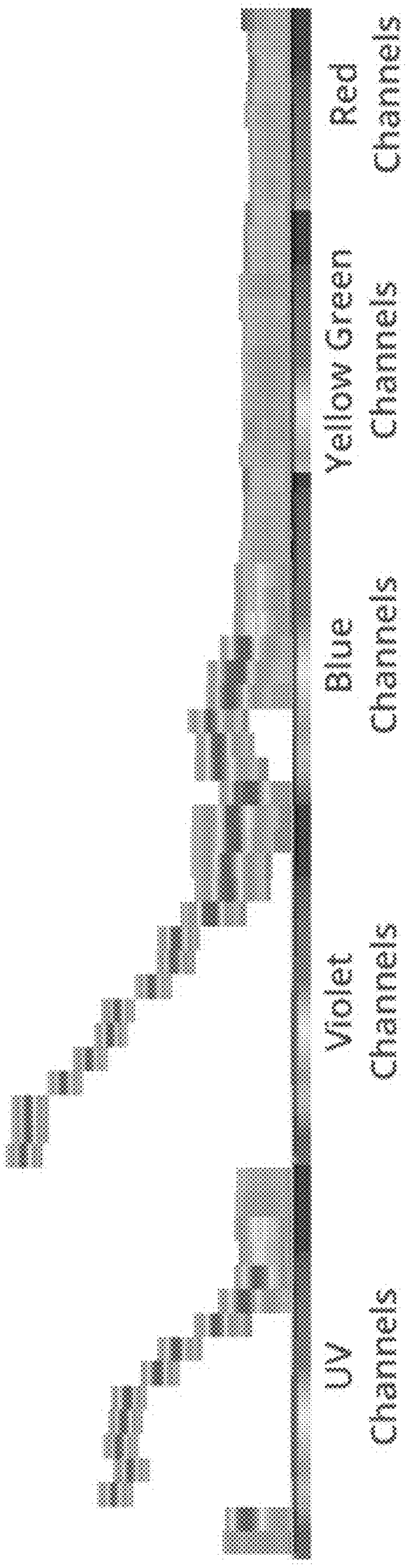
FIG. 4B illustrates the spectrum signature of BV421.

A UV laser adds an additional 16 fluorescence channels over the full emissions spectra, allowing the invention to extract even more information from each fluorochrome. The spectrum signature of BV737 and BV 421 are shown in FIGS. 4A and 4B respectively. In this example, 16 UV channels gives the BV421 spectrum signature a whole new look. The UV lasers allows for a more defined spectrum, allowing for more fluorochromes to be used in the same sample tube minimizing color bleed.

25 Color Panel

Figure 5F:
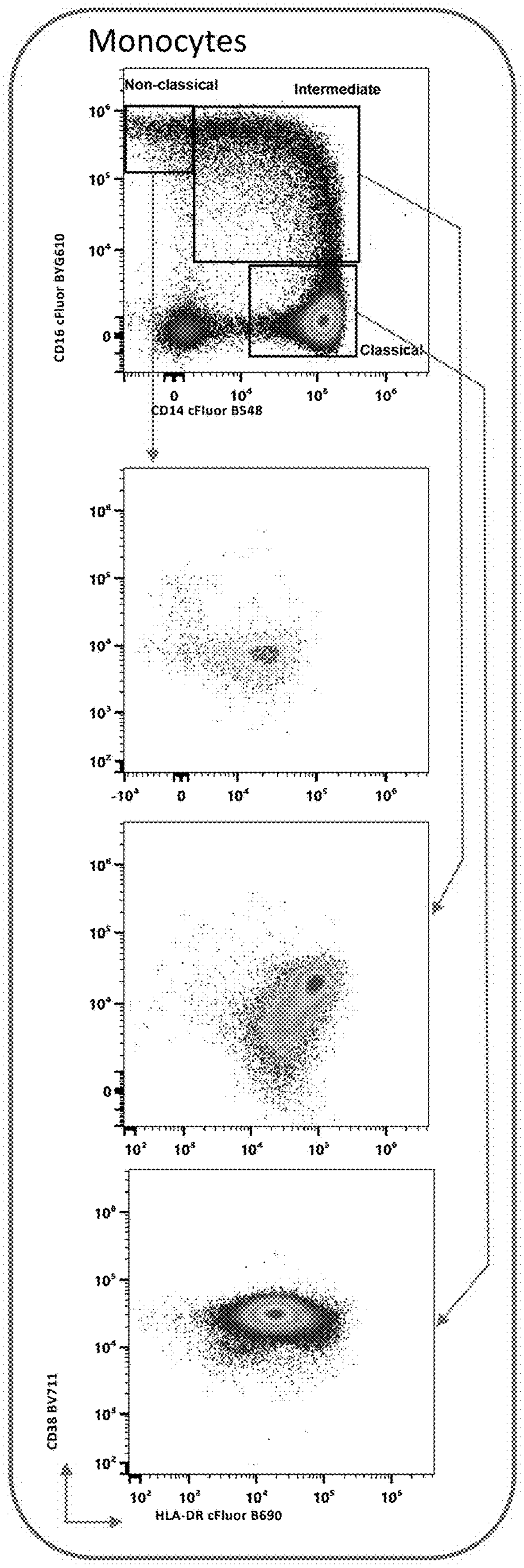
Figure 5G:
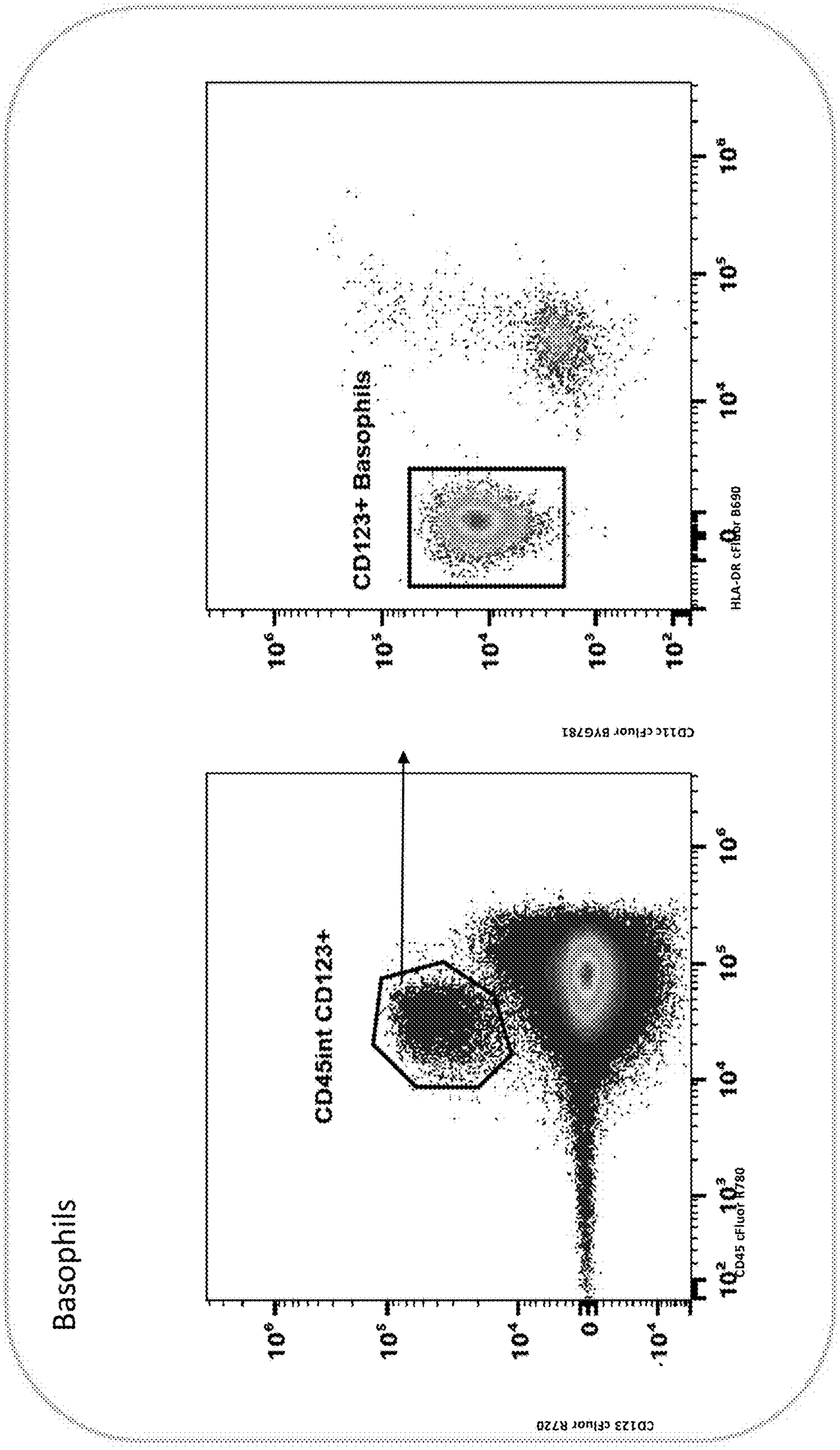
Figure 5H:
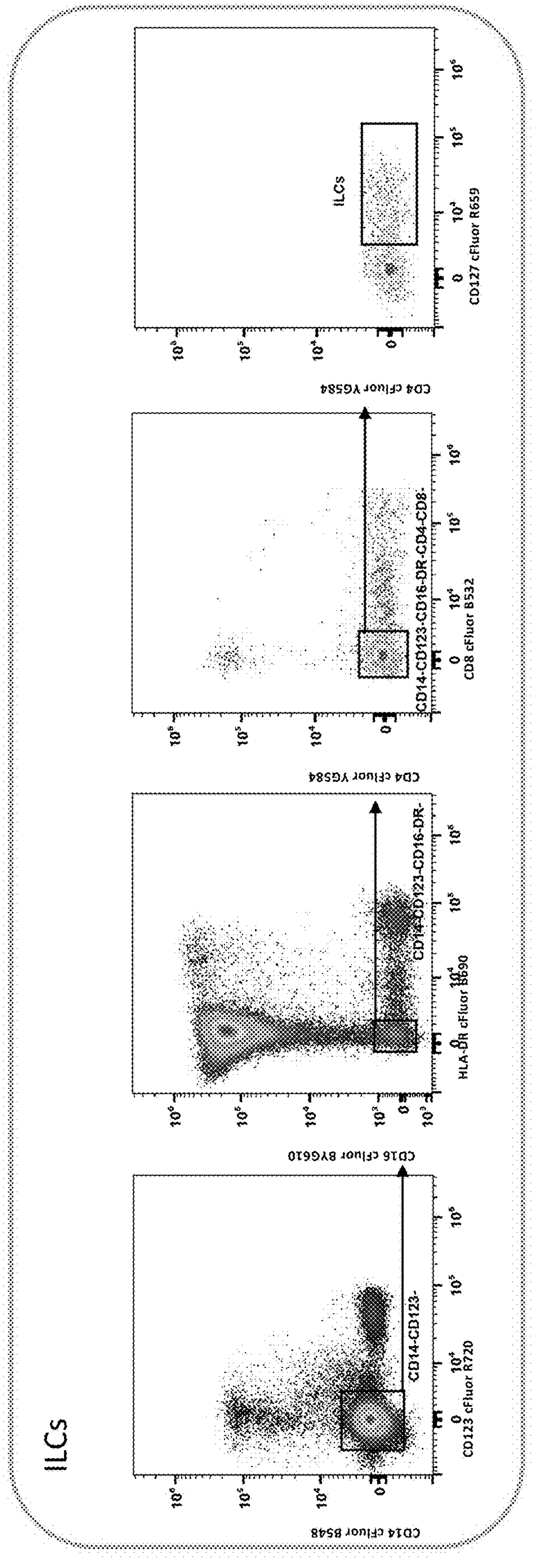
Figure 5I:
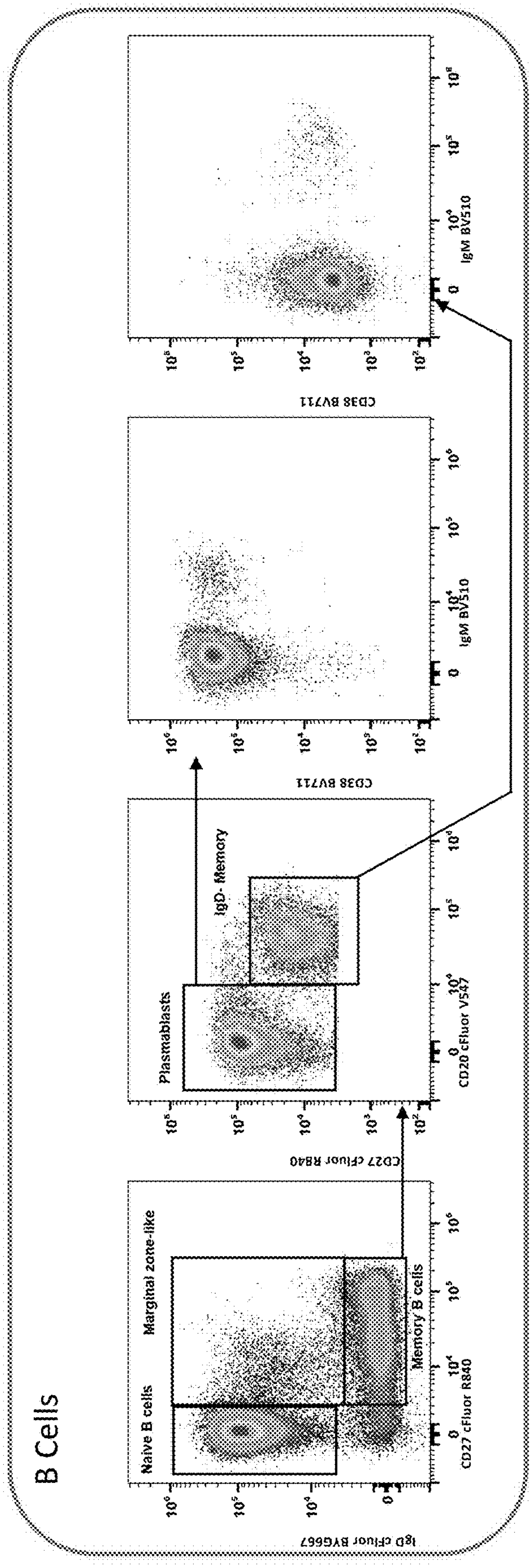
Figure 5J:
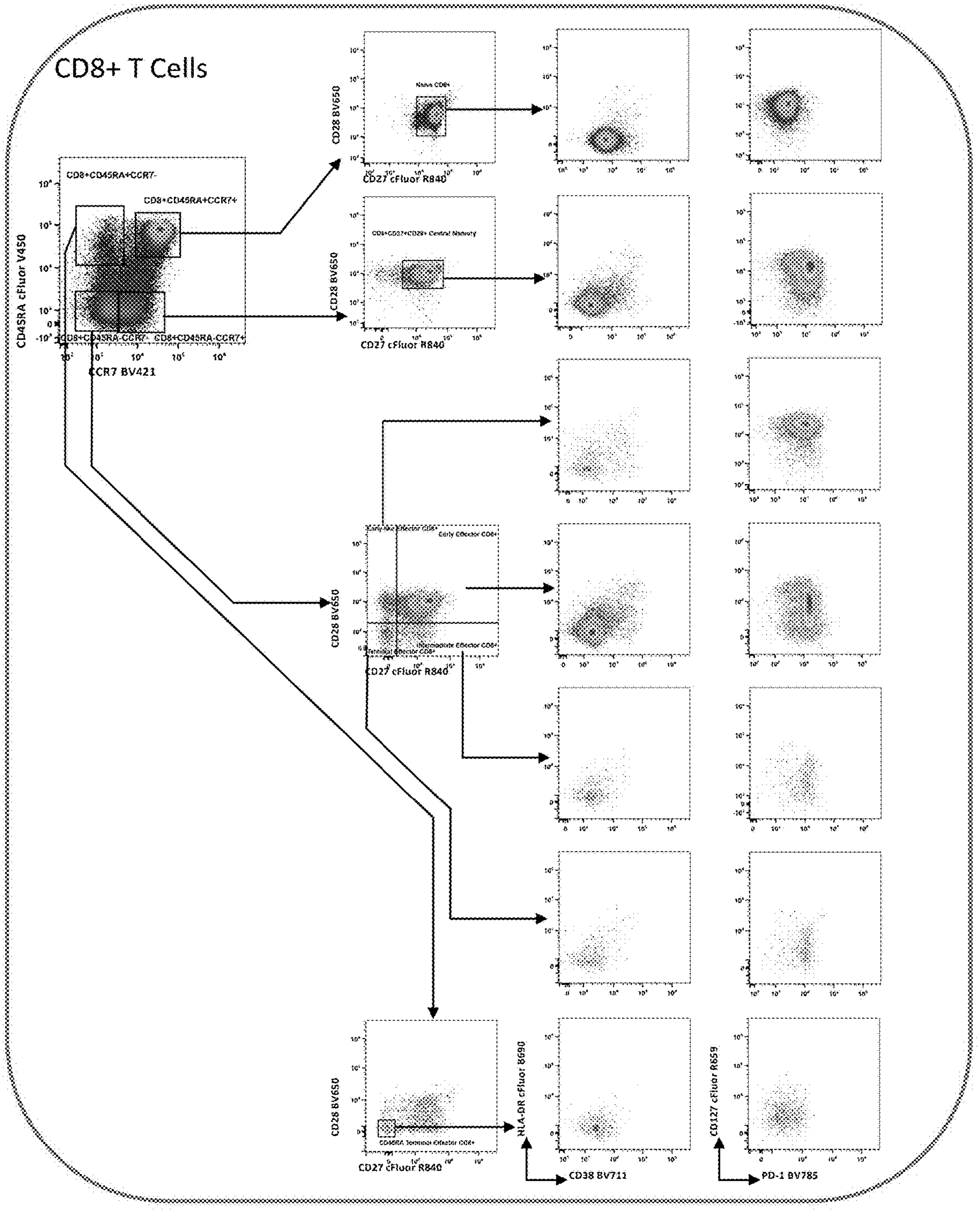
Figure 5K:
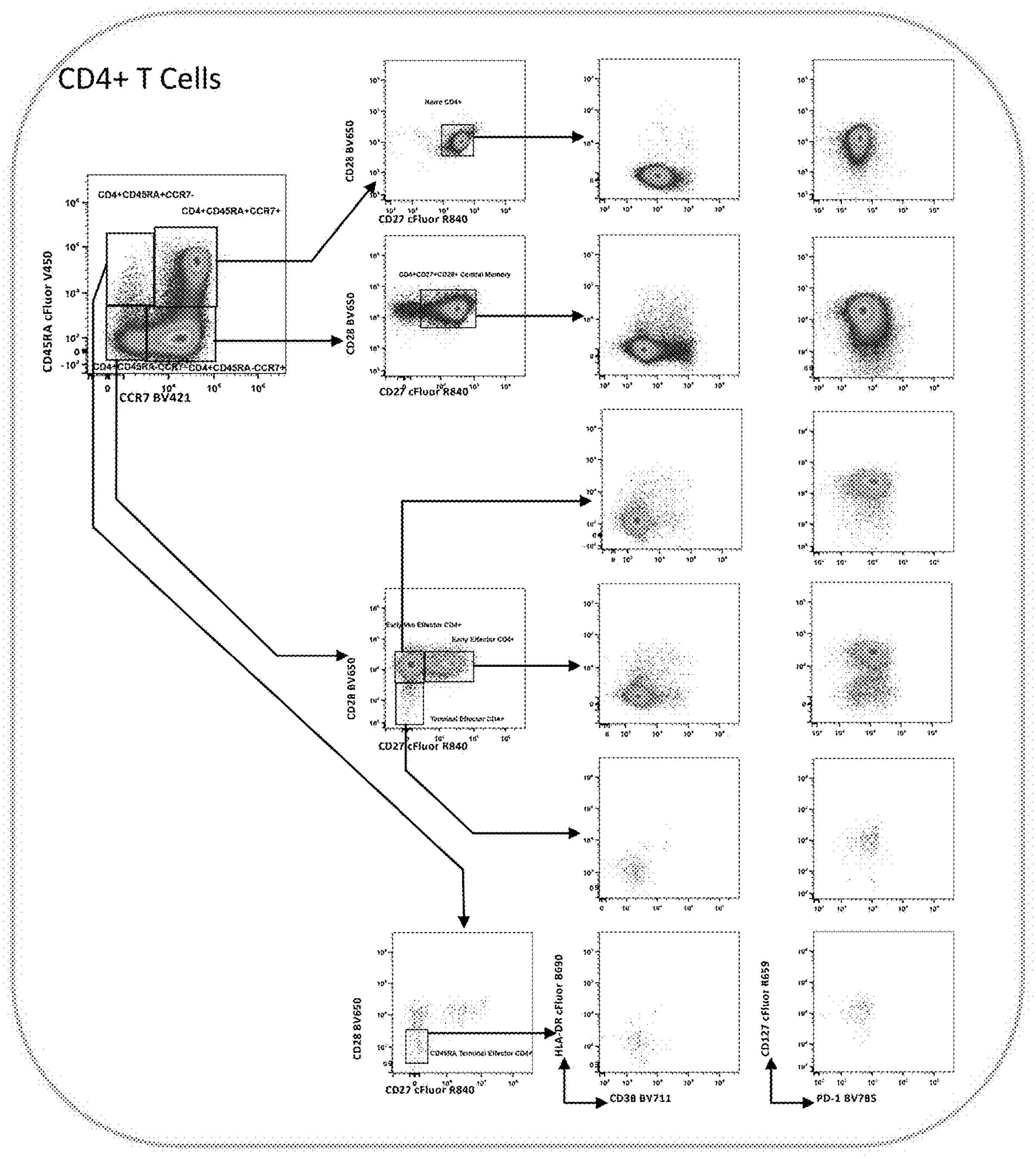
Figure 5L:
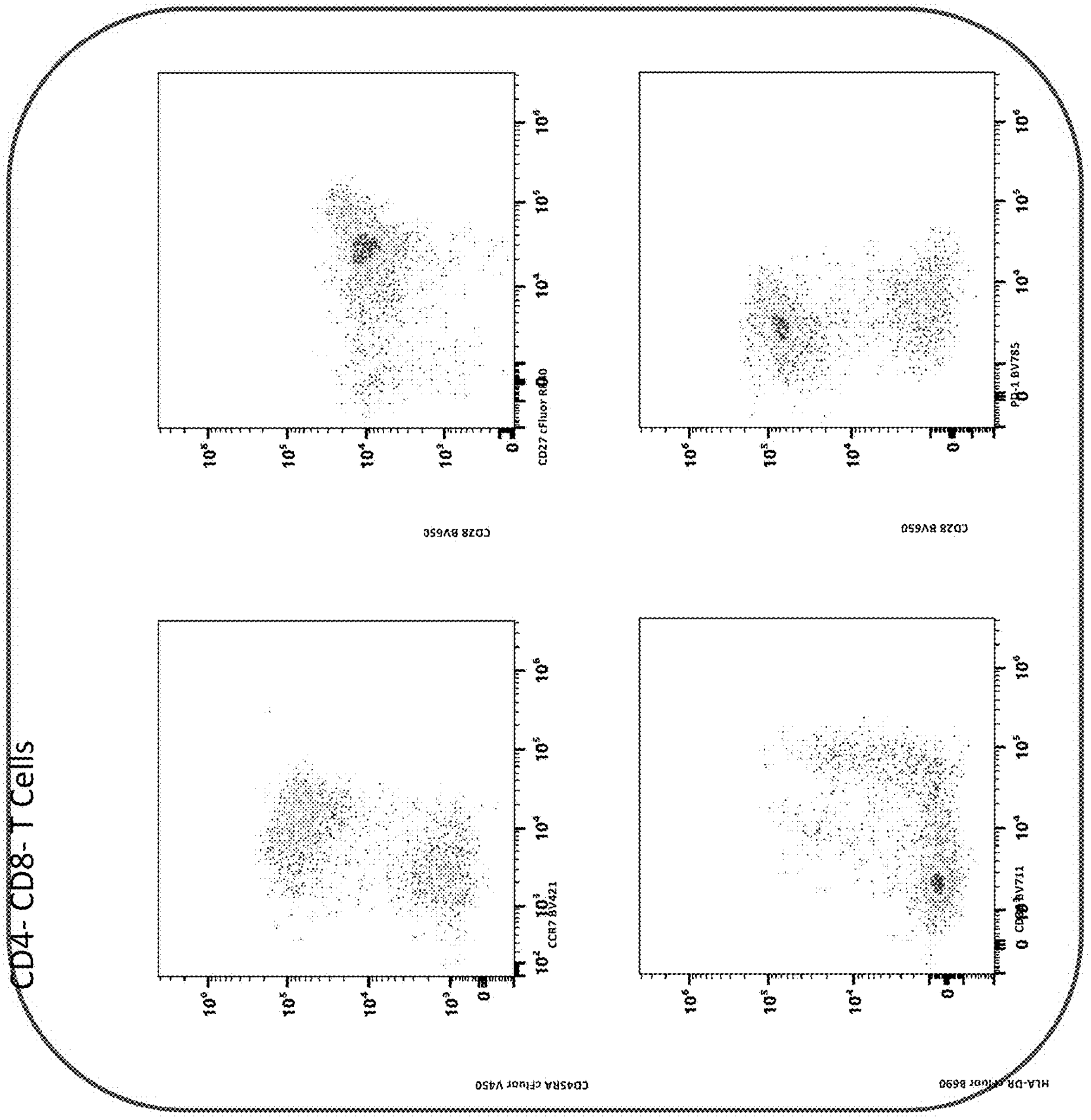
Figure 5M:
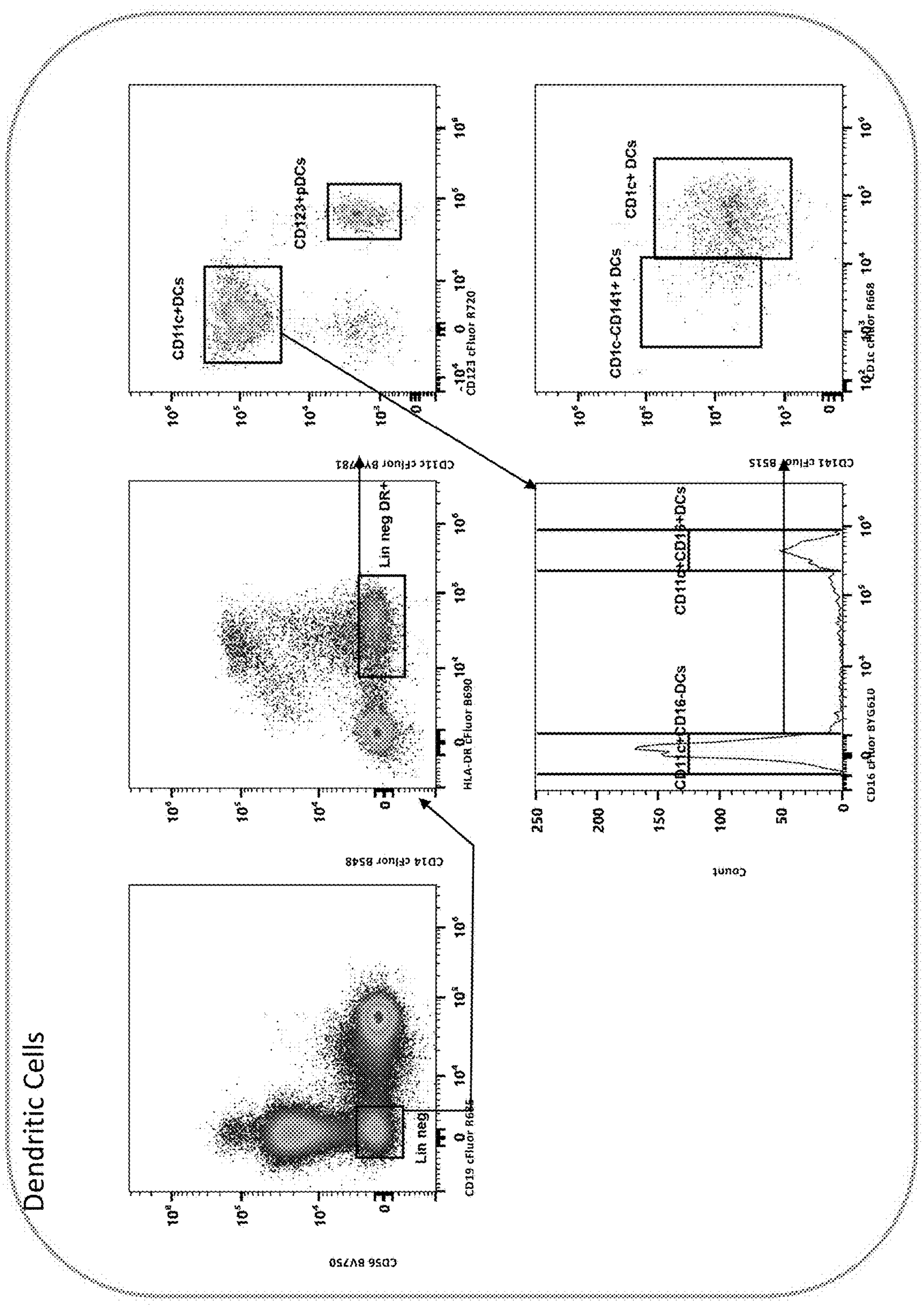
Figure 5N:
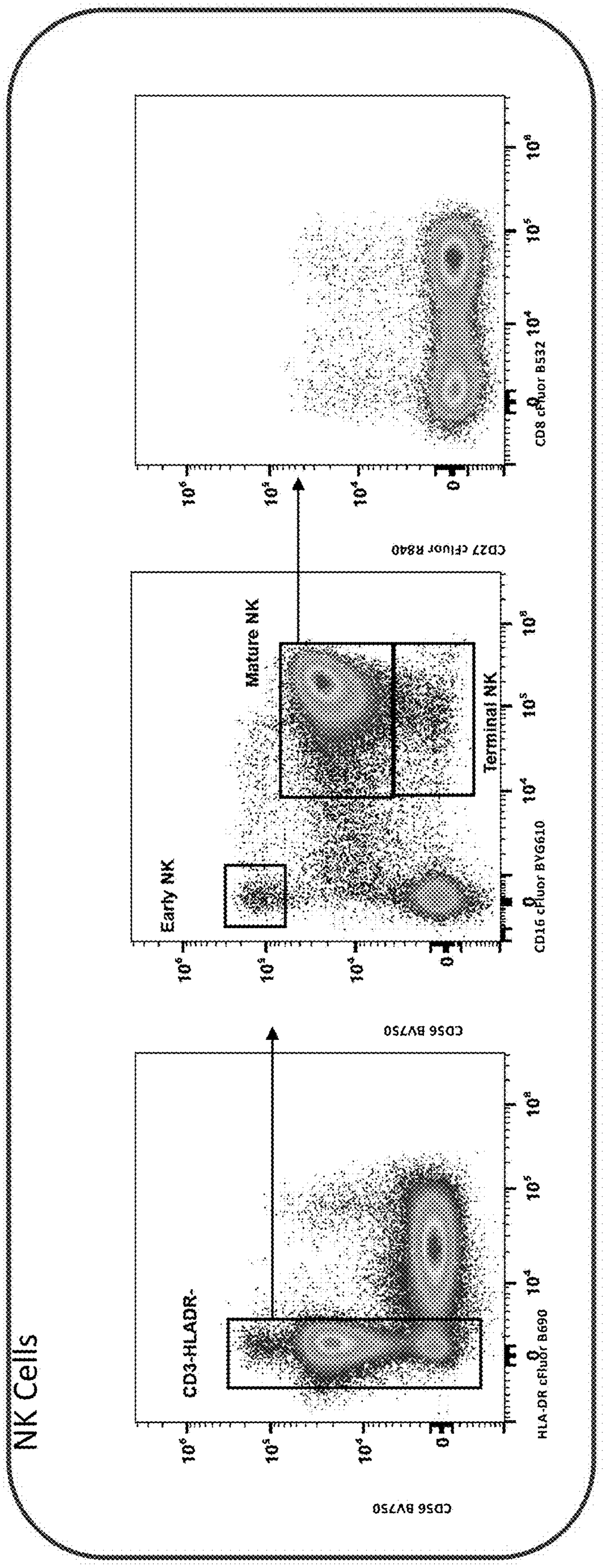
Figure 50:
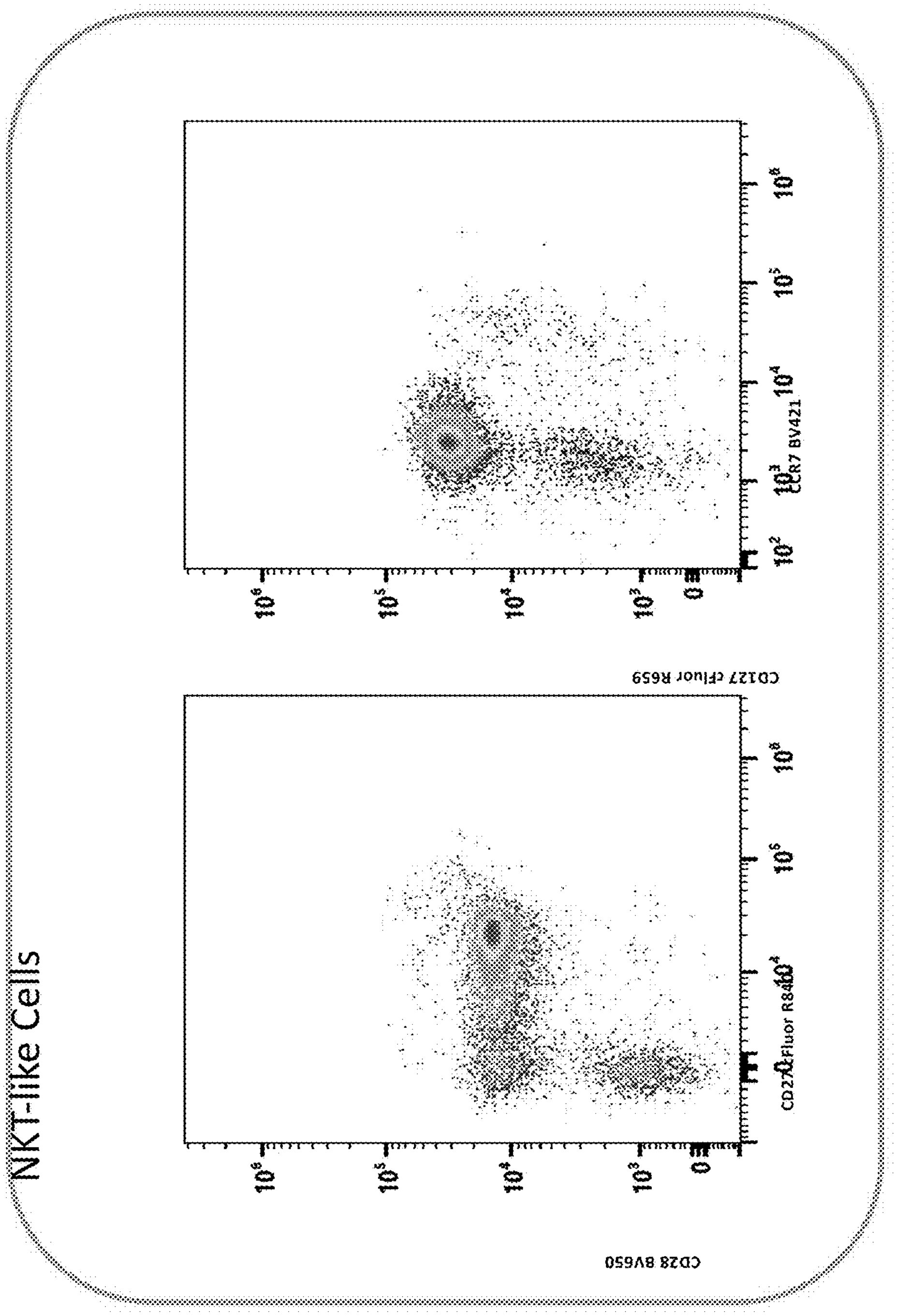
Figure 5P:
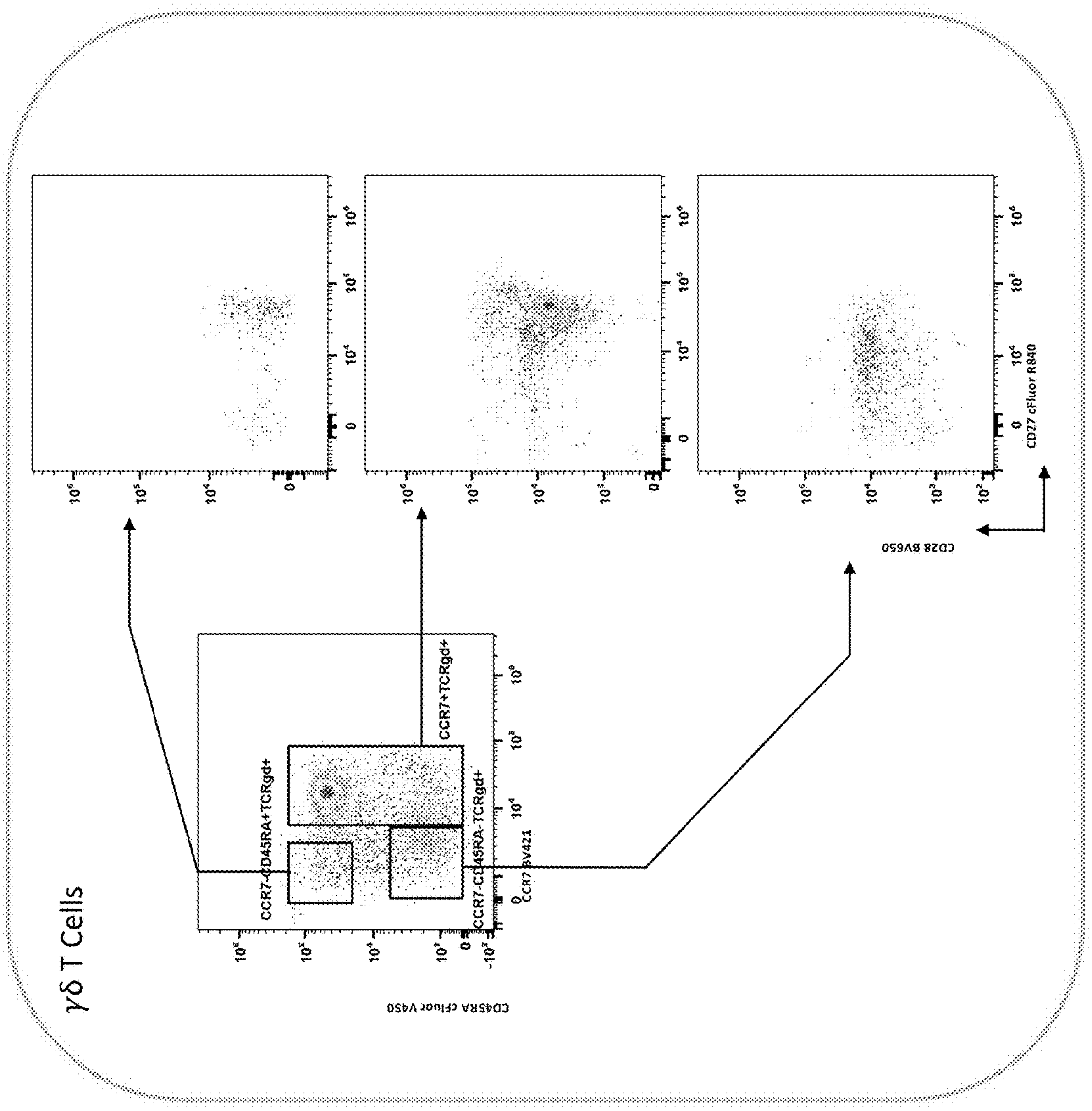
Figure 5Q:
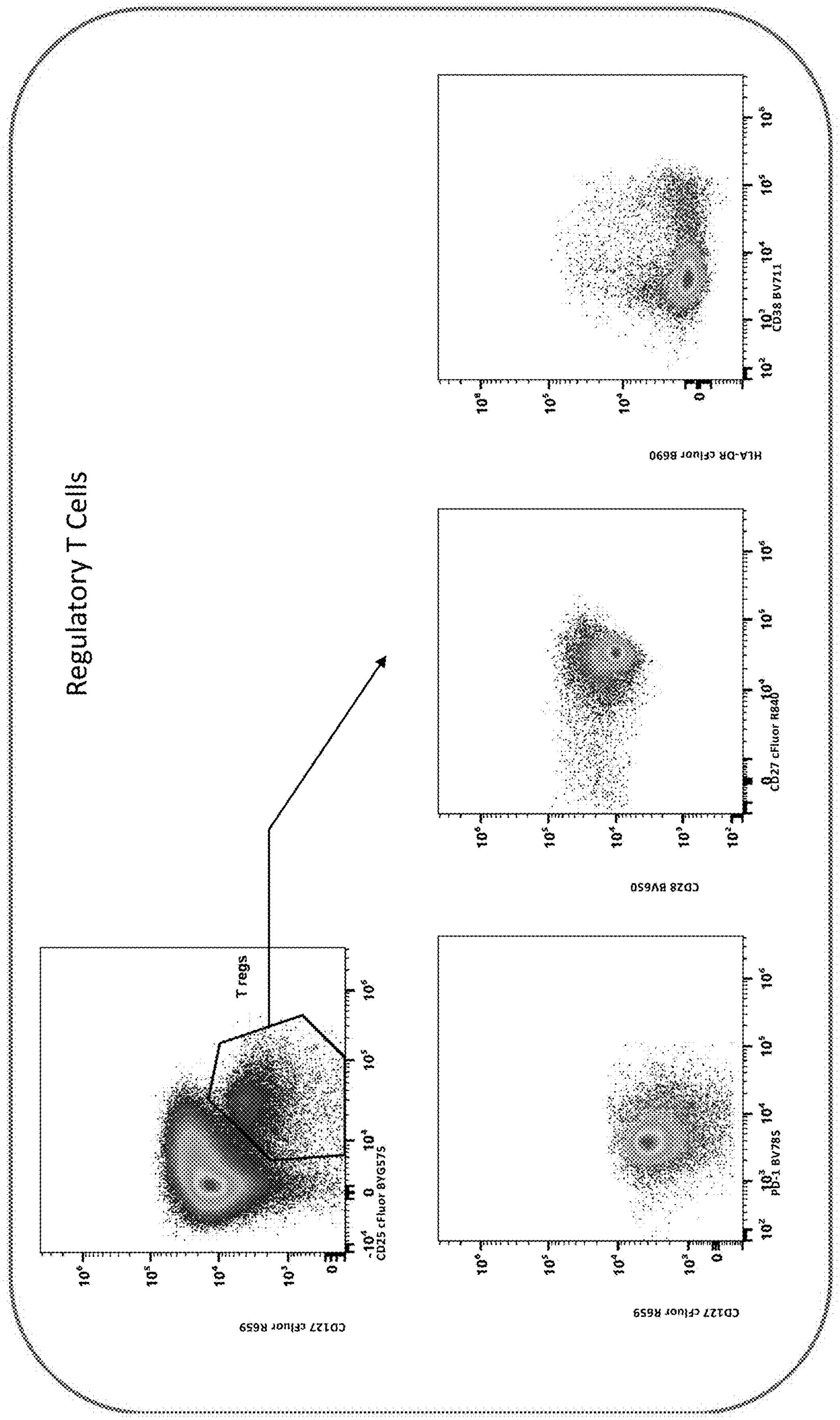

FIGS. 5A-5Q illustrate a 25-color immunoprofiling assay (panel) developed using a full spectrum flow cytometer with four lasers, violet laser, blue laser, yellow-green laser, and red laser. More lasers can be present, such as an ultra violet laser, in the flow cytometer but need not be used given their wavelength outputs are unlikely to cause the chosen fluorochromes to be excited. The markers and fluorochromes chosen for the 25-color panel are listed under their respective laser color in FIG. 5A. The 25-color immunoprofiling assay is designed and optimized to provide a turnkey solution for identifying major human immune subpopulations for T, B, NK cells, monocytes, dendritic cells, and basophils-all of which play important roles in the innate and adaptive immune response in various diseases. Human peripheral blood mononuclear cells were stained, washed, and acquired on a four laser full spectrum flow cytometer that can have sixty four (64) fluorescent detectors. The detectors for the ultra-violet laser are not needed for the 25-color panel, such that only 48 detectors were used. A clustering algorithm is used to detect and define cell populations.

Specifically, a t-SNE analysis of 25 colors immunophenotyping panel using OMIQ software (www.omiq.ai). was performed on the CD45+, singlets, and live cells. The clusters of cells are visually displayed in the heat map illustrated in FIG. 5B. Scaling was optimized and t-SNE analysis was done using GPU t-SNE algorithm for all donors (top row). One cell subset was present only in donor one (see arrow in top row). Colored-continuous scatterplots for donor one showing marker expression in this unique subset are shown in the second and third rows. Clustering analysis by FlowSOM visualized by GPU-tSNE, shows metacluster two expressing CD3+/CD4+/CD57±/PD-1±/CD45RO+/CD95±/CD56±/CD45RA−/CCR7−/CD27−.

In FIGS. 5E-5Q, two-dimensional (2D) dot plots organized by biological cell lines are illustrated for the 25-color panel. The marker and fluorochrome combinations shown in FIG. 5A were specifically chosen for optimal compatibility to detect cells in human blood with a spectrum flow cytometer having 4 lasers and 48 fluorescent detectors. Fluorochromes can be chosen with narrow excitation and emission spectra to reduce emission spectra overlap, when possible. Possible combinations are rigorously tested in a 25 color assay to determine their compatibility. In FIG. 5A, four tables, one for each laser color of the flow cytometer are shown for the 25 color assay. The four laser colors are violet, blue, yellow-green and red. Each table is further divided into three columns. The columns, from left to right, labeled specificity, clone and fluorochrome, identify the marker, the clone that targets that that marker, and the chosen fluorochrome respectively.

FIG. 5B illustrates a heat map of each marker after a clustering and dimensional reduction analysis is performed on the 25 color panel of FIG. 5A. Aside from making for impressive and artistic vendor posters, heat maps allow a quick overview of the entire panel at a glance, so visualizing multi-marker flow cytometry assays becomes easier.

In FIG. 5C the 26 metaclusters from the 25-color panel are visually illustrated. The visual representation of the 26 metaclusters were generated using a clustering algorithm. In this case a FlowSOM analysis was used. FlowSOM is a clustering algorithm for visualization of mass cytometry data. Clusters are arranged via a self-organizing map (SOM), in which events within a given cluster are most similar to each other, followed by those within an adjacent cluster. A second clustering step (i.e., meta-clustering) is subsequently performed, in which the clusters themselves are grouped according to similarity, and provides a basis for discerning biological similarity. In FIG. 5C, the FlowSOM is visualized as heat maps.

FIG. 5D illustrates a cluster heatmap illustrating marker expression of FlowSOM clusters of an exemplary group of 25 selected marker fluorochrome combinations. Rows and columns of a data matrix have been ordered according to the output from clustering.

FIGS. 5E-1 through 5E3, and 5F through 5Q are pseudo color dot plots of exemplary flow cytometry gating steps to characterize of cell populations that are identified with the 25-color panel as well as the markers (plots axis) used to characterize them. In FIG. 5E-1, the panels illustrate a series of gating steps to optimize the data and characterize populations of interest. From left to right, the first panel illustrate selecting for single cells by gating out or excluding doublets. A FSC singlet gate is placed to eliminate doublets. In the second panel, live cells are selected using a viability stain. Basophils can also be identified based on their low side scatter properties (see FIG. 5G). A CD45 gating is used to identify the major populations on a single plot. A leukocyte gate is placed on CD45 positive cells to define all CD45+ leukocytes. 'Lymphocytes, NKs, DCs' and 'Monocyte' gates are placed to further define the population.

Once a population of interest is identified, a more specific review of the marker expression on the selected population can be done on the gated population where two different markers are paired and assessed together. The Lymphs, NKs, and DCs identified in the fourth panel are further characterized by two conjugated markers in panels 5 and 6.

In FIG. 5F, the Monocytes from panel 4 are further characterized into Non-classical, Intermediate and Classical Monocyte subpopulations using a CD16-CD14 gating. FIG. 5G illustrates the further characterization of the Basophils population from panel 2, using double marker paring on a 25 color cytometer. Likewise, FIGS. 5H-5I illustrates characterizations of ILCs and B Cells, respectively, using double marker paring(s) on a 25 color cytometer.

Gating parameters for characterization of CD8+ T Cells, CD4-CD8 T Cells, CD4+ T Cells, using exemplary marker pairings on a 25 color cytometer is illustrated in FIGS. 5E2 and 5J-5L.

Gating parameters for characterization of Dendritic Cells, NK Cells, NKT-like Cells, Sigma-gamma (xδ) T Cells, and Regulatory T Cells using exemplary marker pairings on a 25-color cytometer is illustrated in FIGS. 5E3 and 5M-5Q.

Figure 5R:
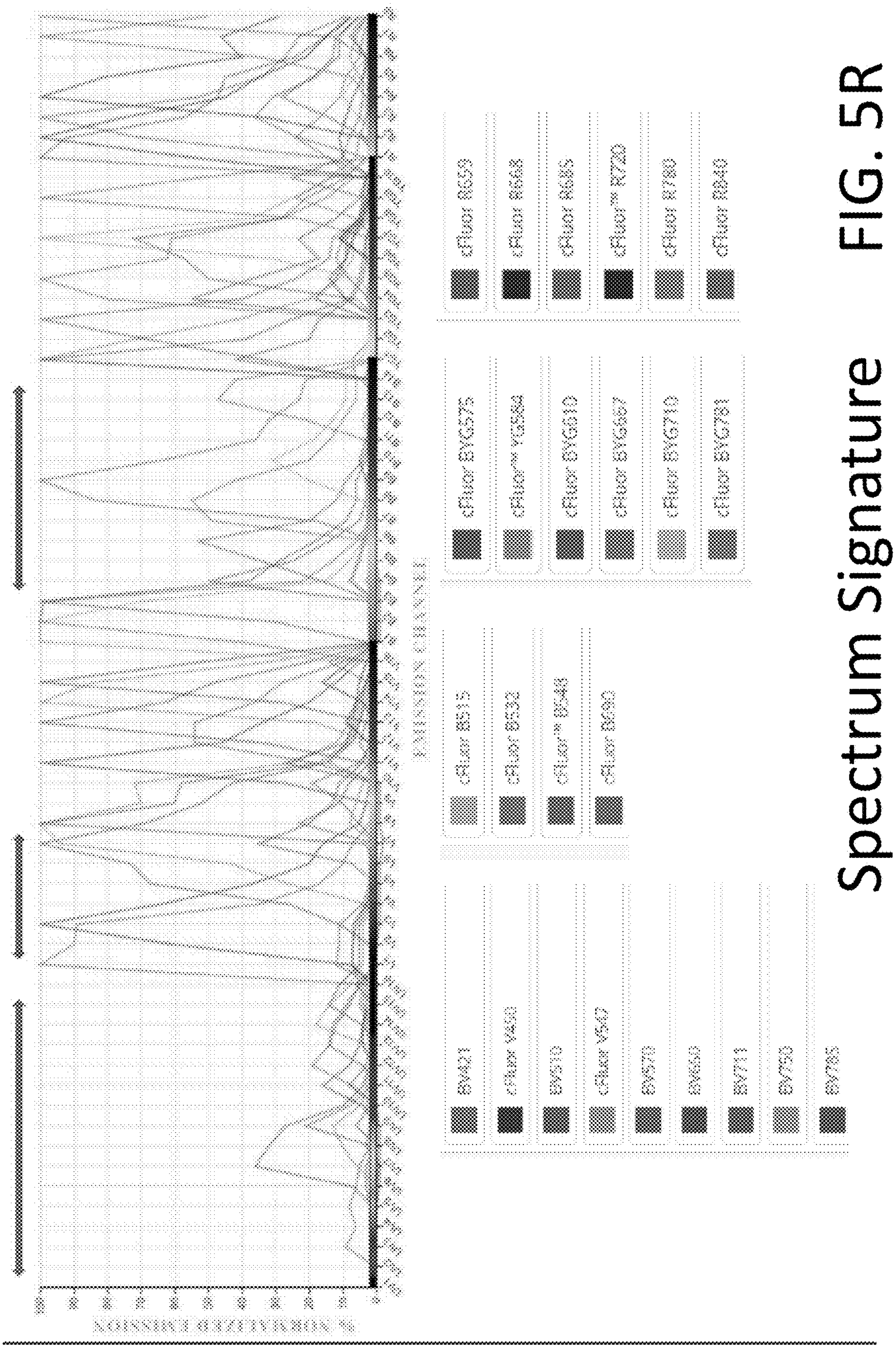

FIG. 5R illustrates the normalized emission spectra of the 25 reagents optimized for the best performance using a full spectrum cytometer with 5 lasers and 64 detectors. As can be seen in the graph, ultra-violet (UV) channels recorded low emissions and are not essential to the exemplary 25 color panel. The emission curves of the 25 exemplary reagents listed in FIG. 5R, showing their normalized emission and which channel each reagent spills into.

40 Color Panel

Until recently, developing fluorescence-based flow cytometry assays with 40 colors has been merely aspirational, with many turning to competing technologies for high-parameter applications. One embodiment of the invention with 64 fluorescence detectors and 5 lasers, is capable of resolving up to 40 colors in combination. A 40-color human immunophenotyping panel can be acquired from just a single tube sample, with outstanding resolution.

Data from a 40-color panel is illustrated in FIGS. 6A-6D. The fluorochromes and cell markers used in this exemplary 40 color panel is listed in FIG. 6A. This 40-color panel presents a powerful tool for in depth characterization of lymphocytes, monocytes, and dendritic cells present in human peripheral blood. It covers almost the entire cellular composition of the human peripheral immune system and will be particularly useful for studies in which sample availability is limited or unique biomarker signatures are sought.

FlowSOM and t-SNE-CUDA analyses were performed using OMIQ software on the data obtained from the 40-color panel. Doublets, aggregates, and dead cells were excluded from the analysis. 45 metaclusters were identified using FlowSOM.

Figure 6B:
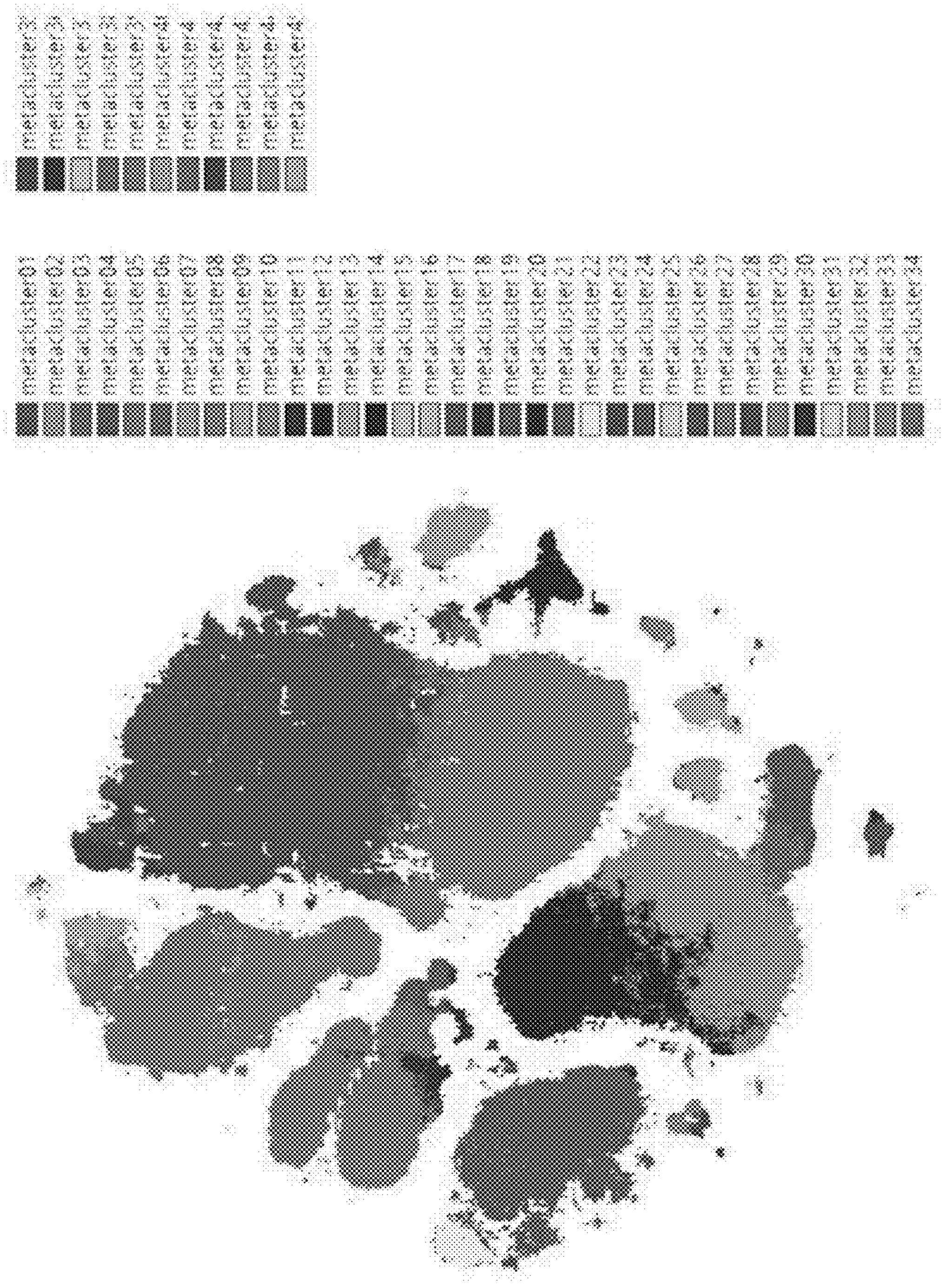

In FIG. 6B the 45 metaclusters from the 40-color panel are visually illustrated. The visual representation of the 45 metaclusters were generated using a clustering algorithm. In this case a FlowSOM analysis was used. FlowSOM is a clustering algorithm for visualization of mass cytometry data. FlowSOM clusters cells based on chosen clustering channels (or markers/features), generates a (Self-Organizing Maps) SOM of clusters, produces a Minimum Spanning Tree (MST) of the clusters, and assigns each cluster to a metacluster, effectively grouping them into a population. The FlowSOM algorithm outputs SOMs and MSTs showing population abundances and marker expression in various formats including pie charts, star plots, and channel-colored plots.

Figure 6C:
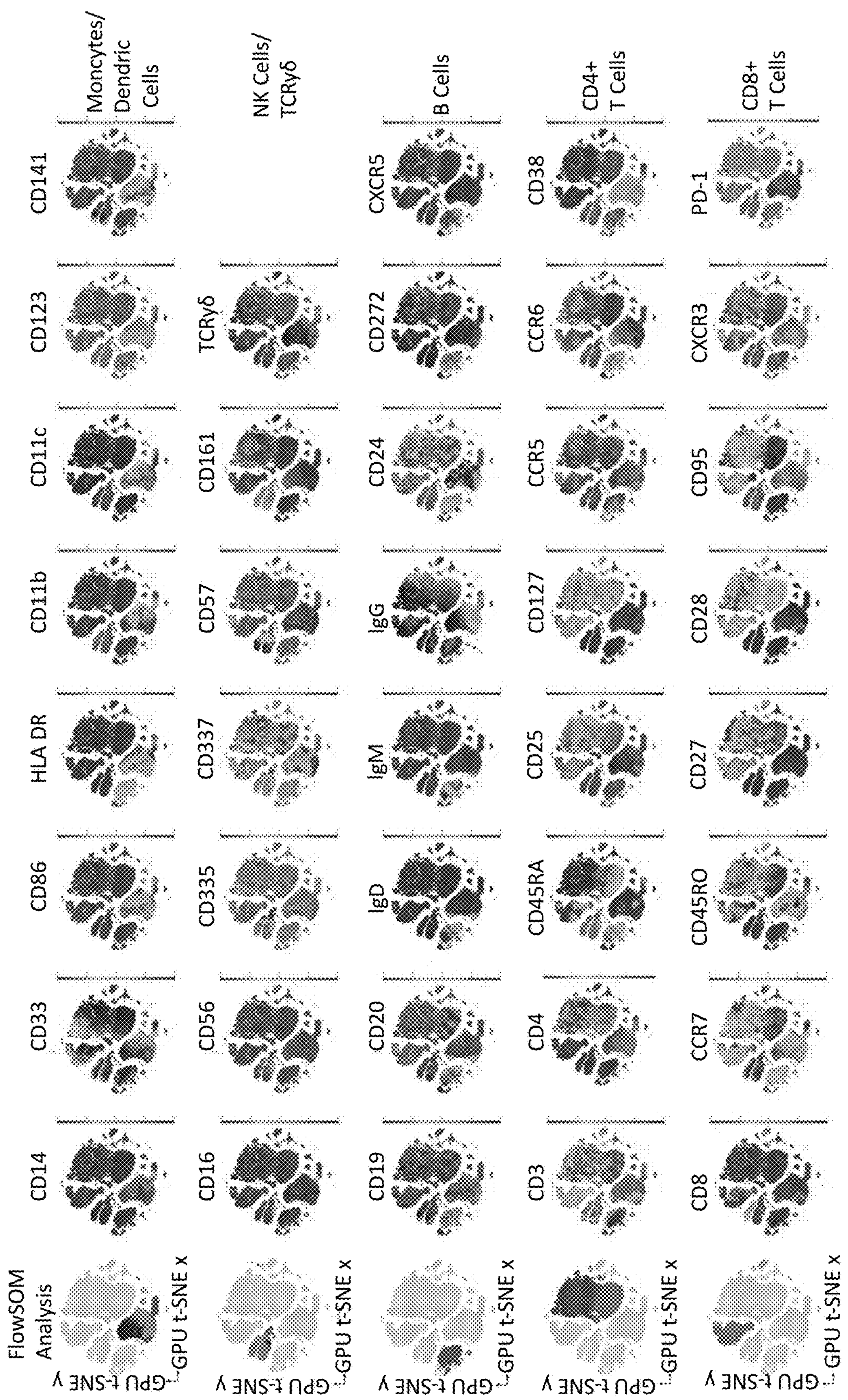

In FIG. 6C, t-SNE-CUDA plots colored by marker expression are presented. The markers are organized by major cell subsets.

Figure 6D:
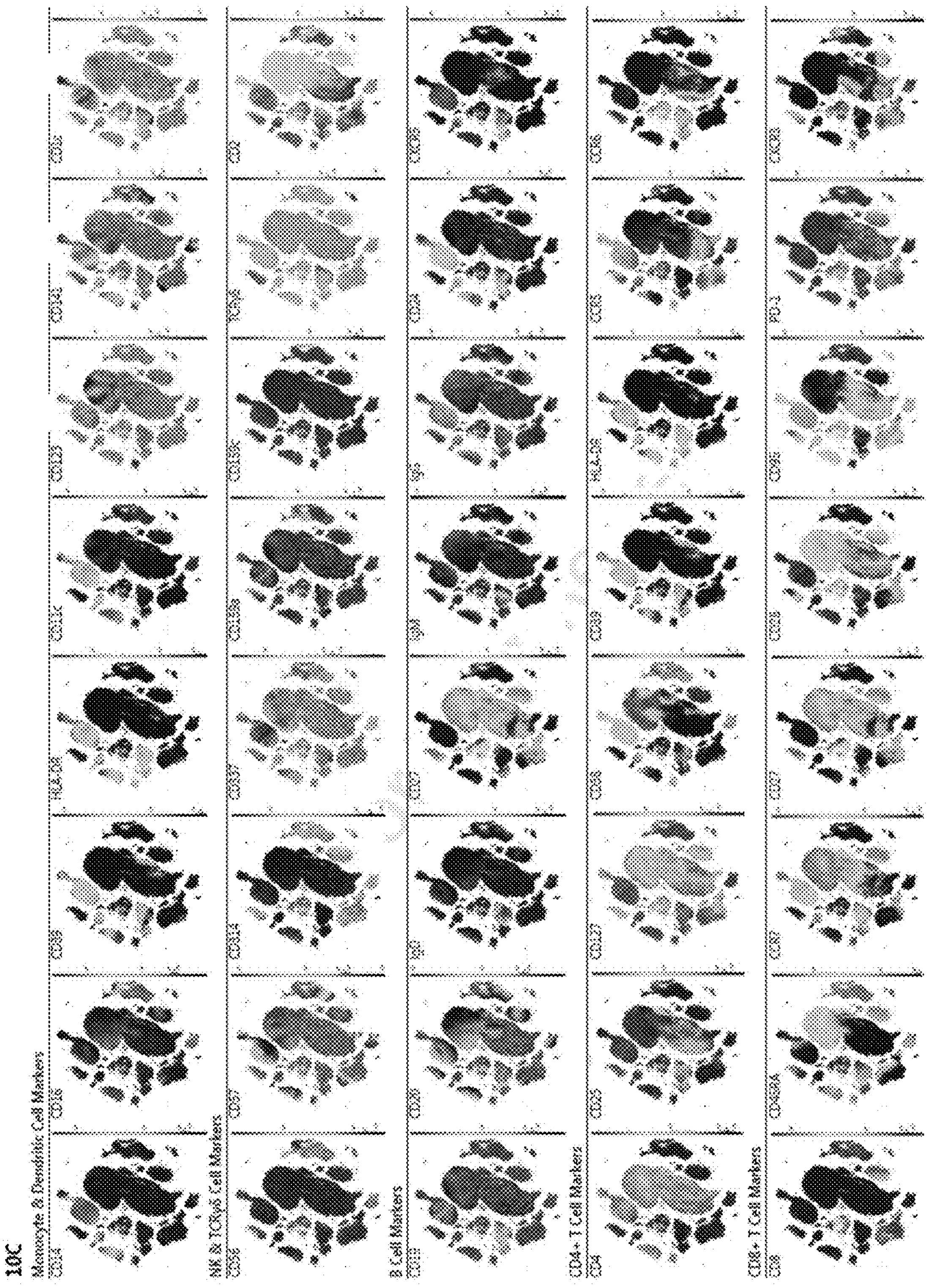

FIG. 6D illustrates a high dimensional data reduction of a 40-Color Panel overview showing the expression of phenotypic markers on PBMCs in several unsupervised analyses to illustrate differences between two donors and their respective populations. (A) Hierarchically clustered heatmap displaying the marker expressions of manually labeled FlowSOM clusters from both samples concatenated. (B) FlowSOM metaclusters visualized on opt-SNE coordinates from each donor. Metaclusters that were similar enough to be part of the same sub-population were combined into a single labeled population. (C) Visualization of the phenotypic variation across all PBMC subsets using opt-SNE. Marker expression intensity is indicated by the scale bar to the right of each plot where red is high, and blue is low.

The cell subsets are identified in the last column. Besides making for an impressive and attractive display, the FlowSOM analysis allows clusters to be assembled into commonly recognized biological populations. The heatmaps generated with the resulting populations are clustered hierarchically to indicate the similarity of the populations. This allows the FlowSOM clusters to be verified and translated into well-recognized classical populations via the heatmap, then visualized on the opt-SNE parameters for case of comparison.

In order to build a 40-color panel, the best possible 40 fluorochrome combination has to be identified. The spectra of over 65 commercially available fluorochromes are analyzed. The use of commercially available fluorochrome is more efficient, but in-house produced fluorochromes can also be used and is within the scope of the invention. Fluorochromes with peak emissions occurring in different channels were identified, as well as fluorochromes that, despite sharing the same peak emission, have a different spectrum.

Figure 7A:
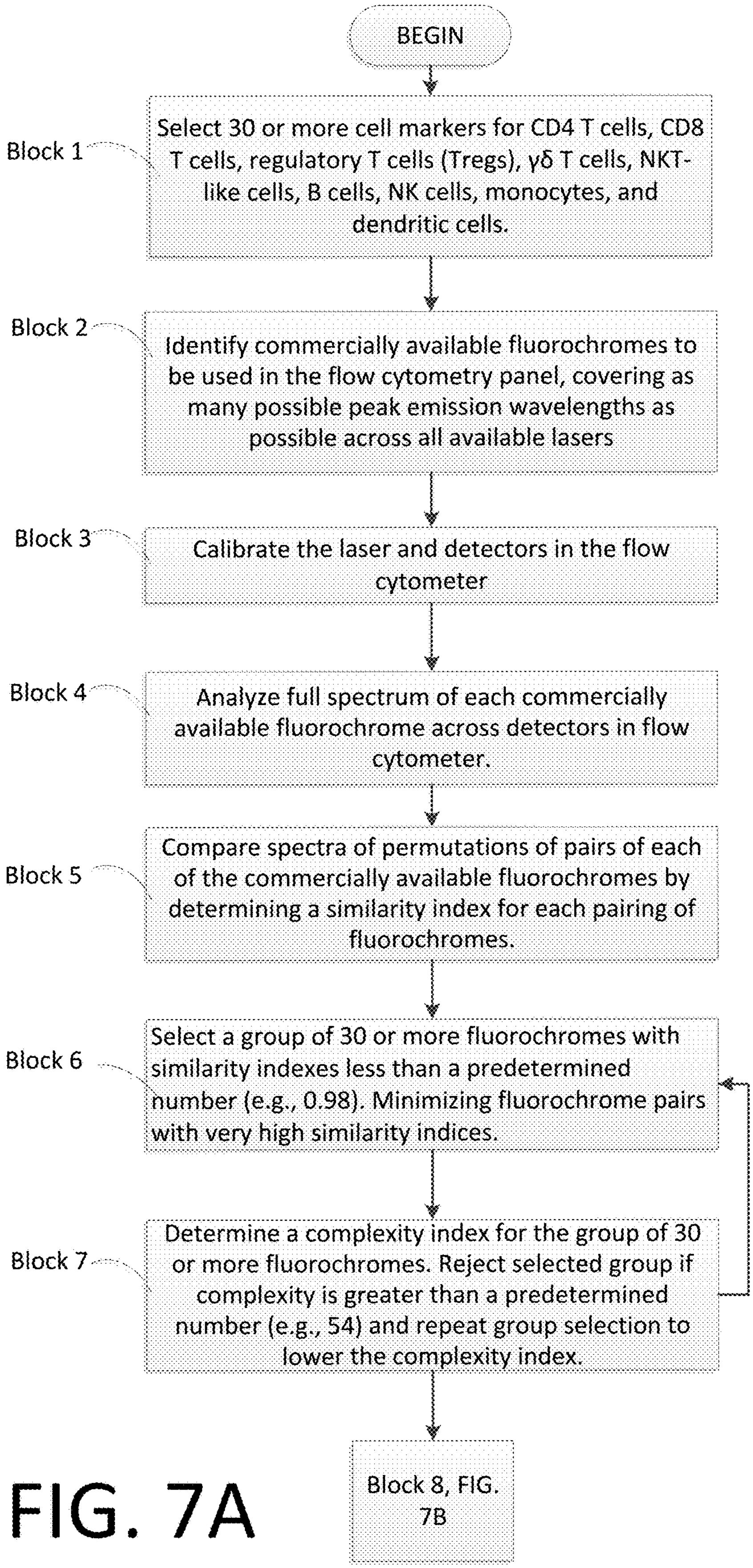
FIGS. 7A-7B is a flowchart detailing the method steps for building a 40-color panel according to an embodiment of the invention.
Figure 7B:
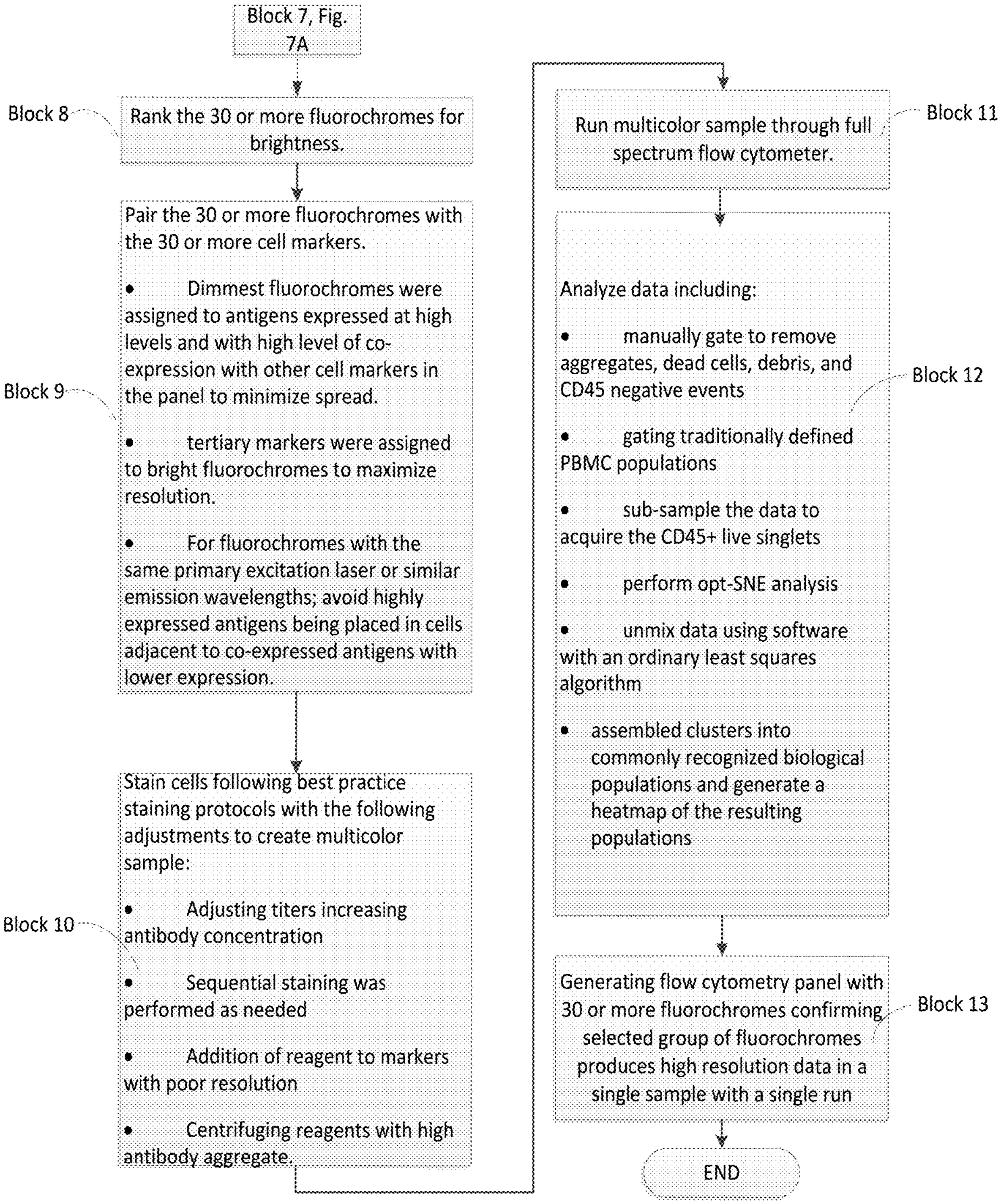

FIGS. 7A-7B is a flowchart detailing the method steps for building a 40-color panel according to an embodiment of the invention.

In block 1, of FIG. 7, 30 or more cell markers are selected from cell lines such as CD4 T cells, CD8 T cells, regulatory T cells (Tregs), γδ T cells, NKT-like cells, B cells, NK cells, monocytes, and dendritic cells. The cell markers are selected from cell lines that can be used for studies aimed at characterizing the immune response in the context of infectious or autoimmune diseases, monitoring cancer patients on immuno- or chemotherapy, and discovery of unique and targetable biomarkers.

In block 2, commercially available fluorochromes to be used in the flow cytometry panel are identified, covering as many possible peak emission wavelengths as possible across all available lasers. 65 commercially available fluorochromes were selected to be further analyzed.

In block 3, a full spectrum cytometer with 5 laser and 64 detectors is calibrated for use. This panel was developed on a flow cytometer equipped with 5 lasers (355, 405, 488, 561, 640 nm) and 64 detectors. Gains of the detectors is variable and can be set such that each fluorochrome's peak emission channel corresponds to their maximum emission wavelength and the spectral patterns do not exhibit steep changes from one channel to the next.

To accommodate brighter signals (due to antigens with higher expression level, differences in expression level across donors, or up-regulation of receptors), PBMCs stained with anti-CD8 labeled with each fluorochrome were acquired at the optimal gains established in the previous step and signals verified to be on scale (<2×106 on a full scale of 4×106). If needed, gains of the detectors were adjusted proportionately across the detectors to put the brightest signals on scale.

To identify gains which had the least impact on spillover spread, we compared spread values based on the Spillover Spreading Matrix (SSM) at different gains; using the gains established in the previous step, and with a 2- and 4-fold increase, to ensure the lower gains of the detectors minimized spread values.

The final gain settings for the detectors is saved in the SPECTROFLO software as a saved assay setting. These gain settings can be automatically updated during daily quality control (QC) based on calibrated bead MFI targets to ensure consistent setup across days that the flow cytometer is used.

A schematic of the optical layout for a 5-laser flow cytometer was shown in in FIG. 2E. The full spectrum flow cytometer used to develop the panel was equipped with 5 lasers. The optical paths for each of the 5 lasers (UV 355 nm, Violet 405 nm, Blue 488 nm, Yellow Green 561 nm, and Red 640 nm) are represented. The lasers are spatially separated, each has an independent optical path to the flow cell to strike particles/cells at slightly different times as they flow by in the sample fluid. A portion of the various types of light (e.g., scattered, fluorescence, autofluorescence) generated by each laser strike upon the particles/cells is received and directed through optical fibers to individual detector modules having an arrays of avalanche photodiodes (APD) as photodetectors.

In block 4, the full spectra of each commercially available fluorochrome is analyzed across all detectors in the flow cytometer. The signature spectra of each fluorochrome is recorded for further comparison in the next method steps.

In block 5, the commercially available fluorochromes' signature uniqueness, determined by comparing the full spectrum across all 64 detectors, was quantified using a similarity index available in the SPECTROFLO software. The spectra of permutations of pairs of each of the commercially available fluorochromes are compared by determining a similarity index for each pairing of fluorochromes.

The similarity index can use the cosine of the angle between the vectors defined for each fluorochrome in a 64-dimensional space to compare two signatures. This index ranges from 0 to 1; 0 indicating the 2 fluorochromes do not share any spectral characteristics, and 1 indicating that the spectra are identical. Based on testing of multiple fluorochrome combinations, it was determined that similarity indices of 0.98 or less indicated that fluorochromes were different enough to be used together. Similarity indexes are discussed in more detail below.

Results of the Similarity Index Matrix (SIM) which measures how similar two spectra are to each other are is illustrated in Figure V7A. A value of "1" indicates there is virtually no difference between 2 fluorochromes, while a value of "0" indicates two fluorochromes are completely unique. The chart displays the numerical value for each pair of fluorochromes identified for use in the panel. Based on the testing of multiple fluorochrome combinations (data not shown), it was determined that any fluorochrome pair having a similarity index of 0.98 or lower could be accurately unmixed with appropriate single stained controls. At the bottom of the matrix, the complexity index (blue arrow), a metric to evaluate the complexity of the entire combination of fluorochromes, is displayed. (C) Display of stain indices calculated for each of the fluorochromes in the panel, ranked from low to high. A more in-depth explanation of the Similarity Index is given below.

In block 6, a group of 30 or more fluorochromes are selected with similarity indexes less than a predetermined number (e.g., 0.98), from the commercially available fluorochromes. In one embodiment, 40 fluorochromes are selected, by discarding fluorochrome pairs with very high similarity indices.

The overall fluorochrome combination compatibility of the 40 selected fluorochromes was also quantified. This assessment was guided by a complexity index, also available in the SPECTROFLO software. The complexity index measures the interference among a specific combination of fluorochromes and predicts the degree of distortion to the spectrally unmixed results while considering spillover. The lower the complexity index, the higher the probability that the fluorochrome combination will work together and yield high resolution data through reduced spread. For the 40 fluorochromes shown in FIG. 7B the Complexity Index was 53.72. A more in-depth explanation of the Complexity Index is given below.

In some embodiments of the invention, an optional step, block 7 was performed. In block 7, a decision step is performed, rejecting the selected fluorochromes of block 6 if their overall complexity index is too high. Block 6 would then be repeated with another group of 30 or more fluorochromes selected.

After the 30 or more fluorochromes are selected by their Similarity and Complexity Index values, the 30 or more fluorochromes are ranked according to their brightness in block 8. The relative brightness of the fluorochromes can be used to effectively pair them with the cell markers that will give the highest resolution data.

In block 9, the 30 or more fluorochromes are paired with the 30 or more cell markers. Pair the 30 or more fluorochromes with the 30 or more cell markers. In general, the dimmest fluorochromes were assigned to antigens expressed at high levels and with high level of co-expression with other cell markers in the panel to minimize spread. Tertiary cell markers were assigned to bright fluorochromes to maximize resolution. For fluorochromes with the same primary excitation laser or similar emission wavelengths; avoid highly expressed antigens being placed in cells adjacent to co-expressed antigens with lower expression.

In block 10, the biological cells of interest are stained with the fluorochrome conjugated antibodies according to best practice staining protocols. The following adjustments were made in the staining process to increase resolution: (i) Adjusting titers increasing antibody concentration, (ii) Sequential staining was performed as needed, (iii) Addition of reagent to markers with poor resolution, and (iv) Centrifuging reagents with high antibody aggregate.

The stained biological cells of interest are collected in a multicolor sample tube and run through a full spectrum flow cytometer in block 11 of the method step.

In block 12, the raw data collected by the detectors of the flow cytometer are processed. Data analysis can include analyzing data including: manually gating to remove aggregates, dead cells, debris, and CD45 (lymphocyte common antigen) negative events, gating traditionally defined peripheral blood mononuclear cell (PBMC) populations, subsample the data to acquire the CD45+ live singlets, perform opt-SNE analysis, unmix data using software with an ordinary least squares algorithm, assembling clusters into commonly recognized biological populations and generating a heatmap of the resulting populations.

As for compensation, the unmixing accuracy is highly dependent on the quality of the reference controls and their ability to accurately represent the spectra of fluorochromes present in the MC staining. Using a full spectrum flow cytometer allows detection of even the smallest differences in fluorochrome emission. It is a well-known phenomenon that fluorochrome antibodies bound to beads vs. cells can produce slight differences in the spectra that are emitted.

In block 13, the raw data from 30 or more color flow cytometry panel is visualized as 2D dot plots, heat maps, or metacluster plots. The use of popular forms of data representation allows for quick verification of the efficacy of using the listed fluorochromes and cell markers in a single sample assay.

One of the great advantages of full spectrum flow cytometry is the ability to utilize highly overlapping fluorochromes that traditionally could not be used together in conventional flow cytometers. This capability was critical for the development of a 40-color panel. However, highly overlapping fluorochromes are known to exhibit increased spread into other fluorochromes, which could impact resolution quality. For highly overlapping fluorochromes where significant spread was anticipated, visual inspection of those combinations and impact of the spread were evaluated. In general, based on good panel design practices, these occurred in combinations of markers that are not co-expressed and therefore did not have a substantive negative impact.

Similarity and Complexity Indexes

When two fluorochromes are similar, they fluoresce with the same laser. The primary detectors for the fluorochromes will overlap being in the same detector module. The photons from the fluorescence of these two fluorochromes will spill over into the primary detectors of each other. This spillover effect leads to decreased sensitivity of those detectors for the measured fluorescence intensity, especially for negative signals. This will increase the spreading (standard deviation) of the negative populations events, making the positive populations and negative populations difficult to separate. A user's experience can subjectively guide them from selecting poor fluorochromes for a sample. However, it is desirable to introduce objective measurements to better inform the user of how fluorochromes interact with each other and assist in the selection of fluorochromes to use as assays for experiments with biological samples by a flow cytometer.

A similarity index and/or a complexity index are objective values that can be used to more rapidly select a plurality of fluorochromes or dyes that can be used with a flow cytometer to analyze biological cells within a biological sample fluid. The similarity index and/or the complexity index can be used to generate a flow cytometry panel (a set of fluorochromes conjugated with antibodies that adhere to cell markers) to show that a plurality of fluorochromes or dyes that can be discriminated in one sample run with a selected configuration (predetermined number of lasers and a predetermined number of detectors/detector modules) of a flow cytometer having.

Figure 8:
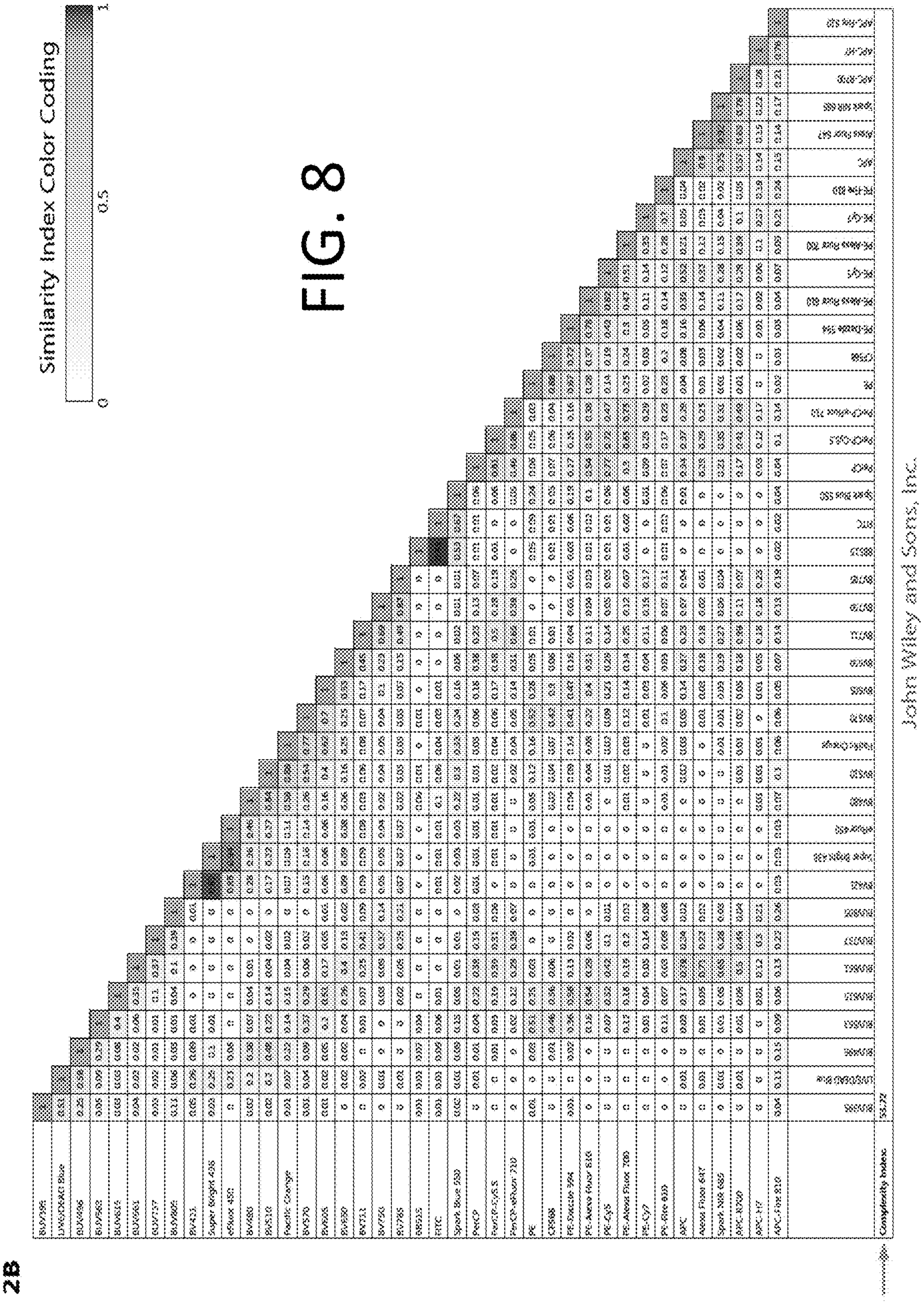
FIG. 8 illustrates a similarity matrix with similarity indexes and a computation of a complexity index for forty fluorochrome sample and a full spectrum flow cytometer having five lasers and five detector arrays such as shown in FIG. 2E.

FIG. 8 illustrates a similarity matrix for an exemplary group of forty (40) fluorochromes, sometimes simply referred to herein as colors. The similarity matrix includes a plurality of similarity indexes for pairs of each fluorochrome in the group being considered for labeling particles/cells. The similarity indexes are computed for a predetermined configuration (e.g., number of lasers, number of detector modules, number of detectors) of a flow cytometer. Because the similarity matrix is a mirror about its diagonal, only one side (upper or lower triangle of the matrix) needs to be completed. Because the diagonal is a fluorochrome paired with itself, the similarity index values for every entry along the diagonal of the matrix is the value of one (1). The value one for the similarity index indicates the fluorochrome pair along the diagonal is identical. Values of a similarity index less than one, cells off the diagonal, indicates the pairing of fluorochromes is not identical.

The cells in the similarity matrix can be color coded based on the value for similarity index being between zero and one. For example, the closer the similarity index value is to the value one, the darker color shade (e.g., dark blue) the cell in the matrix can be given. The closer the similarity index value is to the value zero, the lighter the shade of color the cell in the matrix can be given. At zero, the matrix cell is clear. The highest value of one for similarity index, can be color coded in the matrix cell with a different color (e.g., brown, red, or grey) along the diagonal. In this manner, high similarity index values and low similarity index values can be readily seen for choosing fluorochromes for a mixed sample. The respective pair of fluorochromes with high similarity index values can readily be avoided in a mixed sample or else understood in advance when used.

In FIG. 8, the value for complexity index for the set of fluorochromes is computed and displayed at the base of the similarity matrix. The complexity index is a condition number for the selected set of fluorochromes. With respect to flow cytometry, the complexity index is a measure of the multiple interferences from many fluorochromes to many fluorochromes. Stated differently, the complexity index is an overall measure of uniqueness of all dyes (fluorochromes) in a full spectrum flow cytometry panel. The lower the complexity value, the easier it will be to work with the dyes in the panel as the overall spread in the panel will be low. The higher the complexity value, the more challenging it will be to work with the selected dyes in the panel as the overall spread is high.

References are made to FIGS. 9-19 to illustrate how the similarity index for a pair of fluorochromes and the complexity index for a set of fluorochromes are formed and function. A number of matrices, such as the spillover matrix and others to unmix data from a mixed sample run through a full spectrum flow cytometer, are introduced in U.S. patent application Ser. No. 16/418,942; titled FAST RECOMPENSATION OF FLOW CYTOMETERY DATA FOR SPILLOVER READJUSTMENTS; filed on May 21, 2019 by Zhenyu Zhang; and incorporated herein by reference for all intents and purposes.

FIG. 9 is a simplified two-color assay (two fluorochromes) with a flow cytometer having three detectors representing only three dimensions. The two reference single colors Blue 1208 and Yellow 1209 when mixed together form a multi-sample color-green 1210. The objective is to understand how the two reference single colors interfere with each other when subsequently run together as the multi-color sample through the flow cytometer. To understand this, each reference color 1208 and 1209 is run separately through the flow cytometer and the spectral data is observed as it spills over all the detectors. Ordinarily, there is on the order of 32 detectors or multitudes thereof (e.g., 64) but such a large dimension is too difficult to simply illustrate.

FIG. 10 illustrates the generation of reference control vectors 1001A and 1001B for each reference single colors Blue and Yellow. Five thousand events may be observed in each case representing the detection of five thousand beads or cells marked with the single fluorochrome blue in a first reference sample or a single fluorochrome yellow in a second reference sample. A blue color event vector and a yellow color event vector can be plotted in the three dimensions of the three detectors.

In FIG. 11, a spillover matrix 1105 can be generated from the reference control vectors 1101A and 1101B. Spillover vectors 1105 are generated and grouped together into a spillover matrix 1105. The spillover matrix 1105 is used to unmix the yellow and blue colors when the multicolor sample green is run through the flow cytometer. The spillover matrix 1105 allows events related to the yellow color and events related to the blue color to be detected from the multicolor sample when it is run through the same flow cytometer. There is a spillover vector for every column associated with each fluorochrome (color). In our example we only have two columns 1106A and 1106B, one for each single reference color in the multicolor sample. If there were 40 fluorochromes in the multicolor sample, for example, there would be 40 columns in the spillover matrix. There is a row value in each spillover vector associated with every detector in the same flow cytometer. With 64 detectors, for example, there would be 64 rows in the spillover matrix. In FIG. 11, only 3 rows 1107A-1107C are illustrated. Spillover is how one fluorochrome with a peak color in a peak channel spills over into other detectors and thereby over into other fluorochrome colors when mixed together.

FIG. 12 illustrates a run of the multicolor sample and the generation of multicolor sample event vectors for each event representing the detection of a dye colored particle or cell. Sample 1 (green) 1210 can be unmixed by the spillover matrix to determine that it most likely represents the reference color blue. While only two fluorochromes representing two-dimensional matrix are utilized, additional dimensions can be analyzed with more lasers and more detectors. For example, up to 38 different dimensions (with 38 detectors) can be analyzed with three color excitation lasers of one flow cytometer. In another example, up to 64 different dimensions (with 64 detectors) can be analyzed with a five-color excitation laser in a different configuration of the flow cytometer.

FIG. 13, top illustration, shows a full spectral signature for a 64 channel/detector flow cytometer system. FIG. 13, bottom illustration, shows a 64-dimensional vector associated with 64 detectors that mathematically represents the spectra signature shown in the top illustration. Given two spectral signature of reference samples, the spectral signature of one dye color (one fluorochrome) can be mathematically compared with the spectral signature of another dye color (one fluorochrome) to see how they overlap and interfere in advance, before they are mixed together and run through a flow cytometer. The similarity index is used to compare the reference control vectors of pairs of fluorochromes.

In FIG. 14, left side, an example of two reference control vectors 1201A and 1201B are plotted in two dimensions to show how a similarity index can be formed. There is a difference between the horizontal vector (vector 1-color 1) 1201B and the diagonal vector (vector 2-color 2) 1201A. That difference can be computed to show how different or how similar the refence control vectors are to each other. There are different ways to compute the difference described herein. One way is to compute the cosine of the angle theta between the two reference control vectors 1201A and 1201B. In the example illustrated on the left side, there is an angle of 25.8 degrees. Taking the cosine of this angle provides a similarity index value of 0.9. By experimentation, any larger value is not very desirable because the two dyes are too similar. In the right side of the figure, the angle between the reference control vectors 1201C and 1201D is ninety degrees. The vectors 1201C-1201D are orthogonal indicating there is no overlap. The cosine of 90 degrees is zero so the similarity index of zero represents no overlap or interference between the two selected colors. This is rather simple in two dimensions with only three detector and only two reference colors. We now have to introduce matrices to deal with the larger dimensions that are desired.

Assume a reference matrix [R] is a N by M reference matrix obtained from single stained reference controls, where N is the number of detectors, M is the number of fluorochromes to be measured with the number of fluorochromes M always being less than or equal to the number of detectors N.

Further assume that the vector $\{V_m\}$ is a measured sample event vector with N values, with each value being from a different one of the number of detectors N of the flow cytometer.

Further assume that the vector $\{V_d\}$ is the de-convoluted sample event vector with M values, with each value being a de-convoluted value for a different fluorochrome of the number of fluorochromes M used in a sample.

The de-convoluted sample event vector $\{V_d\}$ can be obtained as follows:

$$\{V_d\} = \left[R^T R\right]^{-1}[R]^T\{V_m\} \text{ or } \{V_d\} = \frac{[R]^T}{\left[R^T R\right]}\{V_m\}$$

The de-convoluted sample event vector $\{V_d\}$ is equal to a transpose of the reference matrix divided by the product of the transpose of the reference matrix and the reference matrix itself multiplied against the measured sample event vector $\{V_m\}$.

The reference matrix [R] is determined by the following equation $$R = \begin{bmatrix} SOV_{1,f1} & SOV_{1,f2} & \cdots & SOV_{1,fM} \\ SOV_{2,f1} & SOV_{2,f2} & \cdots & SOV_{2,fM} \\ \vdots & \vdots & \vdots & \vdots \\ SOV_{N,f1} & SOV_{N,f2} & \cdots & SOV_{N,fM} \end{bmatrix}$$

The $SOV_{N,fM}$ values are the spillover values for each of the N detectors and each of the M fluorochromes (fM). Each fluorochrome (f1 through fM) can be run separately in a reference sample (conjugated to an antibody that is attached to a cell or a bead) through a given flow cytometer to determine the values in each column of the reference matrix [R] for each detector (1 through N) of the predetermined number of N detectors of the given flow cytometer.

Similarity Index

In the case of the similarity index, two fluorochromes (dyes) are compared to evaluate how they interfere each other when used together in the same biological sample with markers to form a flow cytometry panel. Two reference control vectors R1 for fluorochrome 1 (f1) and R2 for fluorochrome 2 (f2) are used for example to perform a comparison.

Reference control vector $$R1 = \begin{bmatrix} SOV_{1,f1} \\ SOV_{2,f1} \\ \vdots \\ SOV_{N,f1} \end{bmatrix}$$

and reference control vector $$R2 = \begin{bmatrix} SOV_{1,f2} \\ SOV_{2,f2} \\ \vdots \\ SOV_{N,f2} \end{bmatrix}.$$

If each of the reference control vectors are plotted along lines from a center point, they would show how they diverge from each other. A difference between the two reference control vectors, such as a distance, can be used to provide a measure of interference between the two fluorochromes. There are different type of distances for above measuring purpose, such as $L^p$ (Lebesgue spaces) p-norm distances of Euclidean √{(x_i−y_i)^2)}, Minkowski √[p]{(x_i−y_i)^p)}, and Manhattan Σ{|x_i−y_i|}; and Cosine (from angle in between the reference control vectors). Among these distances, the Cosine of the angle between reference control vectors was more meaningful because it describes two independent controls (orthogonal reference control vectors–90-degree angle between each) when the cosine value is zero. That is, the angle between the two reference control vectors can be used as a parameter to evaluate how two dyes interfere each other in the output data of a flow cytometer when used together in the same biological sample.

Generally, the angle itself between the two reference control vectors R1 and R2 can be used to provide a measure of similarity or difference for the interference between two fluorochromes. In another case, a mathematical function (e.g., cosine function or the $L^p$ p-norm distances) can be used to normalize and/or generate a measure of similarity or difference for the interference between two fluorochromes.

In accordance with one embodiment, a cosine function on the angle between the two reference control vectors is used to generate the similarity index. That is, the similarity index can be the cosine value of the angle between two spillover columns (two reference control vectors) in the reference spillover matrix R. If the similarity index is zero (cosine of 90 degrees), there is no interference between the two fluorochromes. If the similarity index is one (cosine of 0 degrees), there is complete overlap interference between the two fluorochromes because they are likely the same fluorochrome.

The similarity index is a measure of dye pair uniqueness on a scale from 0 to 1. Values close to 0 indicate that the full spectrum signature of the 2 dyes are very different from each other. Values close to 1 for similarity index indicate that the spectrum signatures are very similar to each other.

Complexity Index

In the field of numerical analysis, the condition number of a function measures how much the output value of the function can change for a small change in the input argument. The condition number is used to measure how sensitive a function is to changes or errors in the input, and how much error in the output results from an error in the input. A low condition number is said to be well-conditioned, while a high condition number is said to be ill-conditioned.

The condition number is an application of the derivative, and may be defined as the value of the asymptotic worst-case relative change in output for a relative change in input. The condition number is frequently applied to questions in linear algebra, in which case the derivative is straightforward but the error could be in many different directions. The condition number can be computed from the geometry of the matrix.

In the case of multiple fluorochromes (Fluor1 through Fluor M), the complexity index is a condition number of the reference spillover matrix R. While the similarity index is a measure of the one to one interference between two fluorochromes; the complexity index is a measure of the multiple interferences from many fluorochromes to many fluorochromes.

FIG. 15 illustrates a mathematical approach to explain the complexity index. Based on linear algebra and Singular Value Decomposition, any matrix (M) can be decomposed into three matrix transformations: a rotation, a scaling, and another rotation as shown. The matrix M can be represented by three matrices by the following equation: $M=U\cdot\Sigma\cdot V^*$.

FIG. 16 illustrates the mathematical approach to generating the complexity index. There are different linear algebra theorems that allows decomposition a matrix into several matrix transformations. A single spillover matrix can be represented my three matrixes that when multiplied together generate the original spillover matrix. To generate a complexity index, the similarity matrix is decomposed by using the Singular Value Decomposition theorem in linear algebra. One of the resulting matrixes from that decomposition is a diagonal matrix whose values behave like a scaling factor. The diagonal matrix can be referred to as a diagonal scaling matrix. The magnitude of the diagonal values in the diagonal scaling matrix is directly related to how similar or dissimilar two dyes are to each other. As shown in FIG. 16, one way of computing a complexity index is to choose the maximum value in the diagonal and divide it by the minimum value in the diagonal. Accordingly, one would expect that a larger value for the complexity index is less desirable than a smaller value for the complexity index for a given set of selected fluorochromes that are to be mixed together in a mixed sample.

The complexity index is an overall measure of uniqueness of all dyes in a full spectrum cytometry panel. The lower the value, the easier it will be to work with the dyes in the panel as the overall spread in the panel will be low. The higher the value, the more challenging it will be to work with the dyes in the panel as the overall spread is higher. Well design panels with few dyes (e.g., 10 or less) can have complexity index on the order of values of 2 or 3, for example. Well design larger panels (e.g., 35 to 40 colors or more) will have complexity indexes of around 40 to 50 or less.

FIG. 17 illustrate simple examples of complexity matrices and complexity indexes for pairs of fluorochromes. Example matrices for three different combinations of two dyes. The presence of only one or two large similarity indexes greatly increases the complexity index. The scaling or stretching between two close dyes, shows itself in the data in slanted negative complexity index bar.

FIG. 18 illustrates a large complexity matrix for analyzing simplicity indexes together and generation of the complexity value. This shows the similarity indices and complexity index for a full 35 color panel including the viability dye. Examples to the right state the complexity index. Identified 35 dyes that are all unique, and have a mixture of brightness levels. In the exemplary similarity and complexity indices of FIG. 18, a threshold similarity index of 0.88 was determined. An initial complexity index of 46.53 was determined for this selection of fluorochromes. Six pairs of fluorochromes were found to have a similarity index greater than 0.88. One fluorochrome from the six pairs of fluorochrome were removed from consideration for the panel. In this example, CF568, AF647, PerCP-eF710, SB436, & BB515 were removed (SB436 were in two pairs of fluorochrome with a similarity index greater than 0.88, thus only 5 fluorochromes were removed from consideration. After the removal of the five sub-optimal fluorochromes, the complexity index was calculated again and found to have reduced to 35.33.

The condition number of the reference spillover matrix R is equal to the square root of the condition number of the complexity matrix $[R^T R]$.

For a panel of M fluorochromes (Fluor1, Fluor2, . . . . FluorM), the complexity matrix can be determined from the following equation $$[R^T R] = \begin{bmatrix} V_{1,1} & V_{1,2} & \cdots & V_{1,M} \\ V_{2,1} & V_{2,2} & \cdots & V_{2,M} \\ \vdots & \vdots & \vdots & \vdots \\ V_{M,1} & V_{M,2} & \cdots & V_{M,M} \end{bmatrix}.$$

The complexity matrix summarizes the mutual similarity of the reference controls provided by the set of fluorochromes used in one flow cytometer run with one biological sample. The Vx,y entries in the complexity matrix are the inner products of the reference controls for two fluorochromes. Thus, the Vx,y entries in the complexity matrix relate to the similarity indices derived from the comparison of two spillover (SOV) vectors of the modeled fluorochromes.

The complexity matrix is derived from the equation $[R^T R]$ and the Vx,y values are the elements in the resultant $[R^T R]$ matrix, where x and y vary from 1 to M, M being the number of fluorochromes for a given sample/flow cytometry panel. Accordingly, each row in the complexity matrix indicates a different fluorochrome. That is the first row is fluorochrome 1, the second row is fluorochrome 2, and so on and so forth, and the Mth row is fluorochrome M. A row index value (e.g., Fluor1, Fluor2, . . . , FluorM) for each row of the matrix may be used to indicate the selected fluorochrome for a sample. Similarly, each column in the complexity matrix indicates a different fluorochrome.

Note that the complexity matrix is symmetrical, an M by M matrix, where M is the number of fluorochromes. The entries from V1,1 to VM,M along the diagonal of the complexity matrix are expected to be the value of 1 since the same fluorochrome is being compared with itself.

We can take the condition number of the complexity matrix $[R^T R]$ representing sensitivity of the matrix to perturbations in value. Then the square root of the condition number of the complexity matrix $[R^T R]$ is equal to the condition number of the reference spillover matrix R, that is simply referred to as the complexity index.

Co-Expression to Simplify Complexity Index Determination

If two fluorochromes co-express on the same stained particle (they interfere with each other), the calculated value of similarity index will provide a measurement of the spillover impact (light emitted/fluorescing at similar wavelengths) between the two fluorochromes. The bigger the similarity index value (closer to one), a more reduced resolution between each is to be expected due to the spillover of these two fluorochromes. The smaller the similarity index value (closer to zero), the greater the resolution (less spillover and spectral overlap) between each of the two fluorochromes For the panel of M fluorochromes (Fluor1, Fluor2, . . . . FluorM), the co-expression of the fluorochromes can be expressed by a symmetrical co-expression matrix as follows:

$$\begin{bmatrix} CE_{1,1} & CE_{1,2} & \cdots & CE_{1,M} \\ CE_{2,1} & CE_{2,2} & \cdots & CE_{2,M} \\ \vdots & \vdots & \vdots & \vdots \\ CE_{M,1} & CE_{M,2} & \cdots & CE_{M,M} \end{bmatrix}.$$

Each row in the symmetrical co-expression matrix indicates a different fluorochrome. That is the first row is fluorochrome 1, the second row is fluorochrome 2, and so on and so forth, and the Mth row is fluorochrome M. A row index value (e.g., Fluor1, Fluor2, . . . , FluorM) for each row of the matrix may be used to indicate the selected fluorochrome for a sample. The row index value may be used herein to refer to the entire row of values.

If Fluor1 and Fluor2 co-express, then $CE_{2,1}$ and $CE_{1,2}$ are both equal to 1. Otherwise, if Fluor1 and Fluor2 do not co-express, $CE_{2,1}$ and $CE_{1,2}$ are both equal to 0. Therefore, each of the elements in the co-expression matrix is either 1 or 0.

To take out the effects of all the non-co-expressed fluorochromes of the panel, the complexity matrix can be modified by the co-expression matrix using matrix multiplication. The matrix multiplication (or product) of the complexity matrix and the co-expression matrix results in a modified complexity matrix as follows:

$$\begin{bmatrix} CE_{1,1}V_{1,1} & CE_{1,2}V_{1,2} & \cdots & CE_{1,M}V_{1,M} \\ CE_{2,1}V_{2,1} & CE_{2,2}V_{2,2} & \cdots & CE_{2,M}V_{2,M} \\ \vdots & \vdots & \vdots & \vdots \\ CE_{M,1}V_{M,1} & CE_{M,2}V_{M,2} & \cdots & CE_{M,M}V_{M,M} \end{bmatrix}$$

Each row in the modified co-expression matrix indicates a different fluorochrome. That is the first row is fluorochrome 1, the second row is fluorochrome 2, and so on and so forth, and the Mth row is fluorochrome M. A row index value (e.g., Fluor1, Fluor2, . . . , FluorM) for each row of the matrix may be used to indicate the selected fluorochrome for a sample. The row index value may be used herein to refer to the entire row of values. Similarly, each column in the modified co-expression matrix indicates the different fluorochromes (controls) used in the same sample assay.

Determining the condition number of this modified complexity matrix is a more accurate measurement to use as the complexity index.

Similarly, the co-expression matrix can also be applied to a cross stain index reduction matrix. With a cross stain index reduction matrix modified by the co-expression matrix, a more accurate measurement of cross stain index reduction can be obtained.

There is one more thing we need to consider before assigning cell markers to each fluorochrome. The spread of data clusters needs to be considered.

FIG. 19 illustrates the classifications for various antigens. The primary antigens 1921 have a high density on or off expression. The left graph histogram 1925 has very clear bimodal peaks so that positive and negative can be seen the distance between peaks is wide across the spectrum.

The secondary antigens 1921 have an intermediate density with a continuous expression. In the middle graph 1926, there is a continuum between a left peak and a right peak. Some consideration is made to see clearly in the middle between the peaks. A fluorochrome needs to brighter to see over the middle spectrum.

The tertiary antigens 1922 have a low density with an unknown expression. The right graph histogram 1927 does not have a clear separation between the peak and the shoulder peak. Very bright colors need to be used.

The spreading or broadening of peaks can also be an issue when mixing colors together. The data clusters can spread and make it more difficult to detect positive or negatives. A cross stain index values in a cross-stain matrix should also be considered when mixing with other colors.

Accordingly, in panel design, it is desirable to consider the level of antigen expression when selecting fluorochromes to use in a mixed color sample represented by a color flow cytometry panel.

User Interface for Selecting Fluorochromes.

The design of a flow cytometer can bring flexibility in selecting fluorochromes for labeling biological cells and particles. Full spectrum cytometry has the advantage of detecting the full spectrum signature for each fluorochrome with a full spectrum flow cytometer with at least five lasers and at least 64 detectors. Almost any commercially available fluorochrome can be excited by the lasers of a full spectrum flow cytometer.

With so many options, it is useful to provide a web-based user interface displayable on a monitor or display device to more quickly and more easily choose fluorochromes for use in experiments on biological samples with a full spectrum flow cytometer. A computer or other electronic device, including a processor and input/output devices, is coupled to the internet and the monitor or display device in order to generate and display the web-based user interface. The web-based user interface is generated by a spectrum viewer web-based software tool. The software tool can be executed on a client computer device locally with access to a remote database or remotely on a server computer in communication with the remote database.

Reference is now made to FIGS. 20A-27C. With the spectrum viewer web-based software tool, users can choose from commercially available fluorochromes that have been previously tested on different configurations of a flow cytometer. For example, FIGS. 22A-22B illustrate an expanding list of fluorochromes tested on a full spectrum cytometer with possible different configuration options.

The spectrum viewer web-based software tool helps users figure out which fluorochromes could be used together on the various configurations of the full spectrum flow cytometer. The software tool can display full spectrum information for over 80 fluorochromes acquired using an assay setting across all of the configurations for the full spectrum flow cytometer.

The spectrum viewer web-based software tool can use the similarity index and the complexity index to further assist a user in selecting fluorochromes than can be used together with the full spectrum flow cytometer in its various configurations.

FIG. 20A a block diagram of a computing system 800 is shown that can execute the software instructions to execute a web browser to graphically display a graphical user interface (GUI) 855 to assist a user in selecting fluorochromes that can be used together with the full spectrum flow cytometer in its various configurations. FIG. 20B is a block diagram illustrating the computing system 800 coupled to a remote computer server 889 over the cloud or internet 888. Monitor 802 illustrates the GUI 855 generated by the server 889 and displayed by the computing system 800. The server 889 is in communication with a database 890 that stores information about the available fluorochromes for use with various configurations of a flow cytometer. The information is determined by running each fluorochrome as a reference sample alone through the flow cytometer. The spillover over vector for each fluorochrome is added into a spillover matrix stored in the database 890. A user can then access the database and select one or more fluorochromes with their underlying data and have graphs charted and the similarity indexes and the complexity index determined.

In one embodiment, the computing system 800 includes a computer 801 coupled in communication with a graphics monitor 802, and one or more input devices, such as a mouse pointer 803 and a keyboard text entry device 804. The computer 801 can couple to other external devices through a plurality of network interfaces 861A-861N, a plurality of radio transmitter/receivers (transceivers) 862A-862N; and a parallel serial I/O interface 860.

In accordance with one embodiment, the computer 801 can include one or more processors 810, memory 820; one or more storage drives (e.g., solid state drive, hard disk drive) 830,840; a video input/output interface 850A; a parallel/serial input/output data interface 860; a plurality of network interfaces 861A-861N; a plurality of radio transmitter/receivers (transceivers) 862A-862N. The graphics monitor 802 can be coupled in communication with the video input/output interface 850.

The data interface 860 can provide wired data connections, such as one or more universal serial bus (USB) interfaces and/or one or more serial input/output interfaces (e.g., RS232). The data interface 860 can also provide a parallel data interface. The plurality of radio transmitter/receivers (transceivers) 862A-862N provide wireless data connections such as over WIFI, Bluetooth, and/or cellular. The one or more audio video devices can use the wireless data connections or the wired data connections to communicate with the computer 801.

The computer 801 and computing system 800 can interface with an external server computer 889 in the cloud over the internet 888 through one or more of the plurality of network interfaces 861A-861N and/or the plurality of radio transmitter/receivers (transceivers) 862A-862N. Each of these network interfaces can support one or more network connections.

One or more computing systems 800 and/or one or more computers 801 (or computer servers) can be used to perform some or all of the processes disclosed herein. The software instructions that perform some of the functionality described herein, are stored in the storage device 830,840 and loaded into memory 820 when being executed by the processor 810.

In one embodiment, the processor 810 executes instructions residing on a machine-readable medium, such as the hard disk drive 830,840, a removable medium (e.g., a compact disk 899, a magnetic tape, etc.), or a combination of both. The instructions may be loaded from the machine-readable medium into the memory 820, which may include Random Access Memory (RAM), dynamic RAM (DRAM), etc. The processor 810 may retrieve the instructions from the memory 820 and execute the instructions to perform operations described herein.

FIG. 21 illustrates the basic GUI 855 of the spectrum viewer software application that can be displayed on the monitor 802 by the computer system 800. The GUI 855 includes a graph 856 that plots a normalized excitation/emission 857 along a Y axis and an emission channel 858 along the X axis. The normalized excitation/emission 857 ranges from zero to 100 percent. The emission channels related to the expected wavelengths of light that the fluorochromes fluoresce. From left to right, the emission channels 857 can include ultra violet channels UV1-UV16; violet channels V1-V16; blue channels B1-B14; yellow-green channels YG1-YG10; and red channels R1-R8. With fewer lasers and fewer detectors, the channels can decrease. With more lasers and more detectors, the number of channels can increase.

There are a number of buttons that the GUI provides. The GUI can selectively display a grid on the graph 856 by the use of a grid show button 859. After selecting a set of fluorochromes for a color panel and a sample run with a biological sample, the GUI can export the graph and the choice of fluorochromes (e.g., see FIG. 27C) through the export spectra button 860. After selecting a set of fluorochromes for a color panel and a sample run with a biological sample, a similarity/complexity button 861 can also be selected in the GUI 855. This button displays a picture in picture window, that can also be printed out, with computed similarity indexes and the computed complexity index (e.g., see FIGS. 23A,27B) for the given set of fluorochromes.

The GUI 855 displays a flow cytometer configuration 862 that is selected by a pull-down menu 872 for the given flow cytometer. This designates the number of excitation lasers and the number of detectors that the flow cytometer is configured with. This can be selected before or after the fluorochromes are selected. However, if one drops down to a lesser configuration, some fluorochromes may not be used and drop out, such as if a laser is dropped.

The GUI 855 displays fluorochromes 863 that are available for selection previously tested with the flow cytometer configuration. The fluorochromes may be browsed by way of a slider 876 and displayed in a fluorochrome viewer window 875 The fluorochromes may be searched by name using the search by name field 873 or searched by peak channel using the search by peak channel input field 874. The fluorochromes can be selected by double clicking through an input device (e.g., mouse clicks) the desired fluorochrome name in the window 875. Once selected, a spectra graph 902 is drawn in the chart window 856.

The GUI 855 displays the fluorochromes/tags 864 that are selected. The names of the fluorochromes selected are added into a selection window 877. A count window 878 indicates the current selected number of selected fluorochromes in the selection window 877 for the panel and sample for a flow cytometer run. A user can select a selected fluorochromes in the selection window 877 and delete it from the set. Alternatively, if a user wants to start completely over, a clear all button 879 is provided by the GUI 855.

FIGS. 22A-22B illustrate some of the fluorochromes that can be selected by the GUI. As more fluorochromes are tested with the various configurations of the flow cytometer, their spillover over matrices are generated and added into the database 890 accessible by computer over the internet 888 through the GUI 855 and the computer server 889.

FIG. 23A illustrates an exemplary set of 7 fluorochromes selected in the GUI 855 and displayed by the monitor 802. As each fluorochrome is selected, its graph is displayed in the graph window. Seven spectra graphs 902A-902G are displayed in the graph window 856, one for each of the seven selected fluorochromes. A grid 900 is also shown in the graph window 856 between the axes 857,858 for perspective. The axis 858 shows a shorter emission channel due to the configuration of the modular flow cytometer. As indicated by the configuration window 862, the modular flow cytometer has 3 excitation lasers and 16 violet, 14 blue, and 8 red detector channels; less than the full spectrum of 5 or more lasers and additional detector channels. It would be expected ultra violet fluorochromes would be of little use in this configuration. The spectra graphs 902A-902G visually shows how fluorochromes can interact with each other given overlap or closeness of peaks. Selection of the similarity/complexity button 861 generates a graph of similarity indexes and computers the complexity index.

FIG. 23B illustrates a similarity/complexity chart 904 of similarity indexes opened in a new GUI window 905. This is in response to selection of the similarity/complexity button. A complexity index value 906 is also displayed adjacent the chart 904. Along and adjacent both the X and Y axis of the chart are the selected fluorochromes. The chart indicates the values for a plurality of similarity indexes 907 for each X, Y pair of fluorochromes. Note that the similarity index value is 1 when the same fluorochrome is matched up against itself (e.g., R718,R718). A similarity index value of 0 (such as AlexaFluor546,Qdot 800 fluorochrome pair) indicates little to no interference between two fluorochromes when used together in the same assay for a sample. Shading can be added to the squares in order to emphasize the similarity index values that have the higher and highest the similarities. No shading indicates a low similarity index value. In this example the complexity index value is 2.73.

FIG. 24A illustrates a plurality of configurations 872 for the modular flow cytometer that are selectable by the pull-down menu 872. A checkmark 910 illustrates the configuration presented selected by an input device such as a mouse. The configuration can be changed on the fly, if desired. FIGS. 23A-23B were generated using 3L configuration. Updated graphs and similarity indexes and complexity index can be made with the 5L configuration.

Referring now to FIG. 24B the flow cytometer configuration was improved to a five laser configuration. The graphs 902A-902G of the same fluorochromes are now spread out over the full number of emission channels. The similarity/complexity button 861 can be selected to generate a similar similarity index chart with updated values for similarity indexes and the complexity index of the group of fluorochromes.

Referring now to FIG. 24C, an updated similarity/complexity chart 904' is shown with the improved configuration in the modular flow cytometer. This is in response to selection of the similarity/complexity button. Generally, there are fewer shaded squares for the similarity indexes, indicating an improvement between fluorochromes selected. The complexity index number has slightly changed to 2.81, remaining at a low and acceptable level of complexity index.

FIG. 25 illustrates searching for fluorochromes by name, such as channel UV, with the input field 873. FIG. 26 illustrates searching for fluorochromes by peak channel, such as channel UV6, with the input field 874. FIG. 26 illustrates searching for fluorochromes by name, such as channel UV, with the input field 873. Comparing FIGS. 25 and 26, the search results for searching by name and by peak channel can differ. Regardless, the search fields can help assist a user in the selection of a fluorochrome.

FIGS. 27A-27B illustrates a GUI windows with a selection of a large number of fluorochromes (e.g., 46 randomly) with a full spectrum configuration for the flow cytometer, such as 5 lasers (5L) and 64 detection channels (16UV-16V-14B-10YG-8R). Other configurations may be added to support the full spectra as improvements are made to the flow cytometer.

FIG. 27A illustrates a GUI window with forty-six graphs 902 for the random selection of forty-six fluorochromes in the graph window 856 over the emission channels after their selection. The graph is very busy such that it is difficult for a user to subjectively know how this selected set of fluorochromes will do when used for analysis. Objective measures would be very helpful to gain an understanding how the set of fluorochromes would perform without even running all of the fluorochromes in a test sample through the flow cytometer. The similarity indexes and the complexity index can provide that objective measure for fitness. Upon selection of the similarity/complexity button 861, a new similarity/complexity chart can be generated.

FIG. 27B illustrates a similarity/complexity chart 904 of similarity indexes opened in a new GUI window 905. This is in response to selection of the similarity/complexity button. Only the lower half of the matrix chart needs to be complete because it is a mirror image along the diagonal axis of 1 similarity index values. The shading indicates higher similarity indexes indicating those pairs might pose an issue. The greater the shading the higher the similarity index and the greater potential for interference. The highest shading is reserved for the highest similarity indexes below 1. The similarity index value of 1 is highlighted with a different color (e.g., grey) instead of the blue shading reserved for values below 1. We should expect the complexity index of the 46 fluorochromes to be greater than that of the 7 previously selected. Indeed, the complexity index value of these 46 randomly selected fluorochromes is about 869.32 and likely to be unacceptable. Regardless, this illustrates how easy the GUI 855 allows a user with no training to randomly select fluorochromes and determine an objective measure of overall mutual interference with a selected set of fluorochromes, before the user runs any tests.

FIG. 27C illustrates a GUI window shown in response to selection of the export spectra button 860. After selecting a set of fluorochromes (e.g., see FIG. 24B) for a color panel and a sample run with a biological sample, the GUI can export the graph and the choice of fluorochromes through the export spectra button 860. An export GUI window 855C is displayed and available to print out in hard copy or in soft copy formats. FIG. 27C is an export for the 46 randomly selected fluorochromes discussed with reference to FIGS. 27A and 27B. The graphs 902 are similar to that shown in the graph window 856 shown in FIG. 27A. A full listing 922 of the selected fluorochromes is displayed under the graphs in the graph window 856. The flow cytometer configuration is somewhat obvious by the emission channels that are displayed. However, the flow cytometer configuration can also be displayed and printed out by the GUI window 855C.

Configurable Flow Cytometer.

Referring now to FIGS. 28 and 29, a portion of the optical analysis system of modular flow cytometers are shown. The top view of an optical plate assembly 2800,2900 in a modular configurable flow cytometry system is shown. A modular configurable flow cytometer system is configurable in that different combinations of numbers of lasers (e.g., 1, 2, 3, 4, 5) and numbers of detectors (e.g., 14, 16, 22, 30, 32, 38, 48, 54, 64, 128, 256) can be chosen and installed in the flow cytometer. A flow cytometer can be configured with a combination of one, two three, four, five (5) or more lasers and fourteen, sixteen, twenty-two, thirty, thirty-eight, forty-eight, fifty-four, sixty-four (64) or more detectors. With four or more lasers and forty-eight or more detectors, a flow cytometer can act as a full spectrum flow cytometer capturing more electromagnetic spectra than that of a three laser and a thirty-eight detector configuration.

FIG. 28 shows a top view of an optical plate assembly 2800 for a modular flow cytometry system 100. The optical plate assembly 2800 includes a laser system 2870 having three semiconductor lasers 2870A,2870B,2870C that direct excitation into a flow cell assembly 2808 where a sample fluid flows with sample particles. The laser system 2870 attempts to direct the multiple (e.g., three to five) laser beams in a parallel manner toward the flow cell assembly 2808. The multiple laser beams are slightly offset from one another. The laser system 2870 includes semiconductor lasers 2870A,2870B,2870C. The semiconductor laser generate laser beams having different wavelengths, such as 405 nanometers (nm), 488 nm, and 640 nm for example. The output power of the semiconductor lasers can differ as well. For example, a 405 nm semiconductor laser can generate a laser beam that with an output power that is usually larger than 30 milliwatts (mW). The output power of a 488 nm semiconductor laser is usually greater than 20 mW. The output power of a 640 nm semiconductor laser is usually greater than 20 mW. Controller electronics in the flow cytometer control the semiconductor lasers to operate at a near constant temperature and a near constant output power.

An optical system spatially manipulates the optical laser beams 2871A,2871B,2871C generated by the semiconductor lasers 2870A,2870B,2870C respectively. The optical system includes lenses, prisms, and steering mirrors to focus the optical laser beams onto a fluidic stream carrying biological cells (bio cells). The focused optical laser beam size is typically focused for 50-80 microns (μm) across the flow stream and typically focused for 5-20 μm along the stream flow in the flow cell assembly 2808.

In FIG. 28, the optical system includes beam shapers 2830A-2830C that receive the laser light 2871A,2871B, 2871C from the semiconductor lasers 2870A-2870C, respectively. The laser light output from the beam shapers 2830A-2830C are coupled into mirrors 2832A-2832C respectively to direct the laser light 2899A,2899B,2899C towards and into the flow cell assembly 2808 to target particles (e.g. biological cells) stained with a dye of fluorochromes. The laser light 2899A,2899B,2899C is slightly separated from each other but directly substantially in parallel by the mirrors 2832A-2832C into the flow cell assembly 2808.

The laser light beams 2899A,2899B,2899C strike the particles/cells as they pass by in the flow stream in the flow cell assembly 2808. The laser light beams 2899A,2899B, 2899C are then scattered by the particles/cells in the flow stream causing the fluorochromes to fluoresce and generate fluorescent light, and the particles/cells to autofluoresce. A forward scatter diode 2814 gathers on-axis scattered light. A collection lens 2813 gathers the off-axis scattered light and the fluorescent light and directs them together to a dichromatic mirror 2810. The dichromatic mirror 2810 focuses the off-axis scattering light onto a side scatter diode 2815. The dichromatic mirror 2810 focuses the fluorescent light onto at least one fiber head 2816. At least one fiber assembly 2802 routes the fluorescent light toward at least one detector module 2801.

For a more detailed analysis of a biological sample using different fluorescent dyes and lasers wavelengths, multiple fiber heads 2816,2916, multiple fiber assemblies 2802,2902 and multiple detector modules 2801,2901 can be used. For example, three or more fiber heads can be used (e.g., see FIG. 28 with three, and FIG. 29 with five) with three or more detector modules associated with three or more lasers.

FIG. 28 shows three fiber heads 2816A,2816B,2816C situated in parallel to receive the fluorescent light and three fiber assemblies 2802A,2802B,2802C can be used to direct the fluorescent light to three detector modules 2801A, 2801B,2801C (only one of which is shown in FIG. 28). The first detector module 2801A is located on the optical plate 2800 while the other detector modules are located on a different level. The three fiber heads 2816A,2816B,2816C (and three fiber assemblies 2802A,2802B,2802C) for the three different detector modules paired with the three laser light beams 2899A,2899B,2899C which are slightly offset from each other (e.g., not precisely co-linear). Accordingly, three fiber heads 2816A,2816B,2816C can collect light beam data separately fluorescent light generated by the three laser light beams 2899A,2899B,2899C, having three different wavelengths to excite fluorochromes. The three fiber assemblies 2802A,2802B,2802C then direct light into three different detector modules (e.g., three different detector modules 2801A, 2801B, 2801C), one of which is located on the optical plate 2800 with others located below the optical plate on a lower level of the flow cytometer.

FIG. 29 shows an optical plate 2900 for a full spectrum flow cytometer having a configuration of five lasers and five detector modules with sixty-four photodetectors. The optical plate 2900 has some similar elements to the optical plate 2800. The optical plate 2900 has five fiber heads 2916 for five detector modules (detector modules located off the optical plate). The optical plate 2900 has five lasers 2970A-2970E, one of which is a violet laser 2970D and another one of which is a UV laser 2970E, for exciting and detecting light over the full visible spectrum, including a portion of the UV wavelength spectrum. The laser light beams 2999A, 2999B,2999C,2999D are generated in parallel by the lasers 2970A,29070B,29070C,2970D. The UV laser light beam 2999E is generated by the UV laser 2970E spaced apart and initially perpendicular to the laser beams 2999A,2999B, 2999C,2999D. The UV laser light beam 2999E is reflected by a first mirror 2998 on the optical plate and directed to run in parallel to the laser beams 2999A-2999D generated by the respective lasers. The mirrors 2932A,2932B,2932C,2932D, 2932E respectively receive the laser beams 2999A-2999E along their parallel but different paths, and reflect the laser beams to the flow cell assembly 2908 spaced apart in parallel along the same path.

The optical plate 2900 includes a forward scatter detector 2914 that gathers on-axis scattered light from the particles/cells. A collection lens 2913 coupled to the flow cell assembly 2908 gathers the off-axis scattered light, the fluorescent light, the autofluorescent light and directs them together to the fiber heads 2916.

The violet and UV lasers and violet and UV detectors differ from the lasers and detectors of the flow cytometer with the optical plate 2800. The violet and UV detector modules have more photodetectors and therefore detect a wider range of wavelengths of fluorescence light when violet and UV lasers strike a particle/cell. With the UV laser 2970E on the optical plate 2900, the detector modules 2901A,2901B,2901C,2901D,2901E (collectively referred to as detector modules 2901) are moved off the optical plate 2900. With a plurality of fiber assemblies 2902 and fiber heads 2916, the light from the flow cell 2908 can be directed into the plurality of different detector modules 2901 in different locations of the flow cytometer.

Not only can the excitation be modular (and configurable) in a modular flow cytometry system, but the detection can also be modular. The modular flow cytometry system can also use one or more detector modules 2801,2901 to collect the light beam data. For example, one or more fiber assemblies can direct light from a flow cell into one or more differing detector modules with different arrays of photodetectors and bandpass filters. For full spectrum signatures, a plurality of (four or more) different detector modules can be used. With the selection of detector modules, the total number of photo detectors (e.g., 16, 32, 64, 128) can differ. The differing detector modules may use different numbers of photodetectors to capture light. Generally, the more detectors one has, the more data can be analyzed and the increased spectral resolution can be achieved.

With a spectral flow cytometer, separation of the light beam data in a mixed sample is handled as a data processing operation over the different detector modules and their respective detectors. The data processing operations can be somewhat complex because separation of the light beam data requires more data manipulation (e.g., identifying different wavelengths and separating light beam data accordingly).

Cell geometric characteristics can be categorized though analysis of the forward and side scattering data. The cells in the fluidic flow are labeled by dyes of visible wavelengths ranging from 400 nm to 900 nm or dyes that fluorescent with ultraviolet non-visible wavelengths when excited by an ultraviolet laser. When excited by lasers, the dyes produce fluorescent light, which are collected by the fiber assembly and routed toward a detector module. The modular flow cytometry system maintains a relatively small size, partly with the optical plate assembly using compact semiconductor lasers in the visible spectrum, a multipower collection lens 2813,2913, and compact image detector arrays in the detector modules. That is, the collection lens 2813,2913 contributes to the design of the compact detector modules.

The collection lens can have a short focal length for the its multipower factor (e.g., 11.5× power). The collection lens, an objective lens, has a high numerical aperture (NA) facing the fluorescence emissions to capture more photons in the fluorescence emissions over a wide range of incident angles. The collection lens has a low NA of about facing the fibber head and its collection fiber to launch the fluorescent light into the fiber over a narrow cone angle. Accordingly, the collection lens converts from a high NA on one side to a low NA on the opposite side to support a magnification M in the input channel of each detector module.

The diameter of the core of the collection fiber assembly is between about 400 μm and 800 μm, and the fiber NA is about 0.12 for a core diameter of about 600 μm. The fiber output end can be tapered to a core diameter of between about 100 μm and 300 μm for controlling the imaging size onto the receiving photodiode.

The input end of the collection fiber can also include a lensed fiber end to increase the collection NA for allowing use of a fiber core diameter that is less than about 400 μm. Because the collection fiber has the flexibility to deliver the light anywhere in the flow cytometer system, the use of fiber for fluorescence light collection enables optimization of the location of the receiver assembly and electronics for a compact flow cytometer system.

To manufacture a low-cost flow cytometer, lower cost components can be introduced. An image array in each detector module can be formed out of a solid transparent material to provide a detector module that is reliable, low cost, and compact. Furthermore, the flow cytometer can use low cost off the shelf components, such as thin outline (TO) can photodetectors in the detector modules.

Advantages

There are a number of advantages to the embodiments of the invention. The following represents a few of the noteworthy advantages.

The similarity index, and the methods thereof, provide an objective measurement of interference between pairs (one to one interference measure) of fluorochromes. The user need not rely on their subjective judgement. The similarity index, the spectrum viewer, and the functional methods of computation and code execution, can shorten the time in the selection of fluorochromes and markers that are useful in a flow cytometry panel for a single sample and a single run through the flow cytometer. The similarity index can result in less adjustments being needed to a spillover matrix to discern the various colors and markers.

For a color flow cytometer panel representing a selected set of combinations of fluorochromes and cell markers for a sample run, the combinations of spectral interferences (many to many spectral interferences (referred to as spillovers)) can compromise the separations of positive and negative data clusters output by a flow cytometer analysis. The complexity index, and the methods thereof, gives an objective overall measure of spectral interference for a given selected set of combinations of fluorochromes and cell markers for a single sample run through a flow cytometer. Otherwise, a user needs to rely on subjective experience selecting set of combinations of fluorochromes and cell markers and running multiple tests to be sure the combinations of fluorochromes and cell markers are distinguishable.

The similarity index and/or complexity index can improve analysis productivity with a full spectrum flow cytometer. Greater number of fluorochromes, antibodies, and cell markers can be selected using the similarity index and/or complexity index to form larger flow cytometry panels with objective proof prior to actual testing. The time and number of runs spent analyzing a biological sample with a full spectrum flow cytometer can be reduced with a greater number of fluorochromes, antibodies, and cell markers from larger flow cytometry panels.

Larger flow cytometry panels can be generated objectively showing (proving) that a selected group of fluorochromes, conjugated antibodies, and cell markers of cells can be used in a single flow cytometer run to identify different biological cells in a single sample. This in turn allows the overall sample collected to be conserved for other possible tests. The larger color flow cytometry panels that can be generated can themselves offer advantages. The color plots can be arranged into the rows and columns of the color panels that makes it easy to understand complex and numerous data points of a flow cytometer output. The larger color flow cytometry panel makes it easy to show proof that the larger selection of set of fluorochromes and cell markers can be used with a given flow cytometer in a single sample and single run to identify biological cells.

Some portions of the preceding detailed description have been presented in terms of algorithms and symbolic representations of operations on data bits within a computer memory. These algorithmic descriptions and representations are the tools used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be kept in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as “processing” or “computing” or “calculating” or “determining” or “displaying” or the like, refer to the action and processes of a computer system, or similar electronic computing device, that manipulates and transforms data represented as physical (electronic) quantities within the computer system’s registers and memories into other data similarly represented as physical quantities within the computer system memories or registers or other such information storage, transmission or display devices.

The embodiments are thus described. While certain exemplary embodiments have been described and shown in the accompanying drawings, it is to be understood that such embodiments are merely illustrative of and not restrictive on the broad invention, and that the embodiments not be limited to the specific constructions and arrangements shown and described, since various other modifications may occur to those ordinarily skilled in the art.

When implemented in software, the elements of the embodiments of the invention are essentially the code segments to perform the necessary tasks. The program or code segments can be stored in a processor readable medium or transmitted by a computer data signal embodied in a carrier wave over a transmission medium or communication link. The “processor readable medium” may include any medium that can store information. Examples of the processor readable medium include an electronic circuit, a semiconductor memory device, a read only memory (ROM), a flash memory, an erasable programmable read only memory (EPROM), a floppy diskette, a CD-ROM, an optical disk, a hard disk, a fiber optic medium, a radio frequency (RF) link, etc. The computer data signal may include any signal that can propagate over a transmission medium such as electronic network channels, optical fibers, air, electromagnetic, RF links, etc. The code segments may be downloaded using a computer data signal via computer networks such as the Internet, Intranet, etc. and stored in a storage device (processor readable medium).

While this specification includes many specifics, these should not be construed as limitations on the scope of the disclosure or of what may be claimed, but rather as descriptions of features specific to particular implementations of the disclosure. Certain features that are described in this specification in the context of separate implementations may also be implemented in combination in a single implementation. Conversely, various features that are described in the context of a single implementation may also be implemented in multiple implementations, separately or in sub-combination. Moreover, although features may be described above as acting in certain combinations and even initially claimed as such, one or more features from a claimed combination may in some cases be excised from the combination, and the claimed combination may be directed to a sub-combination or variations of a sub-combination. Accordingly, while embodiments of the invention have been particularly described, they should not be construed as limited by such embodiments, but rather construed according to claims that follow below.

| Specificity | Fluorochrome | Clone | Purpose |
|---|---|---|---|
| Viability | ViaDye ™ Red Fixable Viability Dye | | Viability |
| CD45 | cFluor ™ R780 | 2D1 | Leukocytes |
| CD3 | BV570 | UCHT1 | Pan T cell, NKT-Like cells |
| CD4 | cFluor ™ YG584 | SK3 | CD4 T and NKT-Like cells |
| CD8 | cFluor ™ B532 | SK1 | CD8 T, NK, and NKT-Like cells |
| CD25 | cFluor ™ BYG575 | M-A251 | Regulatory T cells |
| TCRγδ | cFluor ™ BYG710 | B1 | Pan γδ T cell |
| CD14 | cFluor ™ B548 | 63D3 | Monocyte differentiation |
| CD16 | cFluor ™ BYG610 | 3G8 | Monocyte, NK cell, and dendritic cell differentiation |
| CD11c | cFluor ™ BYG781 | 3.9 | Dendritic Cell differentiation |
| CD19 | cFluor ™ R685 | HIB19 | B cells |
| CD20 | cFluor ™ V547 | 2H7 | B cells |
| IgD | cFluor ™ BYG667 | IA6-2 | B cell differentiation |
| IgM | BV510 | MHM-88 | B cell differentiation |
| CD141 | cFluor ™ B515 | M80 | Dendritic cell differentiation |
| CD1c | cFluor ™ R668 | L161 | Dendritic cells, NKT-Like cells |
| CD123 | cFluor ™ R720 | 6H6 | Plasmacytoid dendritic cells |
| CD56 | BV750 | 5.1H11 | Pan NK cell, γδ T cell activation |
| CCR7 | BV421 | G043H7 | T cell differentiation |
| CD27 | cFluor ™ R840 | QA17A18 | T and B cell differentiation |
| CD28 | BV650 | CD28.2 | T cell and NK cell differentiation |
| CD45RA | cFluor ™ V450 | HI100 | T cell and dendritic cell differentiation |
| CD127 | cFluor ™ R659 | A019D5 | Cytokine receptor; T cell differentiation |
| HLA-DR | cFluor ™ B690 | L243 | T cell and monocyte activation, NK cell lineage discrimination, dendritic cell lineage marker |
| CD38 | BV711 | HIT2 | Monocyte, dendritic cell, T cell, and B cell activation/differentiation |
| PD-1 | BV785 | EH12.2H7 | T cell inhibitory receptor |

What is claimed is:

1. A method of building a color flow cytometry panel using a full spectrum laser flow cytometer, the method comprising:

selecting twenty-five (25) cell markers for biological cells of interest;

identifying fluorochromes to be used in the flow cytometry panel;

analyzing full spectrum of each fluorochrome across detectors in the full spectrum laser flow cytometer, the full spectrum laser flow cytometer having at least four (4) lasers;

comparing spectra of combination of pairs of each of the commercially available fluorochromes by determining a similarity index for each pairing of fluorochromes;

selecting twenty-five (25) optimal fluorochromes using the similarity index and a complexity index for each of the fluorochromes;

calibrating the lasers and detectors in the flow cytometer;

pairing the twenty-five (25) optimal fluorochromes with the twenty-five (25) selected cell markers, according to the brightness of the fluorochrome and the expression density of the cell marker;

staining the biological cells of interest with the antibody conjugated fluorochromes, comprising the twenty-five (25) optimal fluorochromes and antibody specific to the twenty-five (25) cell markers, to create a multicolor sample;

running the multicolor sample through the full spectrum flow cytometer;

receiving data from the detectors of the full spectrum flow cytometer; and processing the received data using a computer processor to form the color flow cytometry panel.

2. The method of claim 1, wherein the biological cells of interest are selected from a group consisting of CD4 T cells, CD8 T cells, regulatory T cells (Tregs), γδ T cells, NKT-like cells, B cells, NK cells, innate lymphoid cells (ILCs), basophils, monocytes, and dendritic cells.

3. The method of claim 1, wherein selecting the twenty-five (25) optimal fluorochromes comprises, selecting the fluorochromes based on peak emission wavelength spread across the four laser colors of the full spectrum flow cytometer.

4. The method of claim 1, wherein selecting the twenty-five (25) optimal fluorochromes comprises, quantifying uniqueness of each of a group of sixty-five (65) fluorochromes.

5. The method of claim 4, wherein selecting the twenty-five (25) optimal fluorochromes comprises, analyzing the spectra of each of the sixty-five (65) fluorochromes using the full spectrum flow cytometer.

6. The method of claim 5, wherein selecting the twenty-five (25) optimal fluorochromes comprises, comparing the spectra of each pairing of the sixty-five (65) fluorochromes; and assigning a similarity index to each pairing of fluorochromes.

7. The method of claim 6, wherein selecting the twenty-five (25) optimal fluorochromes further comprises, determining a threshold similarity index value and not selecting at least one fluorochrome of the pair of fluorochromes with a similarity index value higher than the threshold similarity index value.

8. The method of claim 6, wherein selecting the twenty-five (25) optimal fluorochromes comprises, choosing the twenty-five (25) optimal fluorochromes with the lowest similarity index.

9. The method of claim 8, wherein the lowest similarity index value that will produce high resolution data is 0.98.

10. The method of claim 1, wherein identifying the twenty-five (25) optimal fluorochromes comprises:

determining a complexity index of the group of twenty-five (25) fluorochromes;

determining a threshold complexity index above which the group of twenty-five (25) fluorochromes are not considered optimal.

11. The method of claim 10, wherein the threshold complexity index is fifty-four (54).

12. The method of claim 1, wherein pairing the twenty-five (25) optimal fluorochromes with the twenty-five (25) selected cell markers comprises;

assigning the dimmest fluorochromes to the highest expressing antigens;

assigning tertiary markers to bright fluorochromes; and avoiding placing highly expressed antigens adjacent to co-expressed antigens with lower expression for fluorochromes with a same primary excitation laser or similar emission wavelengths.

13. The method of claim 1, wherein processing the received data comprises:

manually gating to remove aggregates, dead cells, debris, and CD45 negative events;

dating traditionally defined PBMC populations;

sub-sample the data to include only the CD45+ live singlets, unmix data using software with an ordinary least squares algorithm performing opt-SNE analysis of the data; and assembling clusters into commonly recognized biological populations and generate a heatmap of the resulting populations.

* * * * *